US008704044B2

(12) United States Patent
Gallie et al.

(10) Patent No.: US 8,704,044 B2
(45) Date of Patent: Apr. 22, 2014

(54) NUCLEIC ACIDS THAT ENCODE ERS1 FROM MAIZE AND THEIR USES

(75) Inventors: Daniel R. Gallie, Riverside, CA (US); Todd E. Young, Palm Springs, CA (US)

(73) Assignee: The Regents of the University of California, Oakland, CA (US)

(*) Notice: Subject to any disclaimer, the term of this patent is extended or adjusted under 35 U.S.C. 154(b) by 997 days.

(21) Appl. No.: 11/688,162

(22) Filed: Mar. 19, 2007

(65) Prior Publication Data
US 2008/0209585 A1 Aug. 28, 2008

Related U.S. Application Data

(63) Continuation of application No. 10/876,086, filed on Jun. 23, 2004, now Pat. No. 7,504,557.

(60) Provisional application No. 60/480,960, filed on Jun. 23, 2003.

(51) Int. Cl.
C12N 15/82 (2006.01)
C12N 15/87 (2006.01)
A01H 5/00 (2006.01)
C07H 21/04 (2006.01)

(52) U.S. Cl.
USPC ........ 800/298; 800/278; 800/295; 800/320.1; 536/23.1; 536/23.6; 435/320.1

(58) Field of Classification Search
None
See application file for complete search history.

(56) References Cited

U.S. PATENT DOCUMENTS

| 5,702,933 | A | 12/1997 | Klee et al. |
| 6,294,716 | B1 | 9/2001 | Meyerowitz et al. |
| 6,677,502 | B1* | 1/2004 | Allen et al. ................... 800/278 |
| 2006/0236419 | A1* | 10/2006 | La Rosa et al. ............... 800/278 |
| 2007/0099303 | A1 | 5/2007 | Orth et al. |

OTHER PUBLICATIONS

Chang et al., "*Arabidopsis* Ethylene-Response Gene *ETR1*: Similarity of Product of Two-Component Regulators," *Science*, 1993, pp. 539-544, vol. 262.
De Martinis and Mariani, "Silencing Gene Expression of the Ethylene-Forming Enzyme Results in a Reversible Inhibition of Ovule Development in Transgenic Tobacco Plants," *The Plant Cell*, Jun. 1999, pp. 1061-1071, vol. 11, American Society of Plant Physiologists.
Gepstein and Thimann, "The Role of Ethylene in the Senescence of Oat Leaves," *Plant Physiol.*, 1981, pp. 349-354, vol. 68.
Grossman, K. et al., "Regulation of Phytohormone Levels, Leaf Senescence and Transpiration by the Strobilurin Kresoxim-methyl in Wheat (*Triticum aestivum*)," *J. Plant Phys.*, 1999, pp. 805-808, vol. 154.
Guo, H. H. et al., "Protein tolerance to random amino acid change," *PNAS*, Jun. 22, 2007, pp. 9205-9210, vol. 101, No. 25.
Hill and Preiss, "Functional Analysis of Conserved Histidines in ADS-Glucose Pyrophosphorylase from *Escherichia Coli*," *Biochemical and Biophysical Research Communications*, 1998, pp. 573-577, vol. 244.
Hua and Meyerowitz, "Ethylene Responses are Negatively Regulated by a Receptor Gene Family in *Arabidopsis thaliana*," *Cell*, Jul. 24, 1998, pp. 261-271, vol. 94, Cell Press.
Hua et al., "*EIN4* and *ERS2* Are Members of the Putative Ethylene Receptor Gene Family in *Arabidopsis*," *Plant Cell*, 1998, pp. 1321-1332, vol. 10.
Hua et al., "Ethylene Insensitivity Conferred by *Arabidopsis* ERS Gene," *Science*, 1995, pp. 1712-1714, vol. 269.
Lazar, E. et al., "Transforming Growth Factor α: Mutation of Aspartic Acid 47 and Leucine 48 Results in Different Biological Activities," *Molecular and Cellular Biology*, Mar. 1988, pp. 1247-1252, vol. 8, No. 3.
Maeda et al., "A two-component system that regulates an osmosensing MAP kinase cascade in yeast," *Nature*, 1994, pp. 242-245, vol. 369.
Parkinson and Kofoid, "Communication Modules in Bacterial Signaling Proteins," *Annu. Rev. Genet.*, 1992, pp. 71-112, vol. 26.
Sakai et al., "*ETR2* is an *ETR1*-like gene involved in ethylene signaling in *Arabidopsis*," *Proc. Natl. Acad. Sci. USA*, 1998, pp. 5812-5817, vol. 95.
Sakakibara, H., ZmETR2 (2000) GenBank Accession AB040406, pp. 1-3.
Schaller and Bleeker, "Ethylene-Binding Sites Generated in Yeast Expressing the *Arabidopsis ETR1* Gene," *Science*, 1995, pp. 1809-1811, vol. 270.
Schuster et al., "The hybrid histidine kinase DokA is part of the osmotic response system of *Dictyostelium*," *EMBO J.*, 1996, pp. 3880-3889, vol. 15.
Thomas and Howarth, "Five ways to stay green," *Journal of Experimental Botany*, Feb. 2000, pp. 329-337, vol. 51, Oxford University Press.
Van Der Straeten, D. et al., "Ethylene: A small hormone with many functions," *Med. Fac. Landbouww. Univ. Gent.*, 1995, pp. 1567-1574, vol. 60, No. 4a.
Yip, W. et al., "The effects of antisense *LE-ACS2* and *LE-ACS4* transgenes on ethylene biosynthesis and fruit development in tomato," *Annual Meeting of the American Society of Plant Biologists*, 2002, Abstract No. 368, Denver, CO.
Young et al., "Ethylene-Mediated Programmed Cell Death during Maize Endosperm Development of Wild-Type and *shrunken2* Genotypes," *Plant Physiol.*, 1997, pp. 737-751, vol. 119.

(Continued)

*Primary Examiner* — Cathy Kingdon Worley
*Assistant Examiner* — Mykola Kovalenko
(74) *Attorney, Agent, or Firm* — Kilpatrick Townsend & Stockton LLP

(57) ABSTRACT

The present invention is directed to plant genetic engineering. In particular, it is directed to producing green leaves in maize through inhibition of ethylene. The genes involved in producing this phenotype include 1-Aminocyclopropane-1-Carboxylate ("ACC") synthase, ACC oxidase, ACC deaminase, ethylene response sensor ("ERS"), ethylene resistant ("ETR"), and ethylene insensitive ("EIN").

5 Claims, No Drawings

(56) References Cited

OTHER PUBLICATIONS

Young and Gallie, "Analysis of programmed cell death in wheat endosperm reveals differences in endosperm development between cereals," *Plant Mol. Biol.*, 1999, pp. 915-926, vol. 39.

Young and Gallie, "Regulation of programmed cell death in maize endosperm by abscisic acid," *Plant Mol. Biol.*, 2000, pp. 397-414, vol. 42.

Zacarias and Reid, "Role of growth regulators in the senescence of *Arabidopsis thaliana* leaves," *Physiologia Plantarum*, 1990, pp. 549-554, vol. 80, Copenhagen.

* cited by examiner

SEQUENCE LISTING

```
<160> NUMBER OF SEQ ID NOS: 50

<210> SEQ ID NO 1
<211> LENGTH: 2959
<212> TYPE: DNA
<213> ORGANISM: Zea mays
<220> FEATURE:
<223> OTHER INFORMATION: Zea mays (B73) 1-aminocyclopropane-1-
      carboxylate (ACC) oxidase, O15 genomic DNA

<400> SEQUENCE: 1
tcgcgaggcg gcttaaactt aggtcggctc ggagtggctc atgagcctcg agcgagcaga      60
gacgaaccga gccaagttgt agagctcatt ggtataacaa gccgagtcag tttgcaagtt     120
atgccaaatt aatgaatcta taaaataata atagatattg gataatttta tagatattcg     180
actcgttcct tatcatttaa tgatggattt atgataattt aaaatttaga ttacttataa     240
tgttaaatga tggtcatatt tcatatctat atacaataat agtcattgta taatgcaata     300
ttatttatca aggtgtagct cgcgagttga gtcgagcctc cttcttaatc ttattgagtg     360
gacgaaccaa gctgagccga gtcgagcttg gtcacccagc gagtcgagcc tccttcttaa     420
actcgttgaa tgagactcag ctcatttcta gccctaaaaa atcgcatcat catcggcata     480
aagcgagcaa tgcagacatt tttggtagta caagcttcgg atgaccggct gcagacgctt     540
tctcaataac cttctgtagg ggatcaatgg ccaagatgaa agagggtcac cttgatgaag     600
acttcaggcg tgtttaaatt ttttgcttgg gcgatcattc actagcactt tggaagatga     660
tgtagccaag atgctagtct ctctattttt gactgaaacc tagctagagc ttttaaaaca     720
tcccggagat agttaaggga atcaaaggct tttgaaatgt ccaatagata ccatttttt      780 tcttgtggag gaggctatga ataacatttt gttcatatag aaaattatca cattatgtga     840
caagcaaggg aaaataactt atatatagtt aatagtggag ggagtgtctg atataaaaag     900
ctacatattt ttgctggtta gttgttagtt aggtctttac ctgccctctc tctacgaacg     960
agctgatgcc agttctgact ttgtcaaagc atggctggca atgtgattga atgcctgatg    1020
ttagctcgtc accttgacag ggacatccga tcctgaattt ccgattgggg tggcaaaggt    1080
caagttgcca ccacaagcat cagtccaatg gctctgccac tgcccagaag cttcatcaca    1140
cctagaggta gccatgacag gacccaaaaa aaggtccagt ccaggtccgt accagctgcg    1200
acgacgcttg tcagtaggta ggttgagcta gctgcttgtt gatcactgct atatatacgg    1260
gtgccatgga tccatgcctt ctccatcctc aagtcatcag ctagctagcc ttccctacag    1320
caactgctta catacaacac ttccatcttc ccgagctcgt cttcgatcaa ttcccaagtc    1380
```

```
aaataataat ataacaacaa tggtggttcc cgtcatcgac ttctccaagc tggacggcgc   1440
tgagagggcc gaaaccctgg cgcagatcgc caatggctgc gaggagtggg gattcttcca   1500
gctcgtgaac cacggcatcc cgctggagct tcttgagcgc gtcaagaagg tgagctccga   1560
ctgctaccgc ctccgggagg ccgggttcaa ggcgtcggag ccgtgcgca cgctggaggc    1620 gctcgtcgac gcggagcggc gcggcgaggt tgtggccccg gtggatgacc tggactggga   1680
ggacatcttc tacatccacg acggatgcca gtggccgtcc gagccgccgg cgttcaagga   1740
gaccatgcgc gagtaccgcg ccgagctgag gaagctcgcc gagcgcgtca tggaggccat   1800
ggacgagaac ctcggcctcg ccaggggcac catcaaggac gccttctcca gcggcggccg   1860
gcacgagccc ttcttcggca ccaaggtcag ccactacccg ccgtgccgc gcccggacct    1920 catcacgggc ctgcgcgcgc acaccgacgc cggcggcgtc atcctgctgt tccaggacga   1980
cagggtcggc ggcctggagg tgctcaagga cggccagtgg accgacgtgc agccgctcgc   2040
gggcgccatc gtcgtcaaca ctggcgacca gattgaggtg ctcagcaacg ggcgctaccg   2100
cagcgcctgg caccgcgtgc tgcccatgcg cgacggcaac cgccgctcca tcgcttcctt   2160
ctacaacccg gccaacgagg ccaccatctc gccggcggcg gtgcaggcca gcggcggcga   2220 cgcataccc aagtacgtgt tcggcgacta catggacgtg tacgccaagc acaagttcca    2280
ggccaaggag cccaggttcg aagccgtcaa ggttgcagcg cccaagtcat ctccagcggc   2340
ataaataaat ggaggggacc aattattaaa tgcattataa tttatttgtt gaataaaaca   2400
gccggagaaa taatgataat gtaaagtata tatgataaac accggttagg atttaaggtg   2460 tttaactta gttgcatggt ataatatgat atattgttgt agcaataagt ttattaagta    2520
ttcataagtg ttctaaatag tgggctaagg cacttatcca tcgcctttct caaacagaaa   2580
atagtgattt aattcgggct atagcgacta atagttgcta tatatattag gcgtagtagc   2640
aaacaatttc acccttcgga aacagttata tctagaaata actatagcca gagatttaga   2700
accttgttaa tcatgtagaa attaaaggtt cgtcaagtca gagcggcacc gaacaagata   2760
aaaatgtgac ctcccctata tgcaaatgtc tgccaactta ttacattggt gggtgccatc   2820
ttactatgta caaatatatc gcggaaacca tattatcagc gtcgagaatt ggccataccc   2880
ctggatattg ataatatgcc ttgcgagatc tattgagctg aagaaaactc gtaggggtc    2940 tagctagtgc catacctaa                                                 2959
```

<210> SEQ ID NO 2
<211> LENGTH: 940
<212> TYPE: DNA
<213> ORGANISM: Zea mays
<220> FEATURE:
<223> OTHER INFORMATION: Zea mays (B73) 1-aminocyclopropane-1-
      carboxylate (ACC) oxidase, O15 coding sequence (CDS)

<400> SEQUENCE: 2

```
atggtggttc ccgtcatcga cttctccaag ctggacggcg ctgagagggc cgaaaccctg     60
gcgcagatcg ccaatggctg cgaggagtgg ggattcttcc agctcgtgaa ccacggcatc    120
ccgctggagc ttcttgagcg cgtcaagaag gtgagctcca ctgctaccg cctccgggag     180 gccgggttca aggcgtcgga gccggtgcgc acgctggagg cgctcgtcga cgcggagcgg    240
cgcggcgagg ttgtggcccc ggtggatgac ctggactggg aggacatctt ctacatccac    300
gacggatgcc agtggccgtc cgagccgccg gcgttcaagg agaccatgcg cgagtaccgc    360
gccgagctga ggaagctcgc cgagcgcgtc atggaggcca tggacgagaa cctcggcctc    420
gccaggggca ccatcaagga cgccttctcc agcggcggcc ggcacgagcc cttcttcggc    480
```

```
accaaggtca gccactaccc gccgtgcccg cgcccggacc tcatcacggg cctgcgcgcg    540
cacaccgacg ccggcggcgt catcctgctg ttccaggacg cagggtcgg cggcctggag     600 gtgctcaagg acggccagtg gaccgacgtg cagccgctcg cgggcgccat cgtcgtcaac    660
actggcgacc agattgaggt gctcagcaac gggcgctacc gcagcgcctg caccgcgtg    720 ctgcccatgc gcgacggcaa ccgccgctcc atcgcttcct tctacaaccc ggccaacgag    780
gccaccatct cgccggcggc ggtgcaggcc agcggcggcg acgcataccc caagtacgtg    840
ttcggcgact acatggacgt gtacgccaag cacaagttcc aggccaagga gcccaggttc    900
gaagccgtca aggttgcagc gcccaagtca tctccagcgg                         940
```

<210> SEQ ID NO 3
<211> LENGTH: 314
<212> TYPE: PRT
<213> ORGANISM: Zea mays
<220> FEATURE:
<223> OTHER INFORMATION: Zea mays (B73) 1-aminocyclopropane-1-
carboxylate (ACC) oxidase, O15 protein <400> SEQUENCE: 3

```
Met Val Val Pro Val Ile Asp Phe Ser Lys Leu Asp Gly Ala Glu Arg
  1               5                  10                  15

Ala Glu Thr Leu Ala Gln Ile Ala Asn Gly Cys Glu Glu Trp Gly Phe
             20                  25                  30

Phe Gln Leu Val Asn His Gly Ile Pro Leu Glu Leu Leu Glu Arg Val
         35                  40                  45

Lys Lys Val Ser Ser Asp Cys Tyr Arg Leu Arg Glu Ala Gly Phe Lys
     50                  55                  60

Ala Ser Glu Pro Val Arg Thr Leu Glu Ala Leu Val Asp Ala Glu Arg
 65                  70                  75                  80

Arg Gly Glu Val Val Ala Pro Val Asp Asp Leu Asp Trp Glu Asp Ile
                 85                  90                  95

Phe Tyr Ile His Asp Gly Cys Gln Trp Pro Ser Glu Pro Pro Ala Phe
            100                 105                 110

Lys Glu Thr Met Arg Glu Tyr Arg Ala Glu Leu Arg Lys Leu Ala Glu
        115                 120                 125

Arg Val Met Glu Ala Met Asp Glu Asn Leu Gly Leu Ala Arg Gly Thr
    130                 135                 140

Ile Lys Asp Ala Phe Ser Ser Gly Gly Arg His Glu Pro Phe Phe Gly
145                 150                 155                 160

Thr Lys Val Ser His Tyr Pro Pro Cys Pro Arg Pro Asp Leu Ile Thr
                165                 170                 175

Gly Leu Arg Ala His Thr Asp Ala Gly Gly Val Ile Leu Leu Phe Gln
            180                 185                 190

Asp Asp Arg Val Gly Gly Leu Glu Val Leu Lys Asp Gly Gln Trp Thr
        195                 200                 205

Asp Val Gln Pro Leu Ala Gly Ala Ile Val Val Asn Thr Gly Asp Gln
    210                 215                 220

Ile Glu Val Leu Ser Asn Gly Arg Tyr Arg Ser Ala Trp His Arg Val
225                 230                 235                 240

Leu Pro Met Arg Asp Gly Asn Arg Arg Ser Ile Ala Ser Phe Tyr Asn
                245                 250                 255

Pro Ala Asn Glu Ala Thr Ile Ser Pro Ala Ala Val Gln Ala Ser Gly
            260                 265                 270

Gly Asp Ala Tyr Pro Lys Tyr Val Phe Gly Asp Tyr Met Asp Val Tyr
```

```
                    275                 280                 285
Ala Lys His Lys Phe Gln Ala Lys Glu Pro Arg Phe Glu Ala Val Lys
            290                 295                 300

Val Ala Ala Pro Lys Ser Ser Pro Ala Ala
305                 310

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O15 (ZmACO15) forward primer

<400> SEQUENCE: 4
ctcgtcttcg atcaattccc aagt                                            24

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O15 (ZmACO15) reverse primer

<400> SEQUENCE: 5
tacattatca ttatttctcc ggctgt                                          26

<210> SEQ ID NO 6
<211> LENGTH: 1516
<212> TYPE: DNA
<213> ORGANISM: Zea mays
<220> FEATURE:
<223> OTHER INFORMATION: Zea mays (W64) 1-aminocyclopropane-1-
      carboxylate (ACC) oxidase, O20 genomic DNA (truncated)
<220> FEATURE:
<221> NAME/KEY: modified_base
<222> LOCATION: (30)
<223> OTHER INFORMATION: n = g, a, c or t

<400> SEQUENCE: 6
attccgttgc ccctgtcaag tgtacatcan attgaatgct gtgttaggcc agcaactatc     60
acaatcccaa gtcatagcag gtgacggtgc gatcgacgcg ctttgtttgg tggaacattt    120
tcccgtgttc aattctttct tccctttcttt ttttttttaa aaaaaaagct ttccgtgtcg   180
ctgctgcagc aagtgatgaa gcagttcgca tcggaggtgc agaagctgtc ggagaaggtg    240
ctggacttgc tgtgcgagaa cctgggcctg gagcccgggt acctgaaggc ggccttcgcg    300
gggtcggacg gcggcccgac gttcggcacc aaggtgagcg cgtacccgcc gtgcccgcgc    360
ccggacctgg tggccggcct gcgcgcgcac accgacgccg gcggcctcat cctgctgctc    420
caggacgacc aggtgagcgg gctgcagctg ctcaggggcg gcgacggcgg ggagtgggtg    480
aacgtgccgc cgctgcgcca cgccatcgtc gccaacgtcg gcgaccagct ggaggtggtc    540
accaacgggc ggtacaagag cgcggtgcac gcgcgtgctcg cccgccccga cggcaaccgc    600
atgtccgtcg cgtccttcta caacccgggc gccgacgccg tcatcttccc ggccccgcg    660 ctcgtcggcg aggaggagcg agccgagaag aaggccacca cgtacccgag gttcgtgttc    720
gaggactaca tgaacctgta cgcgcgccac aagttcgagg ccaaggagcc ccggttcgag    780
gccatgaagt cgtcggccat cgccaccgcg tgagcacata atactgccgt gttctcccctt    840 cgtggggtgc atatgcttga gcttgaagag ccatgtgcct gtatgtagtg gcacgtacgg    900
```

```
tggttatgcg tgtatcgtgg aatggcgcgg cgtgatgtat tttggttgtc tcagatctaa    960
gtgtgtgcgt atatattgtg tactgtaaag tttgcagcgt ctgattaatg tacgagcagt   1020
gtgtgtacct aaccagaacc tggaatgtgg ctggctgtgt gctgatatta ctaccacatc   1080
aggtgagtgg ccaccgtcg tcgcctccta cggctccggt gccgactcga ccccttcctt   1140
ccctgcgacc ctgcgcccc accgcccta tctccatgga tacttgcggc gagcaaaggc   1200
ttaacaaagg agaacagtgt gcaaaacata cctgcagtga gcaaaggctt acatgagga   1260 tatcaggata tgcacagacc taccatacaa gctatagcct ttcctttaca acaaaacacc   1320
agctagaaga tccgcatatg ctaccgattg ttcactctcc atgttttgtt cggcttacat   1380
tgttacgctg agttagatgg ttaattgcac agtaacctgc cgactgcact atcaccttgt   1440
cttggctttc cttctcttct atacaaaagc gagtcagtgg acacattcag agaagtggaa   1500
gggaagaaag aagaaa                                                   1516

<210> SEQ ID NO 7
<211> LENGTH: 969
<212> TYPE: DNA
<213> ORGANISM: Zea mays
<220> FEATURE:
<223> OTHER INFORMATION: Zea mays (W64) 1-aminocyclopropane-1-
      carboxylate (ACC) oxidase, O20 coding sequence (CDS)

<400> SEQUENCE: 7
atggcagcca cggtgtcctt cccggtggtg aacatggaga agctggagac cgaggagagg     60
gacacggcca tggcggtcat ccgcgacgcc tgcgagaact ggggcttctt cgagctgctg    120
aaccatggca tctcgcacga gctgatgac gaggtggagc ggctgaccaa ggcgcactac    180
gccaccttcc gggaggccaa gttccaggag ttcgcggcgc ggacgctggc cgcggccggc    240
gacgagggcg ccgacgtcag cgacgtggac tgggagagca ccttcttcgt ccgccacctc    300
ccggcctcca acctcgccga cctccccgac gtcgacgacc actaccggca agtgatgaag    360
cagttcgcat cggaggtgca gaagctgtcg gagaaggtgc tggacctgct gtgcgagaac    420
ctgggcctgg agcccgggta cctgaaggcg gccttcgcgg ggtcgacgg cggcccgacg    480 ttcggcacca aggtgagcgc gtacccgccg tgcccgcgcc cggacctggt ggccggcctg    540
cgcgcgcaca ccgacgccgg cggcctcatc ctgctgctcc aggacgacca ggtgagcggg    600
ctgcagctgc tcaggggcgg cgacggcggg gagtgggtgg acgtgccgcc gctgcgccac    660
gccatcgtcg ccaacgtcgg cgaccagctg gaggtggtca ccaacgggcg gtacaagagc    720
gcggtgcacc gcgtgctcgc ccgccccgac ggcaaccgca tgtccgtcgc gtccttctac    780
aacccgggcg ccgacgccgt catcttcccg gccccgcgc tcgtcggcga ggaggagcga    840
gccgagaaga aggccaccac gtacccgagg ttcgtgttcg aggactacat gaacctgtac    900
gcgcgccaca gttcgaggc caaggagccc cggttcgagg ccatgaagtc gtcggccatc    960
gccaccgcg                                                           969

<210> SEQ ID NO 8
<211> LENGTH: 323
<212> TYPE: PRT
<213> ORGANISM: Zea mays
<220> FEATURE:
<223> OTHER INFORMATION: Zea mays (W64) 1-aminocyclopropane-1-
      carboxylate (ACC) oxidase, O20 protein

<400> SEQUENCE: 8

Met Ala Ala Thr Val Ser Phe Pro Val Val Asn Met Glu Lys Leu Glu
```

```
            1               5              10              15
Thr Glu Glu Arg Asp Thr Ala Met Ala Val Ile Arg Asp Ala Cys Glu
                20                  25                  30

Asn Trp Gly Phe Phe Glu Leu Leu Asn His Gly Ile Ser His Glu Leu
            35                  40                  45

Met Asp Glu Val Glu Arg Leu Thr Lys Ala His Tyr Ala Thr Phe Arg
 50                  55                  60

Glu Ala Lys Phe Gln Glu Phe Ala Ala Arg Thr Leu Ala Ala Ala Gly
 65                  70                  75                  80

Asp Glu Gly Ala Asp Val Ser Asp Val Asp Trp Glu Ser Thr Phe Phe
                85                  90                  95

Val Arg His Leu Pro Ala Ser Asn Leu Ala Asp Leu Pro Asp Val Asp
                100                 105                 110

Asp His Tyr Arg Gln Val Met Lys Gln Phe Ala Ser Glu Val Gln Lys
                115                 120                 125

Leu Ser Glu Lys Val Leu Asp Leu Leu Cys Glu Asn Leu Gly Leu Glu
        130                 135                 140

Pro Gly Tyr Leu Lys Ala Ala Phe Ala Gly Ser Asp Gly Pro Thr
145                 150                 155                 160

Phe Gly Thr Lys Val Ser Ala Tyr Pro Pro Cys Pro Arg Pro Asp Leu
                165                 170                 175

Val Ala Gly Leu Arg Ala His Thr Asp Ala Gly Gly Leu Ile Leu Leu
                180                 185                 190

Leu Gln Asp Asp Gln Val Ser Gly Leu Gln Leu Leu Arg Gly Gly Asp
        195                 200                 205

Gly Gly Glu Trp Val Asp Val Pro Pro Leu Arg His Ala Ile Val Ala
        210                 215                 220

Asn Val Gly Asp Gln Leu Glu Val Val Thr Asn Gly Arg Tyr Lys Ser
225                 230                 235                 240

Ala Val His Arg Val Leu Ala Arg Pro Asp Gly Asn Arg Met Ser Val
                245                 250                 255

Ala Ser Phe Tyr Asn Pro Gly Ala Asp Ala Val Ile Phe Pro Ala Pro
                260                 265                 270

Ala Leu Val Gly Glu Glu Arg Ala Glu Lys Lys Ala Thr Thr Tyr
        275                 280                 285

Pro Arg Phe Val Phe Glu Asp Tyr Met Asn Leu Tyr Ala Arg His Lys
        290                 295                 300

Phe Glu Ala Lys Glu Pro Arg Phe Glu Ala Met Lys Ser Ser Ala Ile
305                 310                 315                 320

Ala Thr Ala

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:Zea mays
      (W64) 1-aminocyclopropane-1-carboxylate (ACC) oxidase,
      O20 (ZmACO20) forward primer, ACOF1 primer

<400> SEQUENCE: 9
ctcatcctgc tgctccagga cgac                                        24

<210> SEQ ID NO 10
<211> LENGTH: 25
<212> TYPE: DNA
<213> ORGANISM: Artificial Sequence
```

```
<220> FEATURE:
<223> OTHER INFORMATION: Description of Artificial Sequence:Zea mays
      (W64) 1-aminocyclopropane-1-carboxylate (ACC) oxidase,
      O20 (ZmACO20) reverse primer

<400> SEQUENCE: 10
tccacgatac acgcataacc accgt                                         25

<210> SEQ ID NO 11
<211> LENGTH: 942
<212> TYPE: DNA
<213> ORGANISM: Zea mays
<220> FEATURE:
<223> OTHER INFORMATION: Zea mays (B73) 1-aminocyclopropane-1-
      carboxylate (ACC) oxidase, O31 coding sequence (CDS)

<400> SEQUENCE: 11
atggtggttc ccgtgatcga cttctccaag ctggacggcg ctgagagggc tgaaaccctg    60
gcgcagatcg ccaatggctg cgaggagtgg ggattcttcc agctcgtgaa ccacggcatc   120
ccgctggagc tgctcgagcg cgtcaagaag gtgtgctccg actgctaccg cctccgggag   180
gccgggttca aggcgtcgga gccggtgcgc acgctggagg cgctcgtcga cgcggagcgg   240
cgcggtgagg tggtggcgcc ggtggacgac ctggactggg aggacatctt ctacatccac   300
gacggatgcc agtggccgtc cgacccgccg gcgttcaagg agaccatgcg cgagtaccgc   360
gccgagctga ggaagctcgc cgagcgagtc atggaggcca tggacgagaa cctcggcctc   420
gccaggggca ccatcaagga cgccttctcc ggcggcggcc ggcacgatcc cttcttcggc   480
accaaggtca gccactaccc gccgtgccca cgcccggacc tcatcacggg cctgcgcgcg   540
cacaccgacg ccggcggcgt catcctcctg ttccaggacg acaaggtcgg tggcctggag   600
gtgctcaagg acggcgagtg gaccgacgta cagccgctcg agggcgccat cgtcgtcaac   660
accggcgacc agatcgaggt gctcagcaac gggctgtacc gcagcgcttg gcaccgcgtg   720
ctgcccatgc gcgacggcaa tcgccgctcc atcgcatcct tctacaaccc agccaacgaa   780
gccaccatct cgccggcggc ggtgcaggcc agcggcggtg acgcgtatcc caagtacttg   840
ttcggcgatt acatggacgt gtacgtcaag cagaagttcc aggccaagga gcctaggttc   900
gaagccgtca agacgggggc gccaaagtca tctccagcgg ca                     942

<210> SEQ ID NO 12
<211> LENGTH: 314
<212> TYPE: PRT
<213> ORGANISM: Zea mays
<220> FEATURE:
<223> OTHER INFORMATION: Zea mays (B73) 1-aminocyclopropane-1-
      carboxylate (ACC) oxidase, O31 protein

<400> SEQUENCE: 12

Met Val Val Pro Val Ile Asp Phe Ser Lys Leu Asp Gly Ala Glu Arg
  1               5                  10                  15

Ala Glu Thr Leu Ala Gln Ile Ala Asn Gly Cys Glu Glu Trp Gly Phe
             20                  25                  30

Phe Gln Leu Val Asn His Gly Ile Pro Leu Glu Leu Leu Glu Arg Val
         35                  40                  45

Lys Lys Val Cys Ser Asp Cys Tyr Arg Leu Arg Glu Ala Gly Phe Lys
     50                  55                  60

Ala Ser Glu Pro Val Arg Thr Leu Glu Ala Leu Val Asp Ala Glu Arg
 65                  70                  75                  80

Arg Gly Glu Val Val Ala Pro Val Asp Asp Leu Asp Trp Glu Asp Ile
                 85                  90                  95
```

```
Phe Tyr Ile His Asp Gly Cys Gln Trp Pro Ser Asp Pro Pro Ala Phe
                100                 105                 110
Lys Glu Thr Met Arg Glu Tyr Arg Ala Glu Leu Arg Lys Leu Ala Glu
            115                 120                 125
Arg Val Met Glu Ala Met Asp Glu Asn Leu Gly Leu Ala Arg Gly Thr
        130                 135                 140
Ile Lys Asp Ala Phe Ser Gly Gly Arg His Asp Pro Phe Phe Gly
145                 150                 155                 160
Thr Lys Val Ser His Tyr Pro Pro Cys Pro Arg Pro Asp Leu Ile Thr
                165                 170                 175
Gly Leu Arg Ala His Thr Asp Ala Gly Gly Val Ile Leu Leu Phe Gln
            180                 185                 190
Asp Asp Lys Val Gly Gly Leu Glu Val Leu Lys Asp Gly Glu Trp Thr
        195                 200                 205
Asp Val Gln Pro Leu Glu Gly Ala Ile Val Asn Thr Gly Asp Gln
    210                 215                 220
Ile Glu Val Leu Ser Asn Gly Leu Tyr Arg Ser Ala Trp His Arg Val
225                 230                 235                 240
Leu Pro Met Arg Asp Gly Asn Arg Arg Ser Ile Ala Ser Phe Tyr Asn
                245                 250                 255
Pro Ala Asn Glu Ala Thr Ile Ser Pro Ala Ala Val Gln Ala Ser Gly
            260                 265                 270
Gly Asp Ala Tyr Pro Lys Tyr Leu Phe Gly Asp Tyr Met Asp Val Tyr
        275                 280                 285
Val Lys Gln Lys Phe Gln Ala Lys Glu Pro Arg Phe Glu Ala Val Lys
    290                 295                 300
Thr Gly Ala Pro Lys Ser Ser Pro Ala Ala
305                 310

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O31 (ZmACO31) forward primer

<400> SEQUENCE: 13
ctcgtcttcg atcaattccc aagt                                              24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O31 (ZmACO31) reverse primer

<400> SEQUENCE: 14
atagcaaaga gggcaactag ctagt                                             25

<210> SEQ ID NO 15
<211> LENGTH: 4336
<212> TYPE: DNA
<213> ORGANISM: Zea mays
<220> FEATURE:
<223> OTHER INFORMATION: Zea mays (B73) 1-aminocyclopropane-1-
      carboxylate (ACC) oxidase, O35 genomic DNA
```

<400> SEQUENCE: 15

```
cttaagattg ggcttcagtg actaacaatc cgcatatata ttcttttggt gctagtttga      60
aaattgaaat cctctccggg atttctgggg attgagactc aatctccagg aatcccgagg     120
tggtttaagt tttaaaacta gtcttaaagt tttaatgcaa taaatacaa aatttaatgt      180
acttatgtcg gaatttattt ggaacaaata aaaacaggaa tttgctaatt ttggtaggtg     240
gtgcggcggt gaccgaaaaa aacatgaaaa gccgtattca aatctggatt cgttgtggag     300
tacctacgta tgccaatatc tctaaagtat aggattaggc caatagataa ctaggtcata     360
taatagcacc acagccgtat gatatcgtac aatattataa tgtacatcat atatatccag     420
cctaattagc tggggtcagt tgcaataatc ttcagaggac ttgtctgtat ctcgagtagc     480
ccgcataatt gcggctcgcc gtgcccgtgc acacgtctag ttatagatgt gtaaaaaaaa     540
tctgtccact cggtatatgg tccactcagc tcgccgtgca cgcatctagt ttgagatgac     600
gcggtgcgat gaaggggtcg cacggaggag gggaggggga gttagggtta gcaggcaagt     660
tgagtggtgt gctggttgtc tagtaaaatc ttagcagact tttgtagatt aggtcatact     720
gtgtcaaact gtcaactgcc gtacacgata ggcgatttgc taaattacca atattattag     780
gccttgttcg gttattccca atacacctgg attgaatgag attggaaaaa attcttaaga     840
actttgaatt gtttgggatt caaacccatc caatcccact caatccacat ggattgagag     900
ctaaccgaac aagcccttag tgggtttcag agattttatc ttcagaccta taaattatag     960
gtgcagatat atagactaaa aaacatagac atagatggta ttatagcaag aaggaacaaa    1020
ttcagtgcta attatttcga atacggtact gcacatccgg actgtcctgt cccagcctct    1080
cccaggttgc atgctcatct acaccgtcga gcgtcgaggc ggctagctct agccgatcag    1140
cgagcatcgc gggctatata cgtccagact gctttcattt gagaatgcgt agtttggctt    1200
cctaatccat ttgagtaaat tatgaaagta atgataaacg taccgtcgcg aggtcactct    1260
ggtaatccaa catttctcgc tcagccgcct ataaattggg ccgcgcgcac cgcctcgctc    1320
tccactcaaa caaactcaag cctgccctgc cctgccttgt taagcaaagc aacccagctg    1380
cgagacacga gagctagcta gagagagatg gcggccacgg tttcctcctt cccggtggtg    1440
aacatggaga agctggagac agaggagagg gccacggcca tggaggtcat ccgcgacggc    1500
tgcgagaact ggggcttctt cgaggtgtgc atatacatac tctgcagact gcttgctgct    1560
cacaccaagc taccacagaa cacaattatt ctactaacca acgcaccaca cctgatcaca    1620
ataagtaatg atctaaccac acagcaggaa gaattactac ttcacttgtt gtttgcctga    1680
cctgccaccc ccctgcttct tcaacatcta gagccccttc attctgtcag cacatgcaag    1740
ctgttcgttt cggatcaaat ctatttgttc ggactgctga cagtagaaac cgatactcgt    1800
taaagccagc accaccgttc cagaaaaaga aaagcaaaac aaagtattct agcagcttgc    1860
tttacctaac aaacagcctc cgatcctcga acgtacagat tcctattctc catgccatca    1920
accggccgac caccagctga ttccatcacg tctctctctc accgcgccta gctgatgagc    1980
acacacaaag tagcatctta tctattggtt cgttgatgcc cagctctcga acgaatcacc    2040
atctcatgta ttgtcttgtc cccatcccca tgcatgcagc tgctgaacca cggcatctcg    2100
cacgagctga tggacgaggt ggagcggctg accaaggcgc actacgccac cttccgggag    2160
gccaagttcc aggagttcgc ggcccggacg ctggaggccg gcgagaaggg cgccgacgtc    2220
aaggacgtgg actgggagag caccttcttc gtccgccacc tcccggcctc caacctcgcc    2280
gacctccccg acgtcgacga ccgctacagg tgcgttcaga cctcaaacac aacactacgt    2340
```

```
gcgtgcgtgc gtgctagcta gctagcttat gcgcgccatt aaattaatga cgtctggcgc    2400
acagggccgg gccggcataa ttgaaggccc tgtactgttt ttttttcttt tttttctttg    2460
ttaagaatag atgatacaga ttaatctcat ttattaacag tgattgaatt attaatgtag    2520
gaaatggctt aataacgata acaaatgatc ttaaagtttg gattttatgc tagcatgtgc    2580
tagctgcact tcgccatata gccaaaataa gttgcatgag agattggtac tcgcttgtta    2640
cgacaaacac tatgttttat tcttatcgag ctgacttagc tagactttct aatcattact    2700
aaaatttata ttgattaaat tatcactaac tattatttta ggggcccttg aagggagggg    2760
gccctgttct tgtgcactag tgacacatgc ctcccgcccg ggcctgctgg cgcagtatcg    2820
tatatttatt agtgtttggc tgctagctgc gacccaatga tcagtcgtct ttgttaatcg    2880 acttttttgtt ggcttctgac ggatgttcta agtgccatgt cacccgcttt tgactgatca    2940
gtttatttta attgatctga ttagtcttag cttgagagtg acttgagtat agcaggctgg    3000
gatactacct gacctgctcc tacataacgg attaagtaat gtttcaagaa attttgtcca    3060
tacgcatata attaagttat cattatcaga attctgcctg acgacgacga cgacgacgcg    3120
aaaacagtta gttatctgtt catctcgttg cctttaattg cttgacaagc tagctagcta    3180
gctgtacagc agaatgcggt gcgagccccg tagctatgac aaggtcgatc gaatcgcctt    3240
ttcagcaggc gacagcgcta tttgtccggt ggaattattc cggccgtgtc tcaaagcctt    3300
ccttccgtac gtgtcgctgc aggcaggtga tggagcagtt cgcatcggag atccgcaagc    3360
tgtcggagag gctgctggac ctgctgtgcg agaacctggg cctggagccc gggtacctga    3420
aggcggcctt cgcggggtcg gacggcccga cgttcggcac caaggtgagc gcgtacccgc    3480
cgtgcccgcg cccggacctc gtcgacggcc tccgcgcgca caccgacgcc ggcggcatcg    3540
tgctgctgtt ccaggacgac caggtgagcg gcctgcagct gctcaggggc ggggagtggg    3600
tggacgtgcc gcccatgcgc cacgccatcg tcgccaacgt cggcgaccag ctggaggtga    3660
tcaccaacgg gcggtacaag agcgtcatgc accgcgtgct cacgcgcccc gacggcaacc    3720
gcatgtccgt cgcgtccttc tacaacccgg gcgccgacgc cgtcatcttc ccggcccccg    3780
cgctcgtcgg cgccgccgag gaggaccgcg ccgaggccgc gtacccgagc ttcgtgttcg    3840
aggactacat gaacctgtac gtgcgccaca gttcgaggc caaggagccc aggttcgagg    3900
ccatgaagtc ggccatcgcc accgcgtgag agaagactgc cttccgctgc aggcttcctt    3960
cgtggcgtca agccttgagg cttgaacgaa caacgtacgt ccatgtgctt atagtggcac    4020
agttatgtgt gtaactaccg atcgtggaac ggcctaatgt atttcggttg cctcagatcg    4080
atctatatgt gcgtatacat tatgtactga aaagtgtgta gcgtctggtt aatgtatgag    4140
cagtgtgtat gtgaccggga cccggtgtgt agttgctatt actaccatat ccggtgaatg    4200
atcaaacctt ttggtgtatt aaaactagat gttcatcccc tcacggacta ccctggtatt    4260
gacaaccaaa acgaatatg acatatatag taaaaacatg atttcccggc caagaaaggg    4320
gactattcca actcgg                                                    4336
```

<210> SEQ ID NO 16
<211> LENGTH: 951
<212> TYPE: DNA
<213> ORGANISM: Zea mays
<220> FEATURE:
<223> OTHER INFORMATION: Zea mays (B73) 1-aminocyclopropane-1-
      carboxylate (ACC) oxidase, O35 coding sequence (CDS)
<220> FEATURE:
<221> NAME/KEY: modified_base
<222> LOCATION: (58)
<223> OTHER INFORMATION: n = g, a, c or t

<400> SEQUENCE: 16

```
atggcggcca cggtttcctc cttcccggtg gtgaacatgg agaagctgga gacagaggag    60
agggccacgg ccatggaggt catccgcgac ggctgcgaga actggggctt cttccagctg   120
ctgaaccacg gcatctcgca cgagctgatg gacgaggtgg agcggctgac caaggcgcac   180
tacgccacct tccgggaggc caagttccag gagttcgcgg cccggacgct ggaggccggc   240
gagaagggcg ccgacgtcaa ggacgtggac tgggagagca ccttcttcgt ccgccacctc   300
ccggcctcca acctcgccga cctccccgac gtcgacgacc gctacaggca ggtgatggag   360
cagttcgcat cggagatccg caagctgtcg gagaggctgc tggacctgct gtgcgagaac   420
ctgggcctgg agcccgggta cctgaaggcg ccttcgcgg gtcggacgg cccgacgttc   480
ggcaccaagg tgagcgcgta cccgccgtgc ccgcgcccgg acctcgtcga cggcctccgc   540
gcgcacaccg acgccggngg catcgtgctg ctgttccagg acgaccaggt gagcggcctg   600
cagctgctca ggggcgggga gtgggtggac gtgccgccca tgcgccacgc catcgtcgcc   660
aacgtcggcg accagctgga ggtgatcacc aacgggcggt acaagagcgt catgcaccgc   720
gtgctcacgc gccccgacgg caaccgcatg tccgtcgcgt ccttctacaa cccgggcgcc   780
gacgccgtca tcttcccggc ccccgcgctc gtcggcgccg ccgaggagga ccgcgccgag   840
gccgcgtacc cgagcttcgt gttcgaggac tacatgaacc tgtacgtgcg ccacaagttc   900
gaggccaagg agcccaggtt cgaggccatg aagtcggcca tcgccaccgc g             951
```

<210> SEQ ID NO 17
<211> LENGTH: 317
<212> TYPE: PRT
<213> ORGANISM: Zea mays
<220> FEATURE:
<223> OTHER INFORMATION: Zea mays (B73) 1-aminocyclopropane-1-
      carboxylate (ACC) oxidase, O35 protein

<400> SEQUENCE: 17

```
Met Ala Ala Thr Val Ser Ser Phe Pro Val Val Asn Met Glu Lys Leu
  1               5                  10                  15

Glu Thr Glu Glu Arg Ala Thr Ala Met Glu Val Ile Arg Asp Gly Cys
             20                  25                  30

Glu Asn Trp Gly Phe Phe Gln Leu Leu Asn His Gly Ile Ser His Glu
         35                  40                  45

Leu Met Asp Glu Val Glu Arg Leu Thr Lys Ala His Tyr Ala Thr Phe
     50                  55                  60

Arg Glu Ala Lys Phe Gln Glu Phe Ala Ala Arg Thr Leu Glu Ala Gly
 65                  70                  75                  80

Glu Lys Gly Ala Asp Val Lys Asp Val Asp Trp Glu Ser Thr Phe Phe
                 85                  90                  95

Val Arg His Leu Pro Ala Ser Asn Leu Ala Asp Leu Pro Asp Val Asp
            100                 105                 110

Asp Arg Tyr Arg Gln Val Met Glu Gln Phe Ala Ser Glu Ile Arg Lys
        115                 120                 125

Leu Ser Glu Arg Leu Leu Asp Leu Leu Cys Glu Asn Leu Gly Leu Glu
    130                 135                 140

Pro Gly Tyr Leu Lys Ala Ala Phe Ala Gly Ser Asp Gly Pro Thr Phe
145                 150                 155                 160

Gly Thr Lys Val Ser Ala Tyr Pro Pro Cys Pro Arg Pro Asp Leu Val
                165                 170                 175

Asp Gly Leu Arg Ala His Thr Asp Ala Gly Gly Ile Val Leu Leu Phe
```

```
                         180                 185                 190
Gln Asp Asp Gln Val Ser Gly Leu Gln Leu Leu Arg Gly Gly Glu Trp
            195                 200                 205

Val Asp Val Pro Pro Met Arg His Ala Ile Val Ala Asn Val Gly Asp
        210                 215                 220

Gln Leu Glu Val Ile Thr Asn Gly Arg Tyr Lys Ser Val Met His Arg
225                 230                 235                 240

Val Leu Thr Arg Pro Asp Gly Asn Arg Met Ser Val Ala Ser Phe Tyr
                245                 250                 255

Asn Pro Gly Ala Asp Ala Val Ile Phe Pro Ala Pro Leu Val Gly
            260                 265                 270

Ala Ala Glu Glu Asp Arg Ala Glu Ala Ala Tyr Pro Ser Phe Val Phe
        275                 280                 285

Glu Asp Tyr Met Asn Leu Tyr Val Arg His Lys Phe Glu Ala Lys Glu
    290                 295                 300

Pro Arg Phe Glu Ala Met Lys Ser Ala Ile Ala Thr Ala
305                 310                 315

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O35 (ZmACO35) forward primer

<400> SEQUENCE: 18
ctcatcctgc tgctccagga cgac                                              24

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O35 (ZmACO35) reverse primer

<400> SEQUENCE: 19
acacacataa ctgtgccact ataagca                                           27

<210> SEQ ID NO 20
<211> LENGTH: 7685
<212> TYPE: DNA
<213> ORGANISM: Zea mays
<220> FEATURE:
<223> OTHER INFORMATION: Zea mays ethylene receptor (ethylene response
      sensor receptor, ERS1-like), ERS14 genomic DNA

<400> SEQUENCE: 20
ttttacaaat cgttttgaat aagaattcgg atcaacacct gatattgaag ggggacgaac        60
ttgagtgatt tgactgcatg ctcgaccctt tttgatgtac tgaactcctg caatatgtct       120
aaaataccaa ggtaaagaac aacatcgtac tcctcaatgg tatccgggtt ttcaagttcc       180
gtgttcatgt cctcatgcac tttccgagct tgagctggca tattcacccc caactgtaca       240
cggaacctga aagcacaata cagaatacac atgaatcggc aacaaaatcc atctagattt       300
ttttagcaag actgagaaaa ctactctcca acaaatttct atttcaattc catcatttgg       360
gaatgggcaa acattctaat catatggaaa tattcgtgcg agtattgtcc atcaatccag       420
tggtggaaga acataaaaac agtaagagta tgatagtgat tccaatgcaa gtgtataaaa       480
```

```
tagacaaacg tataaaaatt tcaatattgt agaagtgaga ttttaaaaat cgttggataa    540
attcaacaaa tatatatcta atattttagc cgcttaaaaa aactttctac aatctcactt    600
ctacaaaaaa tattattaag agtatgtttt tttaattatt attaagagta tggttcaaaa    660
tgaaaattca ctttttttag agtatggttc aaaacgatcc ttttaggtta agtttgaata    720
agacgtgccg gacttaaaat atattatata ctaaacagta ttatagtaaa attaataata    780
attatatttt tttgagatga gtcgatcaaa cttaagatta aaaaattaaa ggaaattaaa    840
aattgaaaca tagggagtat taatttataa actgttggaa agactccaat gagtaatgtc    900
ccatcagata agaggacacc ccctgtcatc tttttggcct accttcgtcg tatctccaag    960
agtctaaatt ttattttaa aattattatc taaagaatga tttatataaa aacattttat    1020
atattttttc taatctccaa caaattttta tatcttattt gagccattaa tgtttcctat    1080
ctttgactaa caagaaacac ataatagatg atgactatat ttagataatc gtttaaataa    1140
gttgttggag tattttttt ataaaaaatc tctactcata tgaattagaa aaactttgga    1200
gttgcttatg acttttcatg ccttgtctgt agccgcatga tgcagataca atacagtatg    1260
gacacagtgc ttaactaccc cgtatgacca tatcactgca gaagatagcg ttcagatcaa    1320
gacagaaaac aagcaagacg atcttaacca aacagccgtc cactgccttt tctttctccc    1380
gttcaccccg ccgtgcacgc tcttttttgtc cctcgtgccg acgaccgacc gaccgccgcc    1440
gcctcaaggt cttcgtaaag ccactcgccg gcaacgagca gccaccaggt atgccagcac    1500
cttctcttcc attcctgctg tacgaaaccg agcacgcaaa ccctaactta agctaattgg    1560
gtatttgtat tcggatctca tctaattaca ggtgtttaca tgtattatgc ctactaacta    1620
acgctgattt tcgttaaaaa gttatcgggt gtacatgtgt acatccattt cctttactag    1680
ggccgtttgg aattgcaaat gggagttgga gcggcgaatg acatgtggca tgtcttgtgg    1740
gatttgcatg ctctgccagt acgcgtgctg cgttcatgag cttatgctat tcaaatgcca    1800
tttgctacgc atttatggct atttgggatc gggaactggc gtggcaaaaa cattttatcg    1860 atatgttttct tcttctgcag gaagatgttg tgaggactga tgcaataact aagcttgctg    1920
gatggacgga tgcgattgca tagagccact atggcctacc gatgatcttc tcgtcaagta    1980
tcagtacatc tcagacttct tcatagccct tgcgtacttc tcgattccat ggagctcat    2040 atattttgtg aagaagtcgt ccttcttccc atacagatgg gtcctgatcc agtttggtgc    2100
gtttatagtt ctttgtgggg caacccatct gataaacctg tggacgttca ccacacatac    2160
aaagaccgtt gcgatggtca tgaccatagc gaagatttct acagcagtcg tgtcctgtgc    2220
aactgctttg atgctcgttc atatcattcc cgacttgttg agcgtgaaaa ctagggagtt    2280
gttcttgaag aataaagctg aggagcttga tagagagatg ggacttataa ggacgcaaga    2340
ggagactggt agacatgtta ggatgcttac acatgaaatc agaagtactc ttgatagaca    2400
tacaattttg aagactactc tcgttgagct aggaaggacc ttgggtctgg aagaatgtgc    2460
attgtggatg ccatctcgaa gtggctcaag ccttcagctt tctcatactt tgcgccacca    2520
gattactgtt ggatcatcgg tgccaatgaa tcttcctgtc gtcaatcaag tgttcagtag    2580
caaccgggca atcataatac cccacacatc ttctttggcg cgggttcgac ctcttgcagg    2640
gcgatatgtt ccaccagaag tggccgcagt ccgtgtacct cttctacatc tttcaaactt    2700
tcaaataaat gattggcctg agctctcagc aaaaagcttt gcaatcatgg ttttgatgct    2760
tccatctgat agtgctagaa aattgcatgt gcatgaattg gagctggttg aggtcgttgc    2820
tgatcaggtt cgtgctgtat cttttgctat ggttactata acatactact tccatccaga    2880
```

```
gaaggatgta aatttacttc tgtctctatt caattcaagc tatctatact tttactaagt    2940
ttattaaaaa tattatcaat atatatatca tcggataggt gtattttgaa aatatgttcc    3000
atgacaaatc taacaacact tatttgacag tgttttttag tttttagtaa atttagtcac    3060
ggtttgactc ggtactatgc tagaattaca ttcttttccg gatggagtat atgcttgtag    3120
gagaggaaaa acatgtttac atctttcaaa atcatatgat actgctcagt gatcatgatc    3180
aattaaggca tccgttaatt gaataggaaa gtatattcac aggtgcaatg caatgatgac    3240
aagactacct tcaaatcaat acataagttc ttttttgaaa gcattggatt ctgaacccaa    3300
ctacccaaat gcaaaagaca tgtgctcttg cttgttttgc gatatctaca cctttctgaa    3360
agataaaagt ttaaatgggt attgctagca gatctattgt ttatctttt ttgtttcttc    3420
accaggtagc agttgcacta tctcatgcag ctattctcga agagtccatg cgggcacgtg    3480
atttactaat ggagcagaat gttgccctgg atttagctcg aagagaggct gagatggcta    3540
tccgtgctcg caatgatttc ctagctgtta tgaatcacga aatgagaaca cccatgaatg    3600
caataatagc cctttcctcc ttgcttttgg aaactgagct tactcctgag cagcgtctaa    3660
tggtggaaac agtactgaaa agcagcaatt tgttagcaac actcatcaat gatgttctgg    3720
atctttccaa actcgaggat ggaagccttg aactggagat taaagcattc aatcttcatg    3780
ctgttttcaa agaagtatgc accacagcta atactctttc tgctccagat tataggtcac    3840
tttagctttg ctccaagtca aactctaact ttgaccatgt ttttaaaaa aaatatctta    3900
acttccacaa atcaaataa atgcacaaac aagacatttc atggaggatt aatgaaactg    3960
attgacatta ttgttagtgt atatttctat aagtttgtcc aaagttagaa cttaggtaaa    4020
ggaagtgacc tataattggt aatagaggga gtatcaaaca tctagataca tgatgcaata    4080
gctctaattc ttatttggta ttacaggtga tgggtttcat taaaccaatt gcatctatca    4140
agaggctatc tgtatcggtt atgttggcac cagatctgcc gttatgtgca attggtgatg    4200
aaaagagact catgcaaact attctgaaca tctctggcaa tgctgtaaag tttaccaagg    4260
agggacacat cacgcttgta gcttccattg tgaaggctga ctctttgaga gagttcagaa    4320
ccccagaatt tcatccaact gcaagtgatg aacatttcta tttgaaagtt caggtgatat    4380
tctagaagag gcttgtttga ataattttcc ttgagcttgt caatgagctc atgatctttc    4440
catagtatca ataaaacaag aagatttatc tgcaaatagt tgtatgcact gttccctctt    4500
taataacaat aataacttaa aagatgacct gcatgcgttg tgcagagctc caaaattcaa    4560
aaatgaaact ggagccatcc atttggttgt cccaagtagc agttttgtaa aaccgaattg    4620
cagcctgtcg aaaaatctca actctttcat tgtacaacat ttgtaatctg ttgtcttatc    4680
tccttatgtg tgactgaatt tctcatgcac tctggttttg gatccatcca ctatgttcct    4740
cataatgaag tatttcatgc ttatttagta gcaaaagaca atatttttc ttgaaaatcc    4800
tcttaattaa cacgtgcatt ttcttgtatg aatcgttacc tattccttt aatcatgtat    4860
cttggtaatt aattgcattt gcatcattaa acctggctcg actcttgtgt tgcttgatag    4920
ttcatttgtc ttgtctataa actaggtggg tctcagctct gtataggtcc atgtacaatt    4980
ttccaattct tcctatcaag tttacaaaaa caggtggggc ctgtccagct gtacctgact    5040
atgatttggg gtgggtgggg tctgaatctt ttactttatt cttataatct catggtgtag    5100
aatttctgct ggttgggcct gatgacattt ggaatctgat tacttcttta caccattgtg    5160
acattagttg actgtcattc actgcttttt atttgagttg cctggattga attagtctca    5220
ggactgacat aggataggac ctaatatcgc attagcaaaa gctaaaatgg tctaggatta    5280
```

```
gaagtgctat accaaatctt ccatgaactc cagatagccc agagtctttt ataatgccac    5340
acacagagct ttggtatgtt gaaaaaaatc ataggtcaac cgaactaagt tatcacaaca    5400
tttactcaaa ctatatcaga attcagaagg tacagatgct tacataaatt tcattttagt    5460
tgataccacc ggtcctgggt tcatgctta caactagaaa agggttctat ttttcagat    5520 tatgaacata ccatggaaac atgaagcagg gttttacttt tatatatgct agcaattgtt    5580
atctgttgtg ttgctttaca tttctgttac ttactctttt gcaggtaaaa gatacaggct    5640
gtggagttag tcctcaggat ctacctcatg tattcacaaa gtttgctcat cctcaaagtg    5700
gaggaaaccg agggtttaat ggtagtggtc ttggccttgc catatgcaag aggtagtttg    5760
accttacagc tcctttcttg tagttccttc tgaaaattgt gttctggtgt tttttgtgac    5820
tcttgacttt ctcctacgca gcacatttat ttatttattt tatgcattgc cagtacatgg    5880
ctcattagtg ctaacctggt catcaattct tattagaact catcagcatc tctgcaaaat    5940
tctgcgcagg tttgttagtc ttatgggagg gcacatctgg atcgacagcg aaggaaccgg    6000
aagaggttgc accgcaacat tcgtcatcaa gctcggcgtg tgtgacaaca caaacaccta    6060
ccaaaagcag ctggttcctc taatctggcc aagcagtgca gactccaatt tgtctgctcc    6120
gaaagtgctg cccgacggga gaggatctgt ttccctgaaa tctcggtacc aaagaagcgt    6180
atgagctcag tgtaaatgat tgacggcata gtgccaagta ggggatcgat tagtgccatt    6240
gtctaatttt gtttgtaacc cagtcatagc aacatatagt gtacaaataa tgtaaagcca    6300
atggagactg cagctgtgta tctgggtagc aacgctgact tgctgcattg agtagtatgt    6360
cctaccagcg gattgaattg cttgttctgg ggtgtgcggc gcgcgccccg ttgattgttc    6420
tgttgtaact tgtaatccca tattaatcgt gtaatatgaa attcaatgca aatacacggt    6480
cacaagctgt tttcggtgcc ctcgctccat cagttggttc agatcgtaga tgctgccagt    6540
tgcatgtgtt agataggact ggaaaataag ctcgaggctt gcgagccggc tcgagctcga    6600
agtgtttcgc gagcctcgaa cgagtcgagc tccttctttg agctcgtttt tatagtgagc    6660
cgagccgtct cgttccagct cgcgagcctt acaaaaataa ttaatttata gaataataat    6720
gaatattaga taattttatg gataatagct catttttag ttttttgatga tgaatatatt    6780 ataatttata atttaaatta ctcataatgt tgaatgattc tttgatgatg aatatattac    6840
aatttataat ttaaattact cataatgttg aatgatgatt atatatttca aatttatata    6900
atattaattc actaaatagt gcaacaataa ataccataat atggctcgtg agccgagccg    6960
gctcgcgagc caatattgag cagagcagcc tctttcgcta gctcgtggaa tagacaagcc    7020
gagctcgttt aggcaacctc ggctcgtttt cagcccctagt cttagagttg tttggaacct    7080
ctatagctaa taattagttg ctaaaattag cttgggaggt tctaaacacc cacctctgct    7140
cggctcgttc aggcaaggtc aactcggctc gtccagtcct taattttcaa cactcaagta    7200
taattttaga tcactgaatt tgctattta ttttcttcat atatttattt tattattatt    7260 ttatttttt tcttataca cattttgggc cttaaatatt attagcacac tgatttcttg    7320
tctatctata tcttttgga catttaagc tgcaactagt aaacgggcat ccctgtacg    7380 tatggtatgg gttaggacga ccctgcttcg cttcagcgtg agtgtggcgc caattttgca    7440
tcagcgtttg ctatcatcgt cacgacgaga atgtacggtg aatatacaaa gcacaacaca    7500
acaattgtgt atatatagaa taatgagaaa aggcaacctc aacatacgat gcggacgaga    7560
aaagagcaat tgatgataga ctgatacccca ccaccagtac cacagtccac gctccttttc    7620 ttttctttt tccctccttt gtattgcaca aatcagtgag cgtgcagtcg ataaagacac    7680
```

-continued acttt                                                              7685

<210> SEQ ID NO 21
<211> LENGTH: 1902
<212> TYPE: DNA
<213> ORGANISM: Zea mays
<220> FEATURE:
<223> OTHER INFORMATION: Zea mays ethylene receptor (ethylene response
      sensor receptor, ERS1-like), ERS14 coding sequence
      (CDS)

<400> SEQUENCE: 21

```
atggacggat gcgattgcat agagccacta tggcctaccg atgatcttct cgtcaagtat      60
cagtacatct cagacttctt catagcccct gcgtacttct cgattccatt ggagctcata     120
tattttgtga agaagtcgtc cttcttccca tacagatggg tcctgatcca gtttggtgcg     180
tttatagttc tttgtggggc aacccatctg ataaacctgt ggacgttcac cacacataca     240
aagaccgttc gatggtcat gaccatagcg aagatttcta cagcagtcgt gtcctgtgca     300
actgctttga tgctcgttca tatcattccc gacttgttga gcgtgaaaac tagggagttg     360
ttcttgaaga taaagctga ggagcttgat agagagatgg gacttataag gacgcaagag     420
gagactggta gacatgttag gatgcttaca catgaaatca aagtactct tgatagacat     480
acaattttga agactactct cgttgagcta ggaaggacct gggtctgga agaatgtgca     540
ttgtggatgc catctcgaag tggctcaagc cttcagcttt ctcatacttt gcgccaccag     600
attactgttg gatcatcggt gccaatgaat cttcctgtcg tcaatcaagt gttcagtagc     660
aaccgggcaa tcataatacc ccacacatct tctttggcgc gggttcgacc tcttgcaggg     720
cgatatgttc caccagaagt ggccgcagtc cgtgtacctc ttctacatct ttcaaacttt     780
caaataaatg attggcctga gctctcagca aaaagctttg caatcatggt tttgatgctt     840
ccatctgata gtgctagaaa attgcatgtg catgaattgg agctggttga ggtcgttgct     900
gatcaggtag cagttgcact atctcatgca gctattctcg aagagtccat gcgggcacgt     960
gatttactaa tggagcagaa tgttgccctg gatttagctc gaagagaggc tgagatggct    1020
atccgtgctc gcaatgattt cctagctgtt atgaatcacg aaatgagaac acccatgaat    1080
gcaataatag cccttttcctc cttgcttttg gaaactgagc ttactcctga gcagcgtcta    1140
atggtggaaa cagtactgaa aagcagcaat tgttagcaa cactcatcaa tgatgttctg    1200
gatctttcca aactcgagga tggaagcctt gaactggaga ttaaagcatt caatcttcat    1260
gctgttttca aagaagtaat gggtttcatt aaaccaattg catctatcaa gaggctatct    1320
gtatcggtta tgttggcacc agatctgccg ttatgtgcaa ttggtgatga aaagagactc    1380
atgcaaacta ttctgaacat ctctggcaat gctgtaaagt ttaccaagga gggacacatc    1440
acgcttgtag cttccattgt gaaggctgac tctttgagag agttcagaac cccagaattt    1500
catccaactg caagtgatga acatttctat ttgaaagttc aggtaaaaga tacaggctgt    1560
ggagttagtc ctcaggatct acctcatgta ttcacaaagt ttgctcatcc tcaaagtgga    1620
ggaaaccgag ggtttaatgg tagtggtctt ggccttgcca tatgcaagag gtttgttagt    1680
cttatgggag gcacatctg atcgacagc gaaggaaccg gaagaggttg caccgcaaca    1740
ttcgtcatca agctcggcgt gtgtgacaac acaaacacct accaaaagca gctggttcct    1800
ctaatctggc caagcagtgc agactccaat ttgtctgctc cgaaagtgct gcccgacggg    1860
agaggatctg tttccctgaa atctcggtac caaagaagcg ta                       1902
```

```
<210> SEQ ID NO 22
<211> LENGTH: 634
<212> TYPE: PRT
<213> ORGANISM: Zea mays
<220> FEATURE:
<223> OTHER INFORMATION: Zea mays ethylene receptor (ethylene response
      sensor receptor, ERS1-like), ERS14 protein

<400> SEQUENCE: 22
```

Met Asp Gly Cys Asp Cys Ile Glu Pro Leu Trp Pro Thr Asp Leu
 1               5                  10                  15

Leu Val Lys Tyr Gln Tyr Ile Ser Asp Phe Phe Ile Ala Leu Ala Tyr
                20                  25                  30

Phe Ser Ile Pro Leu Glu Leu Ile Tyr Phe Val Lys Lys Ser Ser Phe
            35                  40                  45

Phe Pro Tyr Arg Trp Val Leu Ile Gln Phe Gly Ala Phe Ile Val Leu
        50                  55                  60

Cys Gly Ala Thr His Leu Ile Asn Leu Trp Thr Phe Thr Thr His Thr
65                  70                  75                  80

Lys Thr Val Ala Met Val Met Thr Ile Ala Lys Ile Ser Thr Ala Val
                85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Glu Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Gly Leu
                165                 170                 175

Glu Glu Cys Ala Leu Trp Met Pro Ser Arg Ser Gly Ser Ser Leu Gln
            180                 185                 190

Leu Ser His Thr Leu Arg His Gln Ile Thr Val Gly Ser Ser Val Pro
        195                 200                 205

Met Asn Leu Pro Val Val Asn Gln Val Phe Ser Ser Asn Arg Ala Ile
    210                 215                 220

Ile Ile Pro His Thr Ser Ser Leu Ala Arg Val Arg Pro Leu Ala Gly
225                 230                 235                 240

Arg Tyr Val Pro Pro Glu Val Ala Ala Val Arg Val Pro Leu Leu His
                245                 250                 255

Leu Ser Asn Phe Gln Ile Asn Asp Trp Pro Glu Leu Ser Ala Lys Ser
            260                 265                 270

Phe Ala Ile Met Val Leu Met Leu Pro Ser Asp Ser Ala Arg Lys Leu
        275                 280                 285

His Val His Glu Leu Glu Leu Val Glu Val Ala Asp Gln Val Ala
    290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Glu
                325                 330                 335

Ala Glu Met Ala Ile Arg Ala Arg Asn Asp Phe Leu Ala Val Met Asn
            340                 345                 350

His Glu Met Arg Thr Pro Met Asn Ala Ile Ile Ala Leu Ser Ser Leu
        355                 360                 365

Leu Leu Glu Thr Glu Leu Thr Pro Glu Gln Arg Leu Met Val Glu Thr

```
                     370                 375                 380
Val Leu Lys Ser Ser Asn Leu Ala Thr Leu Ile Asn Asp Val Leu
385                 390                 395                 400

Asp Leu Ser Lys Leu Glu Asp Gly Ser Leu Glu Leu Glu Ile Lys Ala
                405                 410                 415

Phe Asn Leu His Ala Val Phe Lys Glu Val Met Gly Phe Ile Lys Pro
                420                 425                 430

Ile Ala Ser Ile Lys Arg Leu Ser Val Ser Val Met Leu Ala Pro Asp
                435                 440                 445

Leu Pro Leu Cys Ala Ile Gly Asp Glu Lys Arg Leu Met Gln Thr Ile
            450                 455                 460

Leu Asn Ile Ser Gly Asn Ala Val Lys Phe Thr Lys Glu Gly His Ile
465                 470                 475                 480

Thr Leu Val Ala Ser Ile Val Lys Ala Asp Ser Leu Arg Glu Phe Arg
                485                 490                 495

Thr Pro Glu Phe His Pro Thr Ala Ser Asp Glu His Phe Tyr Leu Lys
                500                 505                 510

Val Gln Val Lys Asp Thr Gly Cys Gly Val Ser Pro Gln Asp Leu Pro
                515                 520                 525

His Val Phe Thr Lys Phe Ala His Pro Gln Ser Gly Gly Asn Arg Gly
            530                 535                 540

Phe Asn Gly Ser Gly Leu Gly Leu Ala Ile Cys Lys Arg Phe Val Ser
545                 550                 555                 560

Leu Met Gly Gly His Ile Trp Ile Asp Ser Glu Gly Thr Gly Arg Gly
                565                 570                 575

Cys Thr Ala Thr Phe Val Ile Lys Leu Gly Val Cys Asp Asn Thr Asn
                580                 585                 590

Thr Tyr Gln Lys Gln Leu Val Pro Leu Ile Trp Pro Ser Ser Ala Asp
                595                 600                 605

Ser Asn Leu Ser Ala Pro Lys Val Leu Pro Asp Gly Arg Gly Ser Val
            610                 615                 620

Ser Leu Lys Ser Arg Tyr Gln Arg Ser Val
625                 630

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence:Zea mays
      ethylene receptor (ethylene response sensor
      receptor, ERS1-like, ZmERS14) forward primer

<400> SEQUENCE: 23
gagttagtcc tcaggatcta cctcatgt                                       28

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:Zea mays
      ethylene receptor (ethylene response sensor
      receptor, ERS1-like, ZmERS14) reverse primer

<400> SEQUENCE: 24
caactcaatc cgctggtagg acatact                                        27

<210> SEQ ID NO 25
```

<211> LENGTH: 6378
<212> TYPE: DNA
<213> ORGANISM: Zea mays
<220> FEATURE:
<223> OTHER INFORMATION: Zea mays ethylene receptor (ethylene response
      sensor receptor, ERS1-like), ERS25 genomic DNA

<400> SEQUENCE: 25

```
gacgccgagt tcgatgtgga catccatcgc tcggtggacg accacgatat ccatagcgtg      60
ctggactacc gccgtctgcg cgaggccatc gtcgaggaat gcacgcaggc gcatgtgaac     120
ctgatcgaaa ccctgtccga acaagtcgcc gcgcgcctgt tggccgactt ccaggaaatc     180
cgctcgttgc gcttgcgcat cagcaagccc atggcctttt ccgactgcgc ggcggtaggc     240
gtggaaatcc agatcacccg ctgaccatga acgatattgc tccgcccccc gccgtccgct     300
cccccgaggt ccgctatcgc accgaggccg aggaaaaggc ccgccacgaa ggcaacaagc     360
tgaccaagcg cctggcccgc gaaaccacgc gcgcgctgtc cgactacaac atgattgaag     420
aaggcgaccg cgtgatggtc tgcctgtcgg gcggcaagga ttcctatgcc atgctggaca     480
tcctgctgca attgcagaag cgcgcgccgt tcaagtttga actgatcgcc gtcaacctgg     540
accagaagca gccgggcttt cccgaccaca tcctgcccca gtacctgaaa gacctgggcg     600
tgcccttcca catcgagacg caggacacgt attccatcgt cacgcgcgtg ctggaagaag     660
gcaagacgat gtgctcgctc tgttcgcgct tgcgtcgcgg cattctgtac cgcgtcgcct     720
cggaactggg cgccaccaag atcgcgctgg ccaccaccg cgacgacatc ctggccacgt     780
tcttcctgaa cctgttctat ggcggcaagg ccaagggcat gccgcccaaa ctggtgtcgg     840
acgacggccg ccacaccgtg atccgtccgc tggcctatgt ggccgaaacg gacctgatcg     900
cctatgcgga gttgaagcaa ttccccatca ttccgtgcaa cctctgcggc tcgcaggaaa     960
acctgaagcg caaggaagtg ggccggatga tctatatata gtcttagggt tgtcatgcga    1020
cctagcaaat aaagaggatg actctggtca ggaacggata taaagcatcg ggccacctcg    1080
ttcgtggctt aatccatatt tttttattta tatttgttat ctttagacta aaatgtattg    1140
gacttttttt tgcttgatcg gatgggattt ttttcatgt cgtggttgtg gtcgcatgaa    1200
gtcatgaaga tgcttgctgg catgttgctg ttgggtagcc catctctgca tgccattgcc    1260
cactcttaca gaactgtagt aacaacagca gctggtgtag agtagctgca gtgagccagt    1320
gaacgcaatg cttagacgac ttacagaaca gcgccggact gccttcaccc tgcctattct    1380
ttcttcccgt tcaccccgcg tgcacgctct ttcccttcct cgtgccgacg accgggcgac    1440
cgccgcgccc cggcccgcgc ccccttgtct cgggccactc gccggcaacg agcagccacc    1500
aggtatgcca ccccttctc cccccttcct gctgtacgaa accgagcacc caaaccctaa    1560
cttaagctta tttggctatt tacattcgga tctgatctag ttacaggagc acacgtat     1620 tatccctact aaatccgatt ttagtggaaa aagctgtcgg gtgtacatgt gtccaccat    1680 gtcctttacg agttcggccc ttggccgagg tccgtttgga attggaaatg ggaatcagag    1740
gggcgaatgc cgaatgggca tgtcttgcgc aatttccatg ctctgctagt aggcgtgctg    1800
cgttcatgag ctcatactat ccaaatgcca ttcgctacgc atttgcttct atttgagatc    1860
gggaaacggt gtgtcaaaaa cgatttatca atatgtttct tcttctacag gaaatgttgt    1920
gaggactgat gcaataacta agcttgctgg atggacggat gtgattgcat cgagccacta    1980
tggcctaccg atgatctcct tgtcaagtat cagtacatct cagacttctt catagccctc    2040
gcgtacttct ctattccgtt ggagctcata tatttcgtga agaagtcgtc cttcttcccg    2100
tacagatggg tcttgatcca gtttggtgcg tttatagttc tctgtggggc aacccatctg    2160
```

```
ataaacctgt ggacgttcac cacacataca aagaccgttg cgatggtcat gaccatagca    2220
aaggtttcta cagcagttgt gtcctgtgca actgctttga tgcttgttca tatcatcccc    2280
gacttattga gcgtgaaaac tagagagttg ttcctgaaga ataaagctga agagcttgac    2340
agagagatgg gactgataag gacgcaggag gagaccggta gacatgttag gatgcttaca    2400
catgaaatca gaagtactct tgacaggcat atgattttga agactactct tgttgagcta    2460
ggaaggacct tgggtctgga ggaatgtgca ttgtggatgc catctcgaag tggttcaagc    2520
cttcagcttt ctcatacttt gcaccaccag attactgttg gatcatcggt gccaattaat    2580
cttcctgtca tcaatcaagt gttcagtagc aaccgggcaa ttataatacc ccacacatct    2640
cctttggcgc ggattcgacc tcttacaggg cgatatgttc caccagaagt ggctgcagtc    2700
cgtgtacctc ttctccacct ttcaaacttc caaataaatg attggcctga gctttcggca    2760
aaaagctttg caatcatggt tttgatgctt ccatctgata gtgcaagaaa atggcatgta    2820
catgaattgg agctggttga ggttgttgct gatcaggttc gtgctgtatc tctgtctatg    2880
gttactataa catggtacct tcatcctgaa aatgatgtaa atttacttgt ctctattcaa    2940
acaatctata ctttgattaa gtttattaaa agattatcaa taaatatgac atcagatagg    3000
tatattttga aaatatattc catgacatat ttaacaatac ttatttgata gtgtaaatat    3060 tgctatttt aaataaattt ggtcactgtt ttacttggcg ctatgctaga attacattct    3120
tttctggatg gagggagtat atgcttgtag gagaggaaaa acatgtttac atctttcaaa    3180
ttcatatgat actgctcagt tatcatgatc agtcaattaa ggcatccgtt aattgaacag    3240
gaaagtatat tcacaggtgc aatgtaatga tgacaagaat acctttaaat caatacataa    3300
tctctttttt tgaaagcata ggattctgaa cccaactacc gagccacaaa agacacatgc    3360
tcttgctgtt gcgcaatatc tacacctttc tgaaggttaa agtttaaat tggtagtgct    3420 agcaggtcta ttgtttatct cctttttttg tttcttcatc aggtagcagt tgcactatct    3480
catgcggcta ttcttgaaga gtccatgcga gcacgtgatt tactaatgga gcagaatgtt    3540
gccctggatt tagctcgaag agaggctgag atggctatcc gtgctcgcaa tgattttcta    3600
gctgttatga atcacgaaat gagaacaccc atgaatgcaa taatagccct ttcctccttg    3660
cttttggaaa ctgagcttac tcctgagcag cgtctaatgg tggaaacagt actgaaaagc    3720
agcaatctgt tagcaacact catcaatgat gtgctagatc tttccaaact cgaggatgga    3780
agccttgaac tggagattaa agcattcaat cttcatgctg ttttcaaaga agtatgcacc    3840
atcagttttc taatactctt tccgttccag gttctaggtt actttagctt tgctctaagt    3900
caaactctaa ctttggccaa gttttagaaa aaatatgtca acttctacaa attaaaataa    3960
atgcactaac aagacatgtt atggagaatt catgtgatgt tattgttggt gtatttttct    4020
ataagtttgt tcaaagttag agaaattgga cttaggtaaa gaaagcgact tgtaattagt    4080
aacagaggga gtatcaaaca tctagataca cggtgcaaca actaaaattc ctatttggta    4140
ttacaggtga tgggtttcat taaaccaatt gcatctatca agaggctatc tgtatcggtt    4200
atgttggcac cagatttgcc gttatgtgcc attggtgatg aaaagagact catgcaaact    4260
attctgaaca tctctggcaa cgctgtaaag tttaccaagg agggacacat cacacttgta    4320
gcttccattg tgaaggctga ctcttgaga gagttcagaa ccccagaatt tcatccaact    4380
gcaagtgatg accatttcta tttgaaagtt caggtaatat tctagaaagg cttgtttgaa    4440
taatcttgga cttgtcaatg agctcatggt cttttccatc tatcaataaa acaaatagaa    4500
ttttttgcaa atggttgtat gcattgtccc tctttaataa caataataac ttaaaaaatg    4560
```

```
acctgtatgt gttgtgcaga gcaccaaatt tcaaaaatga aactggagcc atccatttgg    4620
ttgtctcaag tagcagttta gtgaaccta attgcagctt gtcaaacaat ctcaactatt    4680
tcattgtaca acatttataa tctgttgtct tgtcttctta tttgcgactg aatttctcat    4740
gcactctggt tctggattca ctgtgttcct cacattgaag tatttcatgc ttattcagta    4800
gtagatgata ttttttcat gaaaatcctc ttgattaata tctgcgtttc cttgtatgat    4860
ttgttacata tttcctttaa ttatgcgtct tggtcattaa ttgcatatgc atcataactt    4920
ggatagaccc ttaagttgtt tgatagtcca tttgtttata aactatgtgg tcgtcagctc    4980
tgtataggtc catgtacaat tttccaattc tttgtaccaa gtttacaaaa gcagacggta    5040
cctgttcaga tgtacctgac tgatgtgtgt gtgtgtgggg gggggagggg gtctgaatcc    5100
ttttctttgt tataatctca aggagtcaag gtggtgtgga atttctacca gtgttgggca    5160
tgatgatttt tggaatccga tttctttacg ccactgtgac cttagttcag tagtcatttg    5220
ttgcgtttta tctgagttgc ctggattgaa ttagtcgcag gactgacata ggactaggac    5280
ctaaggccgc attagcaaaa actcagatgg tctaggatcc gttgacctgc aggtcgaccc    5340
agatcataag tgttatacca aatcttccat gagctccaga tcagccctga tccttgtata    5400
atgctaacac aaagctttcg tgtgttgaaa acattccta ggtcaaccat attaagttat    5460
cacaacgttt actcaatata tcacaaggcg cagatgctta tatttgcaga ttatgaacat    5520
gccatggaca aacgaagcag agttttactt ctatgcttag caagtcttat ctattgtgtt    5580
gctttacatt ctctgttact tcacacttct gcaggtaaaa gatacaggct gtggaattgg    5640
tccacaggat ctacctcatg tatttacaaa gtttgctcat cctcaaagcg gaggaaaccg    5700 agggttaat ggtagtggtc ttggccttgc catatgcaag aggtagttcg atcttacatc    5760
tcctttctgt agttccttct gaatctggtg ttaaggtgct gttttggtg actcgaagtc    5820 ttcctatgca gcacaattat ttatttattt tgtttaatgc attgccagta tagggata    5880 cctcggtcat caattctcat tagaactcat cggcatctct gcaaatttct ggtgcaggtt    5940
tgttagtctc atgggagggc acatctggat tgacagcgaa ggaaccggaa gaggttgcac    6000
cgcaacattc gtcgtcaagc tcggcgtgtg tgacaacaca aacacctacc agcagcagct    6060
gatccctcta gtatggccaa gcagcgcaga ctccgatttg cgtgctccga aacctcttcc    6120
ggacgggaga ggatctactc ccttgaaatc tcggtaccaa aggagcgtat gagcctagtg    6180
taaatgattg acggcatagt gccaagtagg ggaccgatta gtgccaccgt ctaattttgt    6240 ttgtaacct gtcatagcag gcatatgatg tacaaatact gtaaagcaaa tggagactgc    6300
ggccgtgtat ctgggtggca acgctgactt gctgcattga gtggtatata catatgctac    6360
cagcggattg aattgctt                                                  6378
```

<210> SEQ ID NO 26
<211> LENGTH: 1905
<212> TYPE: DNA
<213> ORGANISM: Zea mays
<220> FEATURE:
<223> OTHER INFORMATION: Zea mays ethylene receptor (ethylene response sensor receptor, ERS1-like), ERS25 coding sequence (CDS)

<400> SEQUENCE: 26

```
atggacggat gtgattgcat cgagccacta tggcctaccg atgatctcct tgtcaagtat     60
cagtacatct cagacttctt catagccctc gcgtacttct ctattccgtt ggagctcata    120
tatttcgtga agaagtcgtc cttcttcccg tacagatggg tcttgatcca gtttggtgcg    180
```

```
tttatagttc tctgtggggc aacccatctg ataaacctgt ggacgttcac cacacataca      240
aagaccgttg cgatggtcat gaccatagca aaggtttcta cagcagttgt gtcctgtgca      300
actgctttga tgcttgttca tatcatcccc gacttattga gcgtgaaaac tagagagttg      360
ttcctgaaga ataaagctga agagcttgac agagagatgg gactgataag gacgcaggag      420
gagaccggta gacatgttag gatgcttaca catgaaatca gaagtactct tgacaggcat      480
atgattttga agactactct tgttgagcta ggaaggacct tgggtctgga ggaatgtgca      540
ttgtggatgc catctcgaag tggttcaagc cttcagcttt ctcatacttt gcaccaccag      600
attactgttg gatcatcggt gccaattaat cttcctgtca tcaatcaagt gttcagtagc      660
aaccgggcaa ttataatacc ccacacatct cctttggcgc ggattcgacc tcttacaggg      720
cgatatgttc caccagaagt ggctgcagtc cgtgtacctc ttctccacct ttcaaacttc      780
caaataaatg attggcctga gctttcggca aaaagctttg caatcatggt tttgatgctt      840
ccatctgata gtgcaagaaa atggcatgta catgaattgg agctggttga ggttgttgct      900
gatcaggtag cagttgcact atctcatgcg gctattcttg aagagtccat gcgagcacgt      960
gatttactaa tggagcagaa tgttgccctg gatttagctc gaagagaggc tgagatggct     1020
atccgtgctc gcaatgattt tctagctgtt atgaatcacg aaatgagaac acccatgaat     1080
gcaataatag ccctttcctc cttgcttttg gaaactgagc ttactcctga gcagcgtcta     1140
atggtggaaa cagtactgaa aagcagcaat ctgttagcaa cactcatcaa tgatgtgcta     1200
gatctttcca aactcgagga tggaagcctt gaactggaga ttaaagcatt caatcttcat     1260
gctgttttca aagaagtaat gggtttcatt aaaccaattg catctatcaa gaggctatct     1320
gtatcggtta tgttggcacc agatttgccg ttatgtgcca ttggtgatga aaagagactc     1380
atgcaaacta ttctgaacat ctctggcaac gctgtaaagt ttaccaagga gggacacatc     1440
acacttgtag cttccattgt gaaggctgac tctttgagag agttcagaac cccagaattt     1500
catccaactg caagtgatga ccatttctat ttgaaagttc aggtagtaaa agatacaggc     1560
tgtggaattg gtccacagga tctacctcat gtatttacaa agtttgctca tcctcaaagc     1620
ggaggaaacc gagggtttaa tggtagtggt cttggccttg ccatatgcaa gaggtttgtt     1680
agtctcatgg gagggcacat ctggattgac agcgaaggaa ccggaagagg ttgcaccgca     1740
acattcgtcg tcaagctcgg cgtgtgtgac aacacaaaca cctaccagca gcagctgatc     1800
cctctagtat ggccaagcag cgcagactcc gatttgcgtg ctccgaaacc tcttccggac     1860
gggagaggat ctactcccttgaaatctcgg taccaaagga gcgta                      1905
```

<210> SEQ ID NO 27
<211> LENGTH: 634
<212> TYPE: PRT
<213> ORGANISM: Zea mays
<220> FEATURE:
<223> OTHER INFORMATION: Zea mays ethylene receptor (ethylene response
       sensor receptor, ERS1-like), ERS25 protein

<400> SEQUENCE: 27

Met Asp Gly Cys Asp Cys Ile Glu Pro Leu Trp Pro Thr Asp Asp Leu
1               5                   10                  15

Leu Val Lys Tyr Gln Tyr Ile Ser Asp Phe Phe Ile Ala Leu Ala Tyr
                20                  25                  30

Phe Ser Ile Pro Leu Glu Leu Ile Tyr Phe Val Lys Lys Ser Ser Phe
            35                  40                  45

Phe Pro Tyr Arg Trp Val Leu Ile Gln Phe Gly Ala Phe Ile Val Leu

-continued

```
                50                  55                  60
Cys Gly Ala Thr His Leu Ile Asn Leu Trp Thr Phe Thr Thr His Thr
 65                  70                  75                  80

Lys Thr Val Ala Met Val Met Thr Ile Ala Lys Val Ser Thr Ala Val
                 85                  90                  95

Val Ser Cys Ala Thr Ala Leu Met Leu Val His Ile Ile Pro Asp Leu
                100                 105                 110

Leu Ser Val Lys Thr Arg Glu Leu Phe Leu Lys Asn Lys Ala Glu Glu
                115                 120                 125

Leu Asp Arg Glu Met Gly Leu Ile Arg Thr Gln Glu Glu Thr Gly Arg
130                 135                 140

His Val Arg Met Leu Thr His Glu Ile Arg Ser Thr Leu Asp Arg His
145                 150                 155                 160

Met Ile Leu Lys Thr Thr Leu Val Glu Leu Gly Arg Thr Leu Gly Leu
                165                 170                 175

Glu Glu Cys Ala Leu Trp Met Pro Ser Arg Ser Gly Ser Ser Leu Gln
                180                 185                 190

Leu Ser His Thr Leu His His Gln Ile Thr Val Gly Ser Ser Val Pro
                195                 200                 205

Ile Asn Leu Pro Val Ile Asn Gln Val Phe Ser Ser Asn Arg Ala Ile
210                 215                 220

Ile Ile Pro His Thr Ser Pro Leu Ala Arg Ile Arg Pro Leu Thr Gly
225                 230                 235                 240

Arg Tyr Val Pro Pro Glu Val Ala Ala Val Arg Val Pro Leu Leu His
                245                 250                 255

Leu Ser Asn Phe Gln Ile Asn Asp Trp Pro Glu Leu Ser Ala Lys Ser
                260                 265                 270

Phe Ala Ile Met Val Leu Met Leu Pro Ser Asp Ser Ala Arg Lys Trp
                275                 280                 285

His Val His Glu Leu Glu Leu Val Glu Val Ala Asp Gln Val Ala
290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Met Ala Ile Arg Ala Arg Asn Asp Phe Leu Ala Val Met Asn
                340                 345                 350

His Glu Met Arg Thr Pro Met Asn Ala Ile Ile Ala Leu Ser Ser Leu
                355                 360                 365

Leu Leu Glu Thr Glu Leu Thr Pro Glu Gln Arg Leu Met Val Glu Thr
370                 375                 380

Val Leu Lys Ser Ser Asn Leu Leu Ala Thr Leu Ile Asn Asp Val Leu
385                 390                 395                 400

Asp Leu Ser Lys Leu Glu Asp Gly Ser Leu Glu Leu Glu Ile Lys Ala
                405                 410                 415

Phe Asn Leu His Ala Val Phe Lys Glu Val Met Gly Phe Ile Lys Pro
                420                 425                 430

Ile Ala Ser Ile Lys Arg Leu Ser Val Ser Val Met Leu Ala Pro Asp
                435                 440                 445

Leu Pro Leu Cys Ala Ile Gly Asp Glu Lys Arg Leu Met Gln Thr Ile
                450                 455                 460

Leu Asn Ile Ser Gly Asn Ala Val Lys Phe Thr Lys Glu Gly His Ile
465                 470                 475                 480
```

```
Thr Leu Val Ala Ser Ile Val Lys Ala Asp Ser Leu Arg Glu Phe Arg
                485                 490                 495
Thr Pro Glu Phe His Pro Thr Ala Ser Asp Asp His Phe Tyr Leu Lys
            500                 505                 510
Val Gln Val Lys Asp Thr Gly Cys Gly Ile Gly Pro Gln Asp Leu Pro
        515                 520                 525
His Val Phe Thr Lys Phe Ala His Pro Gln Ser Gly Gly Asn Arg Gly
    530                 535                 540
Phe Asn Gly Ser Gly Leu Gly Leu Ala Ile Cys Lys Arg Phe Val Ser
545                 550                 555                 560
Leu Met Gly Gly His Ile Trp Ile Asp Ser Glu Gly Thr Gly Arg Gly
                565                 570                 575
Cys Thr Ala Thr Phe Val Val Lys Leu Gly Val Cys Asp Asn Thr Asn
            580                 585                 590
Thr Tyr Gln Gln Gln Leu Ile Pro Leu Val Trp Pro Ser Ser Ala Asp
        595                 600                 605
Ser Asp Leu Arg Ala Pro Lys Pro Leu Pro Asp Gly Arg Gly Ser Thr
    610                 615                 620
Pro Leu Lys Ser Arg Tyr Gln Arg Ser Val
625                 630

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence:Zea mays
      ethylene receptor (ethylene response sensor
      receptor, ERS1-like, ZmERS25) forward primer

<400> SEQUENCE: 28
gagttagtcc tcaggatcta cctcatgt                                        28

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:Zea mays
      ethylene receptor (ethylene response sensor
      receptor, ERS1-like, ZmERS25) reverse primer

<400> SEQUENCE: 29
caattcaatc cgctggtagc atatgt                                          26

<210> SEQ ID NO 30
<211> LENGTH: 5707
<212> TYPE: DNA
<213> ORGANISM: Zea mays
<220> FEATURE:
<223> OTHER INFORMATION: Zea mays ethylene receptor (ethylene resistant
      receptor, ETR2-like), ETR9 genomic DNA

<400> SEQUENCE: 30
tatacaccac agcaaaatgg tgtggtagag aggaagaaca ggacgctgat cgacatggcg      60
agaatgatgc ttggagagtt caagacgccc gagcggtttt tgtcggaaga tgtgaacaca     120
gcctgccatg ccataaacca gctctatctg catcgtctcc tcaagaagac ctcctacgaa     180
ctccttatcg gtaacaaacc caatgtctct tactttcgtg tatttgggag caaatgctac     240
attctggtga agaaaggtag acattctaaa tttgctccca agcagtagaa agggttctta     300
ctagggtatg actcaaatac aaaggcgtat agagtcttca acaaatcatc gggattagtt     360
```

-continued

```
gaagtctcta gcgacattgt atttgatgag actaatggct ctccaagaga gcaagttgat    420
cttgatgatg tagatgaaga agaaataacg acgaccgcaa tgcgcacgat ggcgataggc    480
gatgtgcgac cacaggaact acaggaacaa gataaaccat cttcctcgac aatggtgcat    540
cccccaactc aagacgttga acaagtacat caagaagagg ggcaagatca aggggagca     600 caagaagaac aggttatgga ggaagaagca ccatgggccc cttcaactca gtccgagca     660 acgatccaaa gacatcaccc cgtcgatcaa attctgggtg acatcatcaa gggagtaact    720
actcgctcac gtttagctaa tttttgtgag cattactcgt tggtctcttc tattgagcct    780
ttcagggtag aagaggcctt gcaggatccg gactgggtgt tggccatgca ggaagagctc    840
aacaacttca agagaaatga agtctggagc ctggtgccac gtccaaagca aaatgttgtg    900
ggaaccaagt gggtgttccg gaacaagcaa gatgagcacg gggtggtgac aagaaacaag    960
gctcgacttg tggcaaaagg ttatgcccaa gtcgcaggtt tggatttcga ggagactttt   1020
gctcatgttg ctaggctaga gtcaattagg attttattag cctatgctgc tcaccactct   1080
tttaggctgt tccaaatgga cgtgaagagc gctttcctca acgggccaat taaggaggag   1140
gtatacgtgg aacaaccctc tggctttaag gatgacaggt atcatgacca tgtgtataag   1200
ctctctaagg cgctctatgg acttaagcaa gccccaagag catggtatga atgccttaga   1260
gatttcttaa ttgctaatgc cttcaaggtt gggaaagctg atcccactct ttttaccaag   1320
acttgtgatg gtgatctctt tgtgtgccaa atttatgtcg atgacataat atttggttct   1380
actaatcaaa gtcttgtga ggagtttagc agggtgatga tgcaaaagtt cgagatgtcg    1440
atgatgggcg agttgaccta cttccttggg ttccaagtga agcaactcaa agacggcaca   1500
ttcatctccc aaatgaagta cactcaggtc ttctcaagag gtttgggatg aaggacgcca   1560
agcccgcgaa gacactaatg ggaactgacg ggcatattga cctcaacaaa ggaggtaagt   1620
ccgttgatcc gtagccagcc cacgtgtaga cggttatggt gctagtaccg gtgccaacgc   1680
tgtgtttctt ggcgggcgtt gctgctcctc ctccgcttga ggattgctgc tgcatccggc   1740
aggagggatg gtcggaggcg aaggtgggc ggcttttgac actcctccgt tcttcttcgt    1800
tctaccaatt caataactat gtttggattt atcggagggg tttatcggat tggctaaat    1860 cccctactgc ccgaattttg gcggactggt gattcgattt tggccgatag atagatttcg   1920
atgctacttt taggaaagac taatcttcac aggggggcct atccgtccca aagcaacgat   1980
ttgctttacg ccagatcttg attttgtgtg ccgcagtttg attaactgaa aatctgtgat   2040
ggccgtctgg tgaatgcagg agcgtcggca cccgcagcgt ggaatcgacg acgggcgcct   2100
ccagtcggtt cagaaatgcg caaatgcgcg tctgaatgaa gcctggttgg aggtggtaga   2160
cccgatggtg gtgggaacgg cactgctgcg cggggtttcc tccgcgtgga tcctcctgtt   2220
cctctcctcc ctgctcctct cgccgtcagc ggcgtctgtc gatttcggcc actgcggcgg   2280
ctgcgacgac gccgacgacg gcgccctctc cagcacctat aacatcctgc aatgccagaa   2340
ggtcagcgac ttcctcatcg ccgcggccta cttctccatc ccgctcgagc tgctctactt   2400
cgccacctgc tccgacctct tcccctcaa atggatcgtc ctgcagttcg gcgccttcat    2460
cgtgctctgc ggcctcacgc acctcatcac tgtgttcacc tacgagccgc actccttcca   2520
cctcgtactc gcccttaccg tcgccaagtt cctgacggca ctggtctcct tcgcgacggc   2580
catcaccctg ctgacgctga taccacagct cctgagggtg aaggtcaggg aaaacttcct   2640
gatgaacaag gcgcgtgagc tggacccggga ggtggggagg atgaaaagga agaagaggc   2700 gagctggcat gtgcgcatgc tcacacagga gatccgcaag tcgctcgaca gacataccat   2760
```

```
cttgtacacc accatggttg agctctcgaa ggcactggaa ctgcagaatt gtgctgtctg    2820
gatgcctgat gagaccagga gcacgatgat cttaacacat cagctgaggg aaagggatat    2880
aatggaccca cagaaacact cgattcctat tgatgatccg gatgttcaag aaataaaggc    2940
aaccaaggat gcaaaagttc ttggcccaga ttcggcgcta ggggtttcta gccgaagcaa    3000
gcatgaagca gggcctgtgg ctgcaataag gatgccgatg ttaagggtgt caaatttcaa    3060
aggagggact ccggaagtga tgcagacgag ctatgctatc ttggttctgg ttttgcctaa    3120
tgatggttca ttagggtggg gtcgaagaga gttggagatt gttgaggtag ttgctgacca    3180
agttgcagtc gctctgtcac atgctgcact cctagaggag tctcagctga tgcgagagaa    3240
gcttgccgag cagcataggg acttgctgca ggcaaaggat gaagccatga gggcagggga    3300
cgctaggaat tccttccaga ctgcaatgta cgatggaatg cgaaggccaa tgcactcaat    3360
ccttggtctc gtctcaatga tgcaacagga gagcatgaat ccagagcaaa ggcttgtgat    3420
ggatgccatt gccaagacaa gcagtgttgc atccacactg atgaacgatg tgatgcaaac    3480
atcgacaatg aactgtgagc acttgtcttt ggtcaggagg ccgttcaacc ttcattcctt    3540
cattaaagaa gttgttggag tggtcagatg tctaactggt tgcaagggtg tggagtttga    3600
gtttcaagtg gagaattctt tgccagaaag gatcattggt gatgagaaga gagtcttcca    3660
tattgtcctg cacatggtag gcactctaac agaccgatgt aatgctggct gtatctcatt    3720
atatgtaaat gtccataatg aggttgaaga taggcataat catgactgga tgctgcgaag    3780
agcaaacttc tctgggggct atgtatgtgt gaaatttgag attaggatta gaaaatcaaa    3840
gggctatctg ttgagttcat caagcagtca gataagtcag ggatccaaac ccaacaattc    3900
tgagatgggg cttagcttca atatgtgcaa gaagattgtg caggtaaatc aaaataatag    3960
aatatcttaa gcatttatac ccgcaaattt ttttgtacag ctaggcacta gcagcttaga    4020
cttggccgtc acatagatag tttgctatac accaattgaa ctgccaaact acagaatgtg    4080
tttagtggct atagtgtggc cttttgtgc aagtgcttgg aatatttatt atctcacctc     4140
aaactgggca tactgagagg acatattggt ccttatgttg aacttacgtt ttagtcataa    4200
ctatttttat ggtatttctt ccgtagtatg tgtgacttgc atagatatat ttaattggta    4260
tgcttgtagt agcccgaacc tcagcgactc tatttgattg ttatgttttg gtttgcaatt    4320
tgttcatcca gttgtggaag tggccaatgt atacttgatt tgatgtgcaa tcattagtgt    4380
gcttactgat acgagccctc ctttgtgctg cagatgatga atggcaatat ttggtcagta    4440
tcagattcta aaagcatcgg agaaactatc atgctagtcc tccagttcca gttggaacct    4500
gtgactccgg tctctggagc gtcctcagat ttgtacagat catccgcaat tcccaacttt    4560
aatgggctca gagtcctcct tgcggacagc gactgcacca accgagctgt aactcacagg    4620
ctcctagaga agcttggttg ccgagtcctt tcggtcgctt ctggcgtcca atgcatcagc    4680
tccttcgctg cggagtcgtc cttccagctg gtggttcttg atcttgacat gcagacgatg    4740
gatggattcg aagtagcccg cgcgatcagg aagttcagta gcaatagttg gctgccgttg    4800
attattgccc tagcagcaag aatcgacgac aacatccggg atcgttgcca gaggtcagga    4860
gtaaatggcc tgatccagaa accggtcaca ttagccgcgc tgggagatga actgtataga    4920
gtccttcaga acaattaaaa gagcctgacg gttctcattt ctttcaatct caatagattg    4980
ctatagcttg atcggtaact aatttctgcc aggttagctc catacaatca caaaaaaaa     5040 aacatttga ggcaaagggg aaatgtatag gaagctgaaa gcatcgcttt ctgcttggtt     5100
cctcggtgaa ggaggaggag gacgactacg acaggaaggt acaaaaaact tggagagatc    5160
```

```
atactgttag aacttagacc cattcatctg taaaccctca gataagcaaa gaattagatt    5220
catgcactaa cactaaccac gatataatta gtttggacga aatccatgag ctgttgagtt    5280
tgtgattggg actcagaatg gatgggggtt cagtgaatgc agcggcatat gtgtctacag    5340
gggggaaaaa ggaacttttg ttattggtta gacatgctgc aaaagcaggc tggatgagat    5400
tgcagacaag aaggcagacg atgcggctga tgctgacctt ttttacatta cagacttggg    5460
ctggttctgg tcagcgaacc cttgcttgct tatacgatat cctctgttcc ttacacgata    5520
tccttctaga aacactttaa gatataaact agttttttt aagcacgtta gcatcagtgg    5580
aacagtttgg gtagtaaaaa tctggtgcat tggcacctaa gcttctttgg tcacctcaag    5640
agctctcaac aatcagagcg attgtctaat gagaatccac ggccagattt ggtgttttga    5700
cccggtt                                                              5707
```

<210> SEQ ID NO 31
<211> LENGTH: 2301
<212> TYPE: DNA
<213> ORGANISM: Zea mays
<220> FEATURE:
<223> OTHER INFORMATION: Zea mays ethylene receptor (ethylene resistant
      receptor, ETR2-like), ETR9 coding sequence (CDS)

<400> SEQUENCE: 31

```
atggtggtgg gaacggcact gctgcgcggg gtttcctccg cgtggatcct cctgttcctc      60
tcctccctgc tcctctcgcc gtcagcggcg tctgtcgatt tcggccactg cggcggctgc     120
gacgacgccg acgacggcgc cctctccagc acctataaca tcctgcaatg ccagaaggtc     180
agcgacttcc tcatcgccgc ggcctacttc tccatcccgc tcgagctgct ctacttcgcc     240
acctgctccg acctcttccc cctcaaatgg atcgtgctgc agttcggcgc cttcatcgtg     300
ctctgcggcc tcacgcacct catcactgtg ttcacctacg agccgcactc cttccacctc     360
gtactcgccc ttaccgtcgc caagttcctg acggcactgg tctccttcgc gacggccatc     420
accctgctga cgctgatacc acagctcctg agggtgaagg tcaggaaaa cttcctgatg     480 aacaaggcgc gtgagctgga ccgggaggtg gggaggatga aaaggaaaga agaggcgagc     540
tggcatgtgc gcatgctcac acaggagatc cgcaagtcgc tcgacagaca taccatcttg     600
tacaccacca tggttgagct ctcgaaggca ctggaactgc agaattgtgc tgtctggatg     660
cctgatgaga ccaggagcac gatgatctta acacatcagc tgagggaaag ggatataatg     720
gacccacaga aacactcgat tcctattgat gatccggatg ttcaagaaat aaaggcaacc     780
aaggatgcaa agttcttggg cccagattcg gcgctagggg tttctagccg aagcaagcat     840
gaagcagggc ctgtggctgc aataaggatg ccgatgttaa gggtgtcaaa tttcaaagga     900
gggactccgg aagtgatgca gacgagctat gctatcttgg ttctggtttt gcctaatgat     960
ggttcattag gtggggtcg aagagagttg gagattgttg aggtagttgc tgaccaagtt    1020
gcagtcgctc tgtcacatgc tgcactccta gaggagtctc agctgatgcg agagaagctt    1080
gccgagcagc ataggacttt gctgcaggca aaggatgaag ccatgagggc aggggacgct    1140
aggaattcct tccagactgc aatgtacgat ggaatgcgaa ggccaatgca ctcaatcctt    1200
ggtctcgtct caatgatgca acaggagagc atgaatccag agcaaaggct tgtgatggat    1260
gccattgcca agacaagcag tgttgcatcc acactgatga acgatgtgat gcaaacatcg    1320
acaatgaact gtgagcactt gtctttggtc aggaggccgt tcaaccttca ttccttcatt    1380
aaagaagttg ttggagtggt cagatgtcta actggttgca agggtgtgga gtttgagttt    1440
```

```
caagtggaga attctttgcc agaaaggatc attggtgatg agaagagagt cttccatatt   1500
gtcctgcaca tggtaggcac tctaacagac cgatgtaatg ctggctgtat ctcattatat   1560
gtaaatgtcc ataatgaggt tgaagatagg cataatcatg actggatgct gcgaagagca   1620
aacttctctg ggggctatgt atgtgtgaaa tttgagatta ggattagaaa atcaaagggc   1680
tatctgttga gttcatcaag cagtcagata agtcagggat ccaaacccaa caattctgag   1740
atggggctta gcttcaatat gtgcaagaag attgtgcaga tgatgaatgg caatatttgg   1800
tcagtatcag attctaaaag catcggagaa actatcatgc tagtcctcca gttccagttg   1860
gaacctgtga ctccggtctc tggagcgtcc tcagatttgt acagatcatc cgcaattccc   1920
aactttaatg ggctcagagt cctccttgcg gacagcgact gcaccaaccg agctgtaact   1980
cacaggctcc tagagaagct tggttgccga gtcctttcgg tcgcttctgg cgtccaatgc   2040
atcagctcct cgctgcgga gtcgtccttc cagctggtgg ttcttgatct tgacatgcag   2100
acgatggatg gattcgaagt agcccgcgcg atcaggaagt tcagtagcaa tagttggctg   2160
ccgttgatta ttgccctagc agcaagaatc gacgacaaca tccgggatcg ttgccagagg   2220
tcaggagtaa atggcctgat ccagaaaccg gtcacattag ccgcgctggg agatgaactg   2280
tatagagtcc ttcagaacaa t                                             2301
```

<210> SEQ ID NO 32
<211> LENGTH: 767
<212> TYPE: PRT
<213> ORGANISM: Zea mays
<220> FEATURE:
<223> OTHER INFORMATION: Zea mays ethylene receptor (ethylene resistant receptor, ETR2-like), ETR9 protein

<400> SEQUENCE: 32

```
Met Val Val Gly Thr Ala Leu Leu Arg Gly Val Ser Ser Ala Trp Ile
 1               5                  10                  15

Leu Leu Phe Leu Ser Ser Leu Leu Leu Ser Pro Ser Ala Ala Ser Val
            20                  25                  30

Asp Phe Gly His Cys Gly Gly Cys Asp Asp Ala Asp Asp Gly Ala Leu
        35                  40                  45

Ser Ser Thr Tyr Asn Ile Leu Gln Cys Gln Lys Val Ser Asp Phe Leu
    50                  55                  60

Ile Ala Ala Ala Tyr Phe Ser Ile Pro Leu Glu Leu Leu Tyr Phe Ala
65                  70                  75                  80

Thr Cys Ser Asp Leu Phe Pro Leu Lys Trp Ile Val Leu Gln Phe Gly
                85                  90                  95

Ala Phe Ile Val Leu Cys Gly Leu Thr His Leu Ile Thr Val Phe Thr
            100                 105                 110

Tyr Glu Pro His Ser Phe His Leu Val Leu Ala Leu Thr Val Ala Lys
        115                 120                 125

Phe Leu Thr Ala Leu Val Ser Phe Ala Thr Ala Ile Thr Leu Leu Thr
    130                 135                 140

Leu Ile Pro Gln Leu Leu Arg Val Lys Val Arg Glu Asn Phe Leu Met
145                 150                 155                 160

Asn Lys Ala Arg Glu Leu Asp Arg Glu Val Gly Arg Met Lys Arg Lys
                165                 170                 175

Glu Glu Ala Ser Trp His Val Arg Met Leu Thr Gln Glu Ile Arg Lys
            180                 185                 190

Ser Leu Asp Arg His Thr Ile Leu Tyr Thr Thr Met Val Glu Leu Ser
        195                 200                 205
```

-continued

| | | | | | | | | | | | | | | |
|---|---|---|---|---|---|---|---|---|---|---|---|---|---|---|
|Lys|Ala|Leu|Glu|Leu|Gln|Asn|Cys|Ala|Val|Trp|Met|Pro|Asp|Glu|Thr|
| |210| | | |215| | | |220| | | |  |  |  |

Arg Ser Thr Met Ile Leu Thr His Gln Leu Arg Glu Arg Asp Ile Met
225             230                 235                 240

Asp Pro Gln Lys His Ser Ile Pro Ile Asp Asp Pro Asp Val Gln Glu
                245                 250                 255

Ile Lys Ala Thr Lys Asp Ala Lys Val Leu Gly Pro Asp Ser Ala Leu
            260                 265                 270

Gly Val Ser Ser Arg Ser Lys His Glu Ala Gly Pro Val Ala Ala Ile
        275                 280                 285

Arg Met Pro Met Leu Arg Val Ser Asn Phe Lys Gly Gly Thr Pro Glu
    290                 295                 300

Val Met Gln Thr Ser Tyr Ala Ile Leu Val Leu Val Leu Pro Asn Asp
305                 310                 315                 320

Gly Ser Leu Gly Trp Gly Arg Arg Glu Leu Glu Ile Val Glu Val Val
                325                 330                 335

Ala Asp Gln Val Ala Val Ala Leu Ser His Ala Ala Leu Leu Glu Glu
                340                 345                 350

Ser Gln Leu Met Arg Glu Lys Leu Ala Glu Gln His Arg Asp Leu Leu
            355                 360                 365

Gln Ala Lys Asp Glu Ala Met Arg Ala Gly Asp Ala Arg Asn Ser Phe
370                 375                 380

Gln Thr Ala Met Tyr Asp Gly Met Arg Arg Pro Met His Ser Ile Leu
385                 390                 395                 400

Gly Leu Val Ser Met Met Gln Gln Glu Ser Met Asn Pro Glu Gln Arg
                405                 410                 415

Leu Val Met Asp Ala Ile Ala Lys Thr Ser Ser Val Ala Ser Thr Leu
                420                 425                 430

Met Asn Asp Val Met Gln Thr Ser Thr Met Asn Cys Glu His Leu Ser
            435                 440                 445

Leu Val Arg Arg Pro Phe Asn Leu His Ser Phe Ile Lys Glu Val Val
        450                 455                 460

Gly Val Val Arg Cys Leu Thr Gly Cys Lys Gly Val Glu Phe Glu Phe
465                 470                 475                 480

Gln Val Glu Asn Ser Leu Pro Glu Arg Ile Ile Gly Asp Glu Lys Arg
                485                 490                 495

Val Phe His Ile Val Leu His Met Val Gly Thr Leu Thr Asp Arg Cys
                500                 505                 510

Asn Ala Gly Cys Ile Ser Leu Tyr Val Asn Val His Asn Glu Val Glu
            515                 520                 525

Asp Arg His Asn His Asp Trp Met Leu Arg Arg Ala Asn Phe Ser Gly
        530                 535                 540

Gly Tyr Val Cys Val Lys Phe Glu Ile Arg Ile Arg Lys Ser Lys Gly
545                 550                 555                 560

Tyr Leu Leu Ser Ser Ser Ser Gln Ile Ser Gln Gly Ser Lys Pro
                565                 570                 575

Asn Asn Ser Glu Met Gly Leu Ser Phe Asn Met Cys Lys Lys Ile Val
            580                 585                 590

Gln Met Met Asn Gly Asn Ile Trp Ser Val Ser Asp Ser Lys Ser Ile
        595                 600                 605

Gly Glu Thr Ile Met Leu Val Leu Gln Phe Gln Leu Glu Pro Val Thr
610                 615                 620

Pro Val Ser Gly Ala Ser Ser Asp Leu Tyr Arg Ser Ser Ala Ile Pro
625                 630                 635                 640

Asn Phe Asn Gly Leu Arg Val Leu Leu Ala Asp Ser Asp Cys Thr Asn
            645                 650                 655

Arg Ala Val Thr His Arg Leu Leu Glu Lys Leu Gly Cys Arg Val Leu
            660                 665                 670

Ser Val Ala Ser Gly Val Gln Cys Ile Ser Ser Phe Ala Ala Glu Ser
            675                 680                 685

Ser Phe Gln Leu Val Val Leu Asp Leu Asp Met Gln Thr Met Asp Gly
        690                 695                 700

Phe Glu Val Ala Arg Ala Ile Arg Lys Phe Ser Ser Asn Ser Trp Leu
705                 710                 715                 720

Pro Leu Ile Ile Ala Leu Ala Ala Arg Ile Asp Asp Asn Ile Arg Asp
                725                 730                 735

Arg Cys Gln Arg Ser Gly Val Asn Gly Leu Ile Gln Lys Pro Val Thr
            740                 745                 750

Leu Ala Ala Leu Gly Asp Glu Leu Tyr Arg Val Leu Gln Asn Asn
        755                 760                 765

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence:Zea mays
      ethylene receptor (ethylene resistant receptor,
      ETR2-like ZmETR9) ETR9 forward primer

<400> SEQUENCE: 33
gctatgtatg tgtgaaattt gagattagga                                    30

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence:Zea mays
      ethylene receptor (ethylene resistant receptor,
      ETR2-like ZmETR9) ETR9 reverse primer

<400> SEQUENCE: 34
agctaacctg gcagaaatta gttaccga                                      28

<210> SEQ ID NO 35
<211> LENGTH: 5573
<212> TYPE: DNA
<213> ORGANISM: Zea mays
<220> FEATURE:
<223> OTHER INFORMATION: Zea mays ethylene receptor (ethylene resistant
      receptor, ETR2-like), ETR40 genomic DNA

<400> SEQUENCE: 35
aaactgcgca actcgtgaaa ggtaggcgga tctgggtcga cctgcaggtc aacggatcag     60
actccaaggc ctacaacaag catatcagac cccgattcta gcaataaaag acaaggttcg    120
tcttcacccc tactttccta tgccaattat ccggttggtg aggtgacaca gtaaccaatg    180
aggtgggtgt acgaatggga ggacattaag tactaccaaa tgttggtgga gtcatggatt    240
acgacttctt cgtggaccga tcagacttgg acagggtaca atgcacaatt gatacatgag    300
caaggtatta tgttgctatc aacggaggag tataatatgg cacaagcaca atatcagtgg    360
aatgcaccat gtgtgaatga tctttgacgg agcaacaact gtgaactatg aatggtgtat    420
ttttatcttc gtcattgttt gtgaactatg aaactgctaa atattattat taaaattgtg    480

| | |
|---|---|
| atattgttta gggtcatctt ttgtttaaat tatggagcct taatatgctt tatttacaaa | 540 |
| atacatatag ctcggtcttt atttctatgc tgtcgattta tcaggccaaa aaccgattaa | 600 |
| tcagtcttat cgatttatgg gttttgaatt aaaattttt gaccaattcc tacctatttt | 660 |
| caccggtatc gatgggcaca tgttttcaca atttcacccc tcagatcttg ttcggttatt | 720 |
| ttcaatctat atagattgga agtaattgat tcaaattgaa agaaatttta acttactaag | 780 |
| attaaaattc actaaatctt tctcaatcca tataaattag gatagaaccg aacaaaccct | 840 |
| caaccggttt agtgaacccc gccggagaga caacccaacc ccctgctcg acccgctgaa | 900 |
| ctgccgaagc atcgcctact cttcctactc agctccgctg gtccggtcgt cgcgtagcgc | 960 |
| cctcacccc agccacccc accacgaagg ccgcgcgctc cccgccttcc gacgtcgctc | 1020 |
| tctccgccca gctcaagcgc ccagcggtga gggaagggaa ggaaaaacag accttttttt | 1080 |
| ttcttctcgg cggcctcgtg actatggatc cgccgagctc cggtctcccg ccggtgccga | 1140 |
| ggtttcctgg ctcgatccgt gaccggccca cgtggagacg tgctggtgc tagtaccggt | 1200 |
| gcctccaccg tgtttcttgg cgaccttact acctcctctc ctcctctgga agattgctgc | 1260 |
| tgcagcctgc aggaaagatg gccgaacgcc gaaggtgggc agcgttagtt actcctccat | 1320 |
| gcttttttcc ttcagttcaa caaatatgtt tggattttt tttaccggac tgtggaatgc | 1380 |
| ttcgagctcg ggggttttatc ggatttgggc tgttctaaat ctcctaccta ctctggccca | 1440 |
| tatttttacc ttctggagta cgtgtataac aagatccatg gtggactgat ggattcggtt | 1500 |
| ttgaccgata catgtatttc gatgctattt tttggaagga ttaaatcttc aacacgtgcc | 1560 |
| caagcccaac cgcccaaagg catcgatttg ctttttcgcca gatcttgatt tgtgtgccgc | 1620 |
| ggtttgattg attgcaaagc tgtgatgtta actgcgttca atttgtactt atactacatc | 1680 |
| tgatgaatgc aggagcgtcg gcgcgtgcag tgtggaatcg acgccgagcg cctccagtcg | 1740 |
| gtgcaggaat gcgcaaatgc acgtctgaat gaagcctggt tggtggtaga gccgatggtg | 1800 |
| gtgggaacgg cgccgtgcgg ggtctccgtc tcctccgtgt ggatcctcct gctccttttcc | 1860 |
| tccctgctcc tctcgccgtc ggcggcgtcc gtcgatttcg gccactgcgg ctgcgacgac | 1920 |
| gccgacgacg gcgccctctc gagcacctac aacatcctgc aatgccagaa ggtcagcgac | 1980 |
| ttcctcatcg ccgcggccta cttctccatc ccgctcgagc tgctctactt cgccacctgc | 2040 |
| tccgacctttt tcccccctcaa atggatcgtg ctgcagttcg gcgccttcat cgtgctctgc | 2100 |
| ggcctcacgc acctcatcac cgtgttcacc tacgacccgc actccttcca cctcgtgctc | 2160 |
| gccctcaccg tcgccaagtt catgacggca ctagtctcct tcgccacagc catcacgctg | 2220 |
| ctgacactga taccgcagct cctgagggtg aaggtcaggg aaaacttcct ggtgaacaag | 2280 |
| gcacgtgagc tggaccggga ggtggggatg atgaaaatga agaagaggc gagctggcat | 2340 |
| gtgcgtatgc tcacacagga gatccgcaag tcgctcgaca ggcacaccat cttgtacacc | 2400 |
| accatggttg agctctcgaa agcgctggaa ctgcagaatt gtgctgtctg gatgcccgat | 2460 |
| gaaaccagga gcgagatgat cttaactcat cagccaaggg aaagggatat aatggaccag | 2520 |
| cagaactgct cgattcctat tgatgatcca gatgttcaag aaataaaggc taccaaggac | 2580 |
| gcaaaagttc ttgggccaga ttcggcacta ggggttgcta cccgcaagct tgacgtgggg | 2640 |
| cctgtggctg caataaggat gccgatgtta agggtgtcaa atttcaaagg agggactcca | 2700 |
| gaagtgatgc agacgagcta tgctatcttg gttctggttt tgcctaatga tggttcattg | 2760 |
| gggtggggta agagagagtt ggagattgtt gaagtagttg ctgaccaagt tgcggtcgct | 2820 |
| ttgtcacatg ctgcactcct agaggagtct cagctgatgc gagagaaact tgctgagcag | 2880 |

```
tatagggact tgctgcaggc aaagcatgaa gccatgaggg caggggaagc tcggaattcc    2940
ttccagactg caatgtacga cggaatgcga aggccaatgc actcaatcct tggtcttgtc    3000
tcaatgatgc aacaggagag catgaatcca gagcaaaggg ttgtgatgga tgccattgcc    3060
aagacaagca gtgttgcgtc cacactgatg aatgatgtga tgcaaacatc gacaatgaac    3120
tgtgagcact tgtctttggt gaggaggccg ttcaatcttc attcttttat taaagaagct    3180
gttggagtgg tcagatgtct aactggttgc aaggtgtag agtttgagtt tcaagtggat    3240
aattctttgc cagaaaggat cattggtgat gagaagagag tcttccacat tgtcctgcac    3300
atggtaggca ccctaataaa ccgatgtaat gtcggctgta tctcgttata tgtcaatggt    3360
cataatgagg ttgaagagag gcataatcat gactggatgc tgcggagaac aaacttctct    3420
gggggctatg tttgtgtgaa atttgagatt aggattagaa aatccaagga ctatcttttg    3480
agttcaaacg gtcagataag tcatgggtcc aaaccaaaca attctgagat ggggcttagc    3540
ttcaatatgt gcaagaagat tgtgcaggta atcgaaata ataaaacatc tcaagcattt    3600
acatccaata ggaagaaaac tatattgtca tctcgtttat gtcactcgct cctggtgctt    3660
ctcaggctct gtatatatat tgctgataat gcttggttag gtttgacttc tatgcaaggt    3720
taatattgtt aaagcgacaa caatttatta gattgtggtg gttctgttac cctacttgac    3780
tcagtttatc ttcgattact tggaccttcc agactttgac agatgctaga aaatattag    3840 cggttctttg atctcgagtg acacaaattt ttttagaacc tgttgactgt tctccatctc    3900
tcgtattttt tgtacagctg gggactagca tcttaggcct taggcttggt cgtcacatag    3960
ctagttggcc acacaccaat ttgaacaaga cagaatatgt ttggcggcca tagtgtggcc    4020
ttttatgcaa gcccttggaa tatttattat ctcataaaaa actgggtaaa ccgtgagaac    4080
atattggccc ttttgttgaa ctgatgcttt agtaattagt cataattatt ttatggtatt    4140
tttttctgga agcttgcatg gtttcgcgta aatatatttc gtctagttat gctagtagta    4200
gcccaaacct cagcgactct atttgattgt tatgattcgg tcagcaattt gttcattagc    4260
tgtgggaatg gtcaatgcgc acttgatttg atgtacagtc attagtacgc tgatgtgagc    4320
ccttatttct gctgcagatg atgaacggca acatttggtc agtatcagat tctaaaagcg    4380
ttggagaaac catcatgctg gtcctccagt tccagctgca gcctctgact gcggtctcct    4440
ccgcggcgtc ttcagacttg agccgatcgt ccgcaatccc caacttcaac gggctcagag    4500
tcctcctggc ggacagcgac gacaccaaca gagcagtaac acacaggctc ctggagaagc    4560
tcggctgccg ggtcctttcg gtcgcctccg gtgtccaatg cacgagctcc ttcgccgccg    4620
agccgtcctt ccagctggtg gtcctggacc tcgccttgca gaggacggac gggctcgaag    4680
tggcccgcgc gatcaggaag ttcagtagca atagctggct gccgctgatc gtcgccctag    4740
ctgcgaggat cgatgacaag gtccgagacg gatgccagag gtcggggata agcggcctga    4800
tccagaaacc ggccacgtta gctgcgctgg gagatgagct gtatagggtc cttcagaaca    4860
gttgaaagtg ccgcctgatg gttctcattg ctttcagaat tctcaataga ccgctgtagc    4920
ttggttagat ccatacattc acaaaacatt tgggggcagg cgaagggaaa tgtataggaa    4980
aagctggaag accgctgctt ctcgcttggt tcctcagtag tgaaggacga cggtgacagg    5040
aaggtacaga attttggaga gatcatactg gtagagctta gactcattca tttgtaaaac    5100
cctcggataa tccaaggttt agattcttgc actagcacta accacggtat aaatagtttg    5160
gacgaaatcc atggatgggt tcagtgaatg ctggcatagt agatgcctaa aggggcaag    5220 gaacttttgt tatcggttag acatgctgaa aagcaggccg gatgagattg cggacaggaa    5280
```

```
ggcagctgat acggccgatg ctgaccttgt atcttgttga agattaaata ctatggtagt    5340
agtacttgca gtcttgatct ggtgggtagt gctggtgctc ctgctgcatt tcttacttgc    5400
ttggcctgct tctggccagc aaactcctgc ttgccatctt cttagcactg attcctatgg    5460 ttttttaat agggtatcct ttcaactgtt gagacacatt accacacata tataaaaaac    5520 attttaatc ccttgctacc gaagcttcag atgtcatctc aagagctatt cta            5573
```

<210> SEQ ID NO 36
<211> LENGTH: 2298
<212> TYPE: DNA
<213> ORGANISM: Zea mays
<220> FEATURE:
<223> OTHER INFORMATION: Zea mays ethylene receptor (ethylene resistant
      receptor, ETR2-like), ETR40 coding sequence (CDS)

<400> SEQUENCE: 36

```
atggtggtgg gaacggcgcc gtgcggggtc tccgtctcct ccgtgtggat cctcctgctc     60
cttcctcccc tgctcctctc gccgtcgcg cgtccgtcg atttcggcca ctgcggctgc     120
gacgacgccg acgacggcgc cctctcgagc acctacaaca tcctgcaatg ccagaaggtc    180
agcgacttcc tcatcgccgc ggcctacttc tccatcccgc tcgagctgct ctacttcgcc    240
acctgctccg accttttccc cctcaaatgg atcgtgctgc agttcggcgc cttcatcgtg    300
ctctgcggcc tcacgcacct catcaccgtg ttcacctacg accgcactc cttccacctc    360 gtgctcgccc tcaccgtcgc caagttcatg acggcactag tctccttcgc cacagccatc    420
acgctgctga cactgatacc gcagctcctg agggtgaagg tcagggaaaa cttcctggtg    480
aacaaggcac gtgagctgga ccgggaggtg gggatgatga aaatgaaaga gaggcgagc    540 tggcatgtgc gtatgctcac acaggagatc cgcaagtcgc tcgacaggca caccatcttg    600
tacaccacca tggttgagct ctcgaaagcg ctggaactgc agaattgtgc tgtctggatg    660
cccgatgaaa ccaggagcga gatgatctta actcatcagc aagggaaag ggatataatg    720 gaccagcaga actgctcgat tcctattgat gatccagatg ttcaagaaat aaaggctacc    780
aaggacgcaa aagttcttgg gccagattcg gcactagggg ttgctacccg caagcttgac    840
gtggggcctg tggctgcaat aaggatgccg atgttaaggg tgtcaaattt caaaggaggg    900
actccagaag tgatgcagac gagctatgct atcttggttc tggttttgcc taatgatggt    960 tcattgggt ggggtagaag agagttggag attgttgaag tagttgctga ccaagttgcg    1020
gtcgctttgt cacatgctgc actcctagag agtctcagc tgatgcgaga gaaacttgct    1080
gagcagtata gggacttgct gcaggcaaag catgaagcca tgagggcagg ggaagctcgg    1140
aattccttcc agactgcaat gtacgacgga atgcgaaggc caatgcactc aatccttggt    1200
cttgtctcaa tgatgcaaca ggagagcatg aatccagagc aaagggttgt gatggatgcc    1260
attgccaaga caagcagtgt tgcgtccaca ctgatgaatg atgtgatgca acatcgaca    1320 atgaactgtg agcacttgtc tttggtgagg aggccgttca atcttcattc ttttattaaa    1380
gaagctgttg gagtggtcag atgtctaact ggttgcaagg gtgtagagtt tgagtttcaa    1440
gtggataatt ctttgccaga aaggatcatt ggtgatgaga agagagtctt ccacattgtc    1500
ctgcacatgg taggcaccct aataaaccga tgtaatgtcg gctgtatctc gttatatgtc    1560
aatggtcata tgaggttgaa agagaggcat aatcatgact ggatgctgcg gagaacaaac    1620
ttctctgggg gctatgtttg tgtgaaattt gagattagga ttagaaaatc caaggactat    1680
cttttgagtt caaacggtca gataagtcat gggtccaaac caaacaattc tgagatgggg    1740
cttagcttca atatgtgcaa gaagattgtg cagatgatga acggcaacat ttggtcagta    1800
```

```
tcagattcta aaagcgttgg agaaaccatc atgctggtcc tccagttcca gctgcagcct   1860
ctgactgcgg tctcctccgc ggcgtcttca gacttgagcc gatcgtccgc aatccccaac   1920
ttcaacgggc tcagagtcct cctggcggac agcgacgaca ccaacagagc agtaacacac   1980
aggctcctgg agaagctcgg ctgccgggtc ctttcggtcg cctccggtgt ccaatgcacg   2040
agctccttcg ccgccgagcc gtccttccag ctggtggtcc tggacctcgc cttgcagagg   2100
acggacgggc tcgaagtggc ccgcgcgatc aggaagttca gtagcaatag ctggctgccg   2160
ctgatcgtcg ccctagctgc gaggatcgat gacaaggtcc gagacggatg ccagaggtcg   2220
gggataagcg gcctgatcca gaaaccggcc acgttagctg cgctgggaga tgagctgtat   2280
agggtccttc agaacagt                                                  2298
```

<210> SEQ ID NO 37
<211> LENGTH: 766
<212> TYPE: PRT
<213> ORGANISM: Zea mays
<220> FEATURE:
<223> OTHER INFORMATION: Zea mays ethylene receptor (ethylene resistant
      receptor, ETR2-like), ETR40 protein

<400> SEQUENCE: 37

```
Met Val Val Gly Thr Ala Pro Cys Gly Val Ser Val Ser Ser Val Trp
  1               5                  10                  15

Ile Leu Leu Leu Leu Ser Ser Leu Leu Leu Ser Pro Ser Ala Ala Ser
                 20                  25                  30

Val Asp Phe Gly His Cys Gly Cys Asp Asp Ala Asp Asp Gly Ala Leu
             35                  40                  45

Ser Ser Thr Tyr Asn Ile Leu Gln Cys Gln Lys Val Ser Asp Phe Leu
         50                  55                  60

Ile Ala Ala Ala Tyr Phe Ser Ile Pro Leu Glu Leu Leu Tyr Phe Ala
 65                  70                  75                  80

Thr Cys Ser Asp Leu Phe Pro Leu Lys Trp Ile Val Leu Gln Phe Gly
                 85                  90                  95

Ala Phe Ile Val Leu Cys Gly Leu Thr His Leu Ile Thr Val Phe Thr
            100                 105                 110

Tyr Asp Pro His Ser Phe His Leu Val Leu Ala Leu Thr Val Ala Lys
        115                 120                 125

Phe Met Thr Ala Leu Val Ser Phe Ala Thr Ala Ile Thr Leu Leu Thr
    130                 135                 140

Leu Ile Pro Gln Leu Leu Arg Val Lys Val Arg Glu Asn Phe Leu Val
145                 150                 155                 160

Asn Lys Ala Arg Glu Leu Asp Arg Glu Val Gly Met Met Lys Met Lys
                165                 170                 175

Glu Glu Ala Ser Trp His Val Arg Met Leu Thr Gln Glu Ile Arg Lys
            180                 185                 190

Ser Leu Asp Arg His Thr Ile Leu Tyr Thr Thr Met Val Glu Leu Ser
        195                 200                 205

Lys Ala Leu Glu Leu Gln Asn Cys Ala Val Trp Met Pro Asp Glu Thr
    210                 215                 220

Arg Ser Glu Met Ile Leu Thr His Gln Pro Arg Glu Arg Asp Ile Met
225                 230                 235                 240

Asp Gln Gln Asn Cys Ser Ile Pro Ile Asp Asp Pro Asp Val Gln Glu
                245                 250                 255

Ile Lys Ala Thr Lys Asp Ala Lys Val Leu Gly Pro Asp Ser Ala Leu
            260                 265                 270
```

```
Gly Val Ala Thr Arg Lys Leu Asp Val Gly Pro Val Ala Ala Ile Arg
            275                 280                 285

Met Pro Met Leu Arg Val Ser Asn Phe Lys Gly Gly Thr Pro Glu Val
290                 295                 300

Met Gln Thr Ser Tyr Ala Ile Leu Val Leu Val Leu Pro Asn Asp Gly
305                 310                 315                 320

Ser Leu Gly Trp Gly Arg Arg Glu Leu Glu Ile Val Glu Val Val Ala
            325                 330                 335

Asp Gln Val Ala Val Ala Leu Ser His Ala Ala Leu Leu Glu Glu Ser
            340                 345                 350

Gln Leu Met Arg Glu Lys Leu Ala Glu Gln Tyr Arg Asp Leu Leu Gln
            355                 360                 365

Ala Lys His Glu Ala Met Arg Ala Gly Glu Ala Arg Asn Ser Phe Gln
            370                 375                 380

Thr Ala Met Tyr Asp Gly Met Arg Arg Pro Met His Ser Ile Leu Gly
385                 390                 395                 400

Leu Val Ser Met Met Gln Gln Glu Ser Met Asn Pro Glu Gln Arg Val
            405                 410                 415

Val Met Asp Ala Ile Ala Lys Thr Ser Ser Val Ala Ser Thr Leu Met
            420                 425                 430

Asn Asp Val Met Gln Thr Ser Thr Met Asn Cys Glu His Leu Ser Leu
            435                 440                 445

Val Arg Arg Pro Phe Asn Leu His Ser Phe Ile Lys Glu Ala Val Gly
            450                 455                 460

Val Val Arg Cys Leu Thr Gly Cys Lys Gly Val Glu Phe Glu Phe Gln
465                 470                 475                 480

Val Asp Asn Ser Leu Pro Glu Arg Ile Ile Gly Asp Glu Lys Arg Val
            485                 490                 495

Phe His Ile Val Leu His Met Val Gly Thr Leu Ile Asn Arg Cys Asn
            500                 505                 510

Val Gly Cys Ile Ser Leu Tyr Val Asn Gly His Asn Glu Val Glu Glu
            515                 520                 525

Arg His Asn His Asp Trp Met Leu Arg Arg Thr Asn Phe Ser Gly Gly
            530                 535                 540

Tyr Val Cys Val Lys Phe Glu Ile Arg Ile Arg Lys Ser Lys Asp Tyr
545                 550                 555                 560

Leu Leu Ser Ser Asn Gly Gln Ile Ser His Gly Ser Lys Pro Asn Asn
            565                 570                 575

Ser Glu Met Gly Leu Ser Phe Asn Met Cys Lys Lys Ile Val Gln Met
            580                 585                 590

Met Asn Gly Asn Ile Trp Ser Val Ser Asp Ser Lys Ser Val Gly Glu
            595                 600                 605

Thr Ile Met Leu Val Leu Gln Phe Gln Leu Gln Pro Leu Thr Ala Val
610                 615                 620

Ser Ser Ala Ala Ser Ser Asp Leu Ser Arg Ser Ser Ala Ile Pro Asn
625                 630                 635                 640

Phe Asn Gly Leu Arg Val Leu Leu Ala Asp Ser Asp Thr Asn Arg
            645                 650                 655

Ala Val Thr His Arg Leu Leu Glu Lys Leu Gly Cys Arg Val Leu Ser
            660                 665                 670

Val Ala Ser Gly Val Gln Cys Thr Ser Ser Phe Ala Ala Glu Pro Ser
            675                 680                 685

Phe Gln Leu Val Val Leu Asp Leu Ala Leu Gln Arg Thr Asp Gly Leu
```

```
                690             695             700
Glu Val Ala Arg Ala Ile Arg Lys Phe Ser Ser Asn Ser Trp Leu Pro
705                 710                 715                 720

Leu Ile Val Ala Leu Ala Ala Arg Ile Asp Asp Lys Val Arg Asp Gly
                725                 730                 735

Cys Gln Arg Ser Gly Ile Ser Gly Leu Ile Gln Lys Pro Ala Thr Leu
            740                 745                 750

Ala Ala Leu Gly Asp Glu Leu Tyr Arg Val Leu Gln Asn Ser
        755                 760                 765

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence:Zea mays
      ethylene receptor (ethylene resistant receptor,
      ETR2-like, ZmETR40) ETR40 forward primer

<400> SEQUENCE: 38
gctatgtatg tgtgaaattt gagattagga                                   30

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence:Zea mays
      ethylene receptor (ethylene resistant receptor,
      ETR2-like, ZmETR40) ETR40 reverse primer

<400> SEQUENCE: 39
aagctacagc ggtctattga gaattct                                      27

<210> SEQ ID NO 40
<211> LENGTH: 8237
<212> TYPE: DNA
<213> ORGANISM: Zea mays
<220> FEATURE:
<223> OTHER INFORMATION: Zea mays ethylene receptor (ethylene
      insensitive receptor, EIN2-like), E2-25 genomic DNA
<220> FEATURE:
<221> NAME/KEY: modified_base
<222> LOCATION: (126)
<223> OTHER INFORMATION: n = g, a, c or t

<400> SEQUENCE: 40
aaacccactc ttgccacccc gtgacagcag gaaacagtac acagtagcgc ataaccttcc    60
aagaaaattt aattaataaa cccgaagaag ccaagaggga agggaaaaaa aagaaagaa    120 aaaaanctga cacataagaa aagagcagcg agcaagctga aggtgaaagc cacagcagct   180
cgtccccttc cccccacttc ttcctcagat aaggagaggc cccaggccag agaaaaaagc   240
atcgaatttc ccccgttaa ttggcctgag ccctcagccg tctaccagca gcagctagag    300
gtacgattct cgcattgctt gctccctgcg cctgccctcg attttgctg ttttttcgag    360 ctcctcttcc agttcttttg ccgtgttgga accgcatcta tgcagcctag cgcggggtac   420
tagcgtgatt cggtcagtgg atcccgtcgg gctgctgctt cctcgcggct gatttgcgag   480
aggaagcagg tccccgggaa gcgatctcat ttttcgttat ttttttagct ccctacacca   540
aagaccagag tcagatccga ggctacccgc cgcccggca aggatttac ccggccggag     600 ctctgcaaca tcggtgggat cgatggctgc gacctccacg agctccggtg cccacgaatc   660
gaagtcagca gcgccgtgtg gactgagtca cgtgcctggt tcgccgtcct gtccgacgct   720
```

```
tctcacctcg agagcccgtc gctgttgcct cggactcgag ggagctggcg gcgcaaacgc    780
cgtgcggcca aaatcgagat ccccaccatc cgaatcgagg tcctctctac cagaatcagt    840
tcccgccgcc gcgtcgaggt agctgtcacc caaattgagc tttccgtcgc tgctggatgt    900
gttggaatcg gaagcttcgg gcgcatagct tgagctcgct caagtgtatc gagcaagcaa    960
accaagcgtt gggggtcttg ctttgcgcct ttgccgcgct agcttagcct atctatccgt    1020
gctaggaatc cccctcccct tcggtgtgat gttttttgact tgccactgcc tggtgttgct    1080
ggggctgctt ttctcttctc ctttgggggct ctgaatgaag actgaagaaa tcgaaagaga    1140
ggaaagctac gcctgagtcg gggaacgcct acgaagtaag ttttggctta aggtggaag    1200 cttttgaggt ttctccttgc gaaataaatg cttttttcga tgttatttga tggatttggt    1260
tggtactcgg tcaaaaggtg ttcttggttt gcccctttcta tgctctggct gctgttgcaa    1320
ctgcaacttc cctttccctt agagtttggc gctctaaaag ttggttcact ttgcacgaag    1380
gatttctgtt tcttgttgct gattgggttg tttggatcta tctgcaggca gacaagctag    1440
gttttactgc ttcattgagc acaaagatcc gctgacctct tgctcttggt aaaaatccaa    1500 ccttcttgt attgttttct tcctgggaaa acctccttgt ggtgcataaa cttcgtagta    1560
cactctgcca tttctggaga ggaagctgag aactactatc catatctggc acgacccttg    1620
tcaagaacca tggctgttca catgccatga agctgcttga actggaggca cctaaatgct    1680
gtggattgtt cctatgcaga tgattggatc agtggtttca ggcttcgggg ggttcgatca    1740
gatgttgtat gaataatagc aggattgctt gagagactat agtttgggta ctgtttgctt    1800
ctgtatttac tggtacggtt tcctactgat ctgcggctgc gcaggaaggc attctctttt    1860
ttgccgtacc atggatgcac cggatgttca acagagcatg ggatataagg agtccagggg    1920
tggtatgcct aagttttcc atgcccttgg accagcactc ctgatttcaa tgggttacat    1980
tgatctcggg aagtgggtgg cagccgttga agctggttct tgttttggat cgacctggt    2040 gttgctggct ctccttttca atttcactgc cattgtatgt cagtaccttg ctgcttgcat    2100
tggcactgtc acagggaaga atcttgcaga ggtatcggtt taccgatgtt gttccttggt    2160
tttgctggcc ttctattgag atttagttca gtaaatcttt gtttccattt cacaacgcta    2220
tatgatggct tcatattgag ctggacttga aggaacttag aagagcaggg agtagggaaa    2280
ctacatgcga gatattcaat ttatgcgaat tgttgataaa caaaatggat caattcactt    2340
gccttgttaa ataattcttt tccatctgta gttcaattat actccctctg ttccacaata    2400
gaagtcgttt tagactttca acaaattcat tcaataattg atgtatatgt tatgtaatgt    2460
gtctagattc gttgccattc atttgaatat agacataaaa agaagaccta aaacgactac    2520
taatttggta cagagggagt agtactgttg gatgtagaag ggcttctttt tggaggaaaa    2580
tatatctttt atctcatctt acttgttctt gatattcctt tcaagttgct aactttttca    2640
tgccttcaca tgaaacaaag atatgccacc aagagtacaa ccagccaaca tgtatattcc    2700
ttggtgttca agctggattg tcttttgttga cgtcagagct gagtatggta cttgcagatt    2760
tagttggatg tctctcatac cttttatgtt taaattgtga attctcatcc tgcaaagcaa    2820
tgttacatga tgtagttctg acatgctaga ttctgttggc tatatctgga attttcagat    2880
ttttggcata gcactcggat tcaacctcct gtttgaatat gatgatctca tcacagggat    2940
atgctttgca acagtggtac ctaatctgct accatatgct atatcccacc tggtaaggtt    3000
actacttcaa gaaagatact tgaacagatg ctgatacact aatgtgactt tatgtttgct    3060
agttacttac cctttatgtc tgctctaggg aagaagatg gaagggacaa taaatgcctg    3120
```

```
catagcagga tttgcacttc ttagttatgt gcttggctta ttggttagcc agccacaaat    3180
tcctctcacg atgaatgtaa tattccccaa gatcagtggt gagagtgctt actctctgat    3240
ggcgcttctt ggtgcaaaca taatggcaca caacttctac attcattcat cagttgtcca    3300
ggtaaattgt ttgattagtg cccttggact taaaatttag tgggcaacgc cttgccagaa    3360
atacttcaaa ccatacattt acatttattt caattttagc ttgttgtatg gagtttgtaa    3420
agtcctaaga gtgagcgaga tcattatatt tgaacttctg ttcatgccag ttgaatattg    3480
gatacaattt gaaaattata tttatttcct ttattatttt gatgatttgt gggtacacca    3540
catcgaaata aaacaagatg taattaatcg cgtttcaatt gtttggataa cttcatacaa    3600
gtttccaccg caggatccac actttgttta tctgtacaca ttgtgctcag cttttggaat    3660
tttttgttta gttcatgaaa ttttgtgtct tatgtttggg tttgtagcat atcacaaaac    3720
atcaaaattg taccatttct aacttttcac atcatgttca ttggaaaata ttgacatgtg    3780
caaaaaatgc aagtagtgac agtttgcgta ctttgcagtc gtttgttttc actgaattgt    3840
catcagtttc tgcgtgtttt ttaatcaaga aacattgtat ttgcagggtc agaaaaagtc    3900
atctgcagtt ggtcttggag ccttatttca cgaccacctt ttttcaatat tgttcatttt    3960
tactggaatc tttatggtga actatgttct aatgaactct gcagcagcgg aatctactaa    4020
tactcttctc attaccttcc aagatgttgt agagctaatg aatcaggtaa gcagctaaat    4080
ttcctagttg tttattctct gtgctaagtt tctgctgaat attttattta ggaagatatc    4140
ctactccgct atagaaaact gaattttga gtactttgca gatatttgta aaccctctgg    4200
caccaactat atttttagtg gttcttctct tctccagcca catcatctcg ctgacatctg    4260
ctatcggtag ccaagtgatt tcacaccatt tattcggtat aaaccttcct ctttctggac    4320
atcgtctcct actgaaggtt tttgccatag ttcctactct gtactgggcg aaagttgcag    4380
gagctgaagg gatataccaa ttattaatta tatgccagat tattcaagcc atgcttcttc    4440
catcttcagt cgtcccactt tttcgtgttg cttcatcaag atcaataatg ggagcccata    4500
gagtgtcttt gcatctggag atactggttt ttcttgcatt tctccttatg ctattttcaa    4560
atatcatatt tgtggcagaa atgctatttg gcgacagtgg gtggatgaac aatctgaaag    4620
gatatactgg aagccctgtg gtgctcccat ataccgtttt agttttagtt gcacttatat    4680
ctgtggcttt ttcactgtac ctggctgtta caccattgag atctggaagt catgaagctg    4740
aatcccatga atggtctgtg cattctcaga gagaactctt gaatacttct caagaaaggg    4800
aagatgttaa ggtggacaat gttacatatg aggaagatca aagatcagat gttgtccctt    4860
ctcccaggga tgtgcctgac agccatccgg aactggcctt ggactatatt gatacttctg    4920
acactgctgt agaatctgat cacgactctc aacaatctac tgcttatgca tccactgctc    4980
ctgaaacctg ctcctcccg tcgtttactc gcgaggagtc aaaatcagtt gttgcagtca    5040
actggccgga gcctttggag aaggttccta cttctactgt gatggaggaa agcacagtag    5100
aaaatgtggt ctctaggatc acgactgaaa gagatgtttt agtagaaaca gatgttgtct    5160
cgggcaagga taaggaagat atccgtactt tggagtctga aagtcaatt gttgatagca    5220 ccccatatgt gtctgatgac ggtccgccat cccttacttt cagcagggga aagggctcag    5280
atgcaggaaa tggcagtggt agtctctcaa ggttatctgg tttgggccgt gcagcaagga    5340
gacagctagc tgctactctt gatgagttct gggggcatct gtttgattac catggtaagc    5400
tcactcaaga agctagcacc aaaaagtttg gtatcttgct tgggatagac cttagaacac    5460
ctagcacatc tgtaagaacg gataaacaag ctgctgaaat acttaagagc ccactggtga    5520
```

```
gagactcaat gcgggggggca gcttttttgt caagctcagt ggacatgatg tccctaaga    5580
atgaaacgtc gaatttggaa cttgcatatg ggcttcagag gggacctggc atgggattgt    5640
caagctggtc tcagggtatg cagctaccaa atacacagct gcagagctca agcaatagcc    5700
tacttgagca gagtgcaaga ttaaactcaa attttagttc atcttattca gacaacaatc    5760
agttctacca acctgcaaca attcatggat accagctcac atcttacctg aaacagatga    5820
atgccagccc aagcctttac tctagcatgc cgctggaccc acaacggctt ccaaaatcat    5880
ctgtgtctgc tgtgccaaac tatgctgatt ccatgatgca tgctcgtaat cataacctgc    5940
ttgcttcact gggtggtact actacacagc ttcctgcaac atcccgcgta ggctcaatga    6000
tgcctgaaag atcgtattat gatccttcca gcgttgatgg gaatgaaaac gctggttcac    6060
ctgcttactc aaaaaagtac cacagctcac ctgatatgtc tggaataatc gctgcaagta    6120
gagctgcact cttgaatgaa gcaaagttgg gtgctgccat ggaccacag tcatacctca    6180
gcaggctggc ggcagaaaga tctcaatatg caagctcaac agccaggccc gcggctccat    6240
tagcatttga cgagctttca cctcctaagc tccagagtga tatcttctcg gcgcagtcaa    6300
gcatgagacc aagtgctaga tcccttgggg ctaagcaacc atttgagcaa ttgttcggca    6360
tgtcaagtgc agagctcagt aaaggtgact tcaatcttcc aggcagatca ggtggcgtgg    6420
ccaaggatga tttctcttat aaggaatctg agacgaagct tcttcagtcc ctcaggctct    6480
gcatcatgaa gctccttaag ctagagggat cagggtggct gttcaagcaa aatggtggtt    6540
gtgatgaaga tctaatcgac cgagtcgctg cagccgagaa gctattgatg caagggactg    6600
ccgagaatca actgctgctt catggtggtg atctccagca acattcttcc gaccaggccg    6660
gcatccagta catgcgcacg cttcccaact gcggggagga ctgtgtttgg cgcgcgtcac    6720
tcgtcgttag tttcggtgtc tggtgtgtcc gccgagtgct ggacatgtct ctggtggaaa    6780
gcaggccaga actttgggc aagtatacct atgtccttaa ccgtcttcag gtgagttgtt    6840
atggtcctga actagtttaa ctttttttt tgcaatcgat aatatcctgt ttttaatact    6900
tgcttacaat taggggtgga caatcatctg aaatggcatt acaatataga aaacaaaagg    6960
actgcccag attttcccg tatttatgaa gatatctagt agcacaaaaa aatagctgtg    7020
aaatcagtta aaaatgacat tttttttaat gtttgcgtga attcagaaac gttctaaaac    7080
ggtatcatat tatagaaaac gagaatgaag gatttgtgct gttcacttaa cagtgattca    7140
ttttatgttt gtgcagggga tcttggaccc tgcgttctcc aagcctcggg gtgctctgac    7200
aatatgcacc tgccttcaga aagacaccag agtgcgcaat agcccacccc acagtgggct    7260
aacagccatg ggcccggtcc ccacaccgat ccggggcgcc ttcacgaccg caggcgtggt    7320
tctggagatg atcaaggacg tggaggctgc ggtctcaggc cgcaagggca ggagcggcac    7380
ggcggcgggc gacgtcgcct tccccaaggg gaaggagaac ctggcctccg tgctgaagcg    7440
gtacaagcgg cggctcgcca gcaagggcca gtagcgcgcg ggtgtcagac aggcaggcga    7500
tcgcaagcaa tgttaggagg agcctgacta ttgttctcca gggggggctgc cactggcgcc    7560
ggcctccctg agccctggat ttttttcgttg cacgacgttc ctaggaccg gtggttgccc    7620
gatggtcgtc ttggtccctt ccagcaggtt ttttttttcc ttccctcttt ctgtgggttt    7680
cttttgtgg gctttgtgat gttttgaaag gggcaactag ggtatgtgct cagaaggact    7740
caagatgtac acgcgaagat gtactagtct gctgatgcag cgttgtaaag tccacactct    7800
gcaggttaac ccttttgggg gccgtcaagt gttagtgcgt gccctatgta tgttaatcac    7860
ccctgcagag aggttgcgaa tactgaacta ctcacagacc tgcacctgtc gagatcgttt    7920
```

```
gtaatatccg acgtcttgtt cagaattgtt ctcactcttt tttgcccgtt gtgtaattta      7980
ccctgaaggg acttcaagta cgtgcttcgg caagcacggt cttgaaagaa aaaaaactgt      8040
tagcatcagt gagctgcctg ttgagcagta aaagagaata caatgtgagc tctcaactca      8100
aaagcgagat gtgtcacgcg cgtatctcaa gaagcattgg gccaaagctt tttatgccag      8160
gcaagagaga tgcttccaaa tggccggtcc gaaatgcagg aaatgatgag taatatggtt      8220
tggcaaacca cttccgt                                                    8237

<210> SEQ ID NO 41
<211> LENGTH: 3765
<212> TYPE: DNA
<213> ORGANISM: Zea mays
<220> FEATURE:
<223> OTHER INFORMATION: Zea mays ethylene receptor (ethylene
      insensitive receptor, EIN2-like), E2-25 coding sequence (CDS)

<400> SEQUENCE: 41
atggatgcac cggatgttca acagagcatg ggatataagg agtccagggg tggtatgcct        60 aagttttttcc atgcccttgg accagcactc ctgatttcaa tgggttacat tgatctcggg       120
aagtgggtgg cagccgttga agctggttct tgttttggat tcgacctggt gttgctggct       180
ctccttttca atttcactgc cattgtatgt cagtaccttg ctgcttgcat ggcactgtc         240 acagggaaga atcttgcaga gatatgccac caagagtaca ccagccaac atgtatattc         300 cttggtgttc aagctggatt gtctttgttg acgtcagagc tgagtatgat ttttggcata        360
gcactcggat tcaacctcct gtttgaatat gatgatctca tcacagggat atgctttgca        420
acagtgatgg aagggacaat aaatgcctgc atagcaggat ttgcacttct tagttatgtg        480
cttggcttat tggttagcca gccacaaatt cctctcacga tgaatgtaat attccccaag        540
atcagtggtg agagtgctta ctctctgatg gcgcttcttg gtgcaaacat aatggcacac        600
aacttctaca ttcattcatc aggtcagaaa aagtcatctg cagttggtct tggagcctta        660
tttcacgacc acctttttc aatattgttc attttttactg aatctttat ggtgaactat        720 gttctaatga actctgcagc agcggaatct actaatactc ttctcattac cttccaagat        780
gttgtagagc taatgaatca gatatttgta aaccctctgg caccaactat attttttagtg      840 gttcttctct tctccagcca catcatctcg ctgacatctg ctatcggtag ccaagtgatt        900
tcacaccatt tattcggtat aaaccttcct ctttctggac atcgtctcct actgaaggtt        960
tttgccatag ttcctactct gtactgggcg aaagttgcag gagctgaagg gatataccaa       1020
ttattaatta tgccagat tattcaagcc atgcttcttc catcttcagt cgtcccactt        1080
tttcgtgttg cttcatcaag atcaataatg ggagcccata gagtgtcttt gcatctggag      1140
atactggttt tcttgcatt tctccttatg ctattttcaa atatcatatt tgtggcagaa      1200
atgctatttg cgacagtgg gtggatgaac aatctgaaag gatatactgg aagccctgtg      1260
gtgctcccat ataccgtttt agtttagtt gcacttatat ctgtggcttt ttcactgtac      1320
ctggctgtta caccattgag atctggaagt catgaagctg aatcccatga atggtctgtg      1380
cattctcaga gagaactctt gaatacttct caagaaaggg aagatgttaa ggtggacaat      1440
gttacatatg aggaagatca agatcagat gttgtcccct ctcccaggga tgtgcctgac      1500
agccatccgg aactggcctt ggactatat gatacttctg acactgctgt agaatctgat      1560
cacgactctc aacaatctac tgcttatgca tccactgctc ctgaaacctg ctcctccccg      1620
tcgtttactc gcgaggagtc aaaatcagtt gttgcagtca actggccgga gcctttggag      1680
```

-continued

| | |
|---|---|
| aaggttccta cttctactgt gatggaggaa agcacagtag aaaatgtggt ctctaggatc | 1740 |
| acgactgaaa gagatgtttt agtagaaaca gatgttgtct cgggcaagga taaggaagat | 1800 |
| atccgtactt tggagtctga gaagtcaatt gttgatagca ccccatatgt gtctgatgac | 1860 |
| ggtccgccat cccttacttt cagcagggga aagggctcag atgcaggaaa tggcagtggt | 1920 |
| agtctctcaa ggttatctgg tttgggccgt gcagcaagga gacagctagc tgctactctt | 1980 |
| gatgagttct gggggcatct gtttgattac catggtaagc tcactcaaga agctagcacc | 2040 |
| aaaaagtttg gtatcttgct tgggatagac cttagaacac ctagcacatc tgtaagaacg | 2100 |
| gataaacaag ctgctgaaat acttaagagc ccactggtga gagactcaat gcgggggca | 2160 |
| gcttttttgt caagctcagt ggacatgatg tcccctaaga atgaaacgtc gaatttggaa | 2220 |
| cttgcatatg ggcttcagag gggacctggc atgggattgt caagctggtc tcagggtatg | 2280 |
| cagctaccaa atacacagct gcagagctca agcaatagcc tacttgagca gagtgcaaga | 2340 |
| ttaaactcaa attttagttc atcttattca gacaacaatc agttctacca acctgcaaca | 2400 |
| attcatggat accagctcac atcttacctg aaacagatga atgccagccc aagcctttac | 2460 |
| tctagcatgc cgctggaccc acaacggctt ccaaaatcat ctgtgtctgc tgtgccaaac | 2520 |
| tatgctgatt ccatgatgca tgctcgtaat cataacctgc ttgcttcact gggtggtact | 2580 |
| actacacagc ttcctgcaac atcccgcgta ggctcaatga tgcctgaaag atcgtattat | 2640 |
| gatccttcca gcgttgatgg gaatgaaaac gctggttcac ctgcttactc aaaaaagtac | 2700 |
| cacagctcac ctgatatgtc tggaataatc gctgcaagta gagctgcact cttgaatgaa | 2760 |
| gcaaagttgg gtgctgccat tggaccacag tcatacctca gcaggctggc ggcagaaaga | 2820 |
| tctcaatatg caagctcaac agccaggccc gcggctccat tagcatttga cgagcttttca | 2880 |
| cctcctaagc tccagagtga tatcttctcg gcgcagtcaa gcatgagacc aagtgctaga | 2940 |
| tcccttrggg ctaagcaacc atttgagcaa ttgttcggca tgtcaagtgc agagctcagt | 3000 |
| aaaggtgact tcaatcttcc aggcagatca ggtggcgtgg ccaaggatga tttctcttat | 3060 |
| aaggaatctg agacgaagct tcttcagtcc ctcaggctct gcatcatgaa gctccttaag | 3120 |
| ctagagggat caggtggct gttcaagcaa aatggtggtt gtgatgaaga tctaatcgac | 3180 |
| cgagtcgctg cagccgagaa gctattgatg caagggactg ccgagaatca actgctgctt | 3240 |
| catggtggtg atctccagca acattcttcc gaccaggccg gcatccagta catgcgcacg | 3300 |
| cttcccaact gcggggagga ctgtgtttgg cgcgcgtcac tcgtcgttag tttcggtgtc | 3360 |
| tggtgtgtcc gccgagtgct ggacatgtct ctggtggaaa gcaggccaga actttggggc | 3420 |
| aagtatacct atgtccttaa ccgtcttcag gggatcttgg accctgcgtt ctccaagcct | 3480 |
| cggggtgctc tgacaatatg cacctgcctt cagaaagaca ccagagtgcg caatagccca | 3540 |
| ccccacagtg ggctaacagc catgggcccg gtccccacac cgatccgggg cgccttcacg | 3600 |
| accgcaggcg tggttctgga gatgatcaag gacgtggagg ctgcggtctc aggccgcaag | 3660 |
| ggcaggagcg gcacggcggc gggcgacgtc gccttcccca aggggaagga gaacctggcc | 3720 |
| tccgtgctga gcggtacaa gcggcggctc gccagcaagg gccag | 3765 |

<210> SEQ ID NO 42
<211> LENGTH: 1255
<212> TYPE: PRT
<213> ORGANISM: Zea mays
<220> FEATURE:
<223> OTHER INFORMATION: Zea mays ethylene receptor (ethylene
      insensitive receptor, EIN2-like), E2-25 protein

<400> SEQUENCE: 42

-continued

```
Met Asp Ala Pro Asp Val Gln Gln Ser Met Gly Tyr Lys Glu Ser Arg
  1               5                  10                  15

Gly Gly Met Pro Lys Phe Phe His Ala Leu Gly Pro Ala Leu Leu Ile
             20                  25                  30

Ser Met Gly Tyr Ile Asp Leu Gly Lys Trp Val Ala Val Glu Ala
         35                  40                  45

Gly Ser Cys Phe Gly Phe Asp Leu Val Leu Ala Leu Leu Phe Asn
     50                  55                  60

Phe Thr Ala Ile Val Cys Gln Tyr Leu Ala Ala Cys Ile Gly Thr Val
 65                  70                  75                  80

Thr Gly Lys Asn Leu Ala Glu Ile Cys His Gln Glu Tyr Asn Gln Pro
                 85                  90                  95

Thr Cys Ile Phe Leu Gly Val Gln Ala Gly Leu Ser Leu Leu Thr Ser
                100                 105                 110

Glu Leu Ser Met Ile Phe Gly Ile Ala Leu Gly Phe Asn Leu Leu Phe
            115                 120                 125

Glu Tyr Asp Asp Leu Ile Thr Gly Ile Cys Phe Ala Thr Val Met Glu
        130                 135                 140

Gly Thr Ile Asn Ala Cys Ile Ala Gly Phe Ala Leu Leu Ser Tyr Val
145                 150                 155                 160

Leu Gly Leu Leu Val Ser Gln Pro Gln Ile Pro Leu Thr Met Asn Val
                165                 170                 175

Ile Phe Pro Lys Ile Ser Gly Glu Ser Ala Tyr Ser Leu Met Ala Leu
                180                 185                 190

Leu Gly Ala Asn Ile Met Ala His Asn Phe Tyr Ile His Ser Ser Gly
            195                 200                 205

Gln Lys Lys Ser Ala Val Gly Leu Gly Ala Leu Phe His Asp His
        210                 215                 220

Leu Phe Ser Ile Leu Phe Ile Phe Thr Gly Ile Phe Met Val Asn Tyr
225                 230                 235                 240

Val Leu Met Asn Ser Ala Ala Ala Glu Ser Thr Asn Thr Leu Leu Ile
                245                 250                 255

Thr Phe Gln Asp Val Val Glu Leu Met Asn Gln Ile Phe Val Asn Pro
                260                 265                 270

Leu Ala Pro Thr Ile Phe Leu Val Val Leu Phe Ser Ser His Ile
            275                 280                 285

Ile Ser Leu Thr Ser Ala Ile Gly Ser Gln Val Ile Ser His His Leu
    290                 295                 300

Phe Gly Ile Asn Leu Pro Leu Ser Gly His Arg Leu Leu Lys Val
305                 310                 315                 320

Phe Ala Ile Val Pro Thr Leu Tyr Trp Ala Lys Val Ala Gly Ala Glu
                325                 330                 335

Gly Ile Tyr Gln Leu Leu Ile Ile Cys Gln Ile Ile Gln Ala Met Leu
            340                 345                 350

Leu Pro Ser Ser Val Val Pro Leu Phe Arg Val Ala Ser Ser Arg Ser
            355                 360                 365

Ile Met Gly Ala His Arg Val Ser Leu His Leu Glu Ile Leu Val Phe
        370                 375                 380

Leu Ala Phe Leu Leu Met Leu Phe Ser Asn Ile Ile Phe Val Ala Glu
385                 390                 395                 400

Met Leu Phe Gly Asp Ser Gly Trp Met Asn Asn Leu Lys Gly Tyr Thr
                405                 410                 415

Gly Ser Pro Val Val Leu Pro Tyr Thr Val Leu Val Leu Val Ala Leu
```

```
                420             425             430
Ile Ser Val Ala Phe Ser Leu Tyr Leu Ala Val Thr Pro Leu Arg Ser
            435                 440                 445
Gly Ser His Glu Ala Glu Ser His Glu Trp Ser Val His Ser Gln Arg
            450                 455                 460
Glu Leu Leu Asn Thr Ser Gln Glu Arg Glu Asp Val Lys Val Asp Asn
465                 470                 475                 480
Val Thr Tyr Glu Glu Asp Gln Arg Ser Asp Val Val Pro Ser Pro Arg
                485                 490                 495
Asp Val Pro Asp Ser His Pro Glu Leu Ala Leu Asp Tyr Ile Asp Thr
            500                 505                 510
Ser Asp Thr Ala Val Glu Ser Asp His Asp Ser Gln Gln Ser Thr Ala
            515                 520                 525
Tyr Ala Ser Thr Ala Pro Glu Thr Cys Ser Ser Pro Ser Phe Thr Arg
            530                 535                 540
Glu Glu Ser Lys Ser Val Val Ala Val Asn Trp Pro Glu Pro Leu Glu
545                 550                 555                 560
Lys Val Pro Thr Ser Thr Val Met Glu Glu Ser Thr Val Glu Asn Val
                565                 570                 575
Val Ser Arg Ile Thr Thr Glu Arg Asp Val Leu Val Glu Thr Asp Val
            580                 585                 590
Val Ser Gly Lys Asp Lys Glu Asp Ile Arg Thr Leu Glu Ser Glu Lys
            595                 600                 605
Ser Ile Val Asp Ser Thr Pro Tyr Val Ser Asp Asp Gly Pro Pro Ser
            610                 615                 620
Leu Thr Phe Ser Arg Gly Lys Gly Ser Asp Ala Gly Asn Gly Ser Gly
625                 630                 635                 640
Ser Leu Ser Arg Leu Ser Gly Leu Gly Arg Ala Ala Arg Arg Gln Leu
                645                 650                 655
Ala Ala Thr Leu Asp Glu Phe Trp Gly His Leu Phe Asp Tyr His Gly
            660                 665                 670
Lys Leu Thr Gln Glu Ala Ser Thr Lys Lys Phe Gly Ile Leu Leu Gly
            675                 680                 685
Ile Asp Leu Arg Thr Pro Ser Thr Ser Val Arg Thr Asp Lys Gln Ala
            690                 695                 700
Ala Glu Ile Leu Lys Ser Pro Leu Val Arg Asp Ser Met Arg Gly Ala
705                 710                 715                 720
Ala Phe Leu Ser Ser Ser Val Asp Met Met Ser Pro Lys Asn Glu Thr
                725                 730                 735
Ser Asn Leu Glu Leu Ala Tyr Gly Leu Gln Arg Gly Pro Gly Met Gly
            740                 745                 750
Leu Ser Ser Trp Ser Gln Gly Met Gln Leu Pro Asn Thr Gln Leu Gln
            755                 760                 765
Ser Ser Ser Asn Ser Leu Leu Glu Gln Ser Ala Arg Leu Asn Ser Asn
            770                 775                 780
Phe Ser Ser Ser Tyr Ser Asp Asn Asn Gln Phe Tyr Gln Pro Ala Thr
785                 790                 795                 800
Ile His Gly Tyr Gln Leu Thr Ser Tyr Leu Lys Gln Met Asn Ala Ser
                805                 810                 815
Pro Ser Leu Tyr Ser Ser Met Pro Leu Asp Pro Gln Arg Leu Pro Lys
            820                 825                 830
Ser Ser Val Ser Ala Val Pro Asn Tyr Ala Asp Ser Met Met His Ala
            835                 840                 845
```

-continued

```
Arg Asn His Asn Leu Leu Ala Ser Leu Gly Gly Thr Thr Thr Gln Leu
    850                 855                 860

Pro Ala Thr Ser Arg Val Gly Ser Met Met Pro Glu Arg Ser Tyr Tyr
865                 870                 875                 880

Asp Pro Ser Ser Val Asp Gly Asn Glu Asn Ala Gly Ser Pro Ala Tyr
                885                 890                 895

Ser Lys Lys Tyr His Ser Ser Pro Asp Met Ser Gly Ile Ile Ala Ala
            900                 905                 910

Ser Arg Ala Ala Leu Leu Asn Glu Ala Lys Leu Gly Ala Ala Ile Gly
        915                 920                 925

Pro Gln Ser Tyr Leu Ser Arg Leu Ala Ala Arg Ser Gln Tyr Ala
    930                 935                 940

Ser Ser Thr Ala Arg Pro Ala Ala Pro Leu Ala Phe Asp Glu Leu Ser
945                 950                 955                 960

Pro Pro Lys Leu Gln Ser Asp Ile Phe Ser Ala Gln Ser Ser Met Arg
                965                 970                 975

Pro Ser Ala Arg Ser Leu Trp Ala Lys Gln Pro Phe Glu Gln Leu Phe
            980                 985                 990

Gly Met Ser Ser Ala Glu Leu Ser Lys Gly Asp Phe Asn Leu Pro Gly
        995                 1000                1005

Arg Ser Gly Gly Val Ala Lys Asp Asp Phe Ser Tyr Lys Glu Ser Glu
    1010                1015                1020

Thr Lys Leu Leu Gln Ser Leu Arg Leu Cys Ile Met Lys Leu Leu Lys
1025                1030                1035                1040

Leu Glu Gly Ser Gly Trp Leu Phe Lys Gln Asn Gly Gly Cys Asp Glu
                1045                1050                1055

Asp Leu Ile Asp Arg Val Ala Ala Ala Glu Lys Leu Leu Met Gln Gly
            1060                1065                1070

Thr Ala Glu Asn Gln Leu Leu Leu His Gly Gly Asp Leu Gln Gln His
        1075                1080                1085

Ser Ser Asp Gln Ala Gly Ile Gln Tyr Met Arg Thr Leu Pro Asn Cys
    1090                1095                1100

Gly Glu Asp Cys Val Trp Arg Ala Ser Leu Val Val Ser Phe Gly Val
1105                1110                1115                1120

Trp Cys Val Arg Arg Val Leu Asp Met Ser Leu Val Glu Ser Arg Pro
                1125                1130                1135

Glu Leu Trp Gly Lys Tyr Thr Tyr Val Leu Asn Arg Leu Gln Gly Ile
            1140                1145                1150

Leu Asp Pro Ala Phe Ser Lys Pro Arg Gly Ala Leu Thr Ile Cys Thr
        1155                1160                1165

Cys Leu Gln Lys Asp Thr Arg Val Arg Asn Ser Pro Pro His Ser Gly
    1170                1175                1180

Leu Thr Ala Met Gly Pro Val Pro Thr Pro Ile Arg Gly Ala Phe Thr
1185                1190                1195                1200

Thr Ala Gly Val Val Leu Glu Met Ile Lys Asp Val Glu Ala Ala Val
                1205                1210                1215

Ser Gly Arg Lys Gly Arg Ser Gly Thr Ala Ala Gly Asp Val Ala Phe
            1220                1225                1230

Pro Lys Gly Lys Glu Asn Leu Ala Ser Val Leu Lys Arg Tyr Lys Arg
        1235                1240                1245

Arg Leu Ala Ser Lys Gly Gln
    1250                1255

<210> SEQ ID NO 43
```

```
<211> LENGTH: 26
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN2-like, ZmEIN2-25) E2-25 forward primer

<400> SEQUENCE: 43
tgggtggtac tactacacag cttcct                                          26

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN2-like, ZmEIN2-25) E2-25 reverse primer

<400> SEQUENCE: 44
aggcttggag aacgcagggt ccaaga                                          26

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN3-like, ZmEIN3-2) EIN3-2 forward primer

<400> SEQUENCE: 45
acccccgtac aagaagcctc atga                                            24

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN3-like, ZmEIN3-2) EIN3-2 reverse primer

<400> SEQUENCE: 46
gtttatggct ggccggacat acaagt                                          26

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN3-like, ZmEIN3-3) EIN3-3 forward primer

<400> SEQUENCE: 47
acccccgtac aagaagcctc atga                                            24

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN3-like, ZmEIN3-3) EIN3-3 reverse primer

<400> SEQUENCE: 48
```

```
acgaccaaga ccctatagac tcgacactc                                    29

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:oligo-dT(20)
      primer

<400> SEQUENCE: 49
tttttttttt tttttttttt                                              20

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence:ACOR1 primer

<400> SEQUENCE: 50
cctcgaaccg tggctccttg gcctcgaact t                                 31
```

NUCLEIC ACIDS THAT ENCODE ERS1 FROM MAIZE AND THEIR USES

STATEMENT AS TO RIGHTS TO INVENTIONS MADE UNDER FEDERALLY SPONSORED RESEARCH AND DEVELOPMENT

This invention was made with government support under grants 97-35304-4657 and 98-35100-6150 awarded by the United States Department of Agriculture, and grant 0076434 awarded by the National Science Foundation. The government has certain rights in the invention.

FIELD OF THE INVENTION

The present invention is directed to plant genetic engineering. In particular, it is directed to producing green leaves in maize through inhibition of ethylene. The genes involved in producing this phenotype include 1-Aminocyclopropane-1-Carboxylate ("ACC") oxidase, ACC deaminase, ethylene response sensor ("ERS"), ethylene resistant ("ETR"), and ethylene insensitive ("EIN").

BACKGROUND OF THE INVENTION

Programmed cell death (PCD) is integral to the development of multicellular organisms including plants. Numerous reports of plant PCD have appeared in the literature in the last 5 years and include examples that occur as part of the response to pathogen attack: e.g., the hypersensitive response (reviewed in Greenberg, et al., *Proc. Natl. Acad. Sci. USA* 93:12094-12097 (1996); Pennell and Lamb, et al., *Plant Cell* 9:1157-1168 (1997); Richberg et al., *Curr. Op. Biol.* 1:480-485 (1998); Lam et al., *Curr. Op. Biol.* 2:502-507 (1999)); the response to abiotic stress: e.g., formation of aerenchyma in hypoxic roots (reviewed in Drew, *Annu. Rev. Plant Physiol. Plant Mol. Biol.* 48:223-250 (1997); Drew et al., *Trends Plant Sci.* 5:123-127 (2000)); or as part of a normal developmental program: e.g., endosperm cell death during tracheary differentiation (Fukuda, *Plant Cell* 9:1147-1156 (1997); Groover and Jones, *Plant Physiol.* 119:375-384 (1999)), cereal seed development (Young et al., *Plant Physiol.* 119:737-751 (1997); Young and Gallie, *Plant Mol. Biol.* 39:915-926 (1999); Young and Gallie, *Plant Mol. Biol.* 42:397-414 (2000)), or aleurone cell death during late cereal seed germination (Kuo et al., *Plant Cell* 8:259-269 (1996); Bethke et al., *Plant Cell* 11:1033-1045 (1999); Wang et al., *Plant Mol. Biol.* 32:1125-1134 (1996)). During maize kernel development, the endosperm undergoes a progressive cell death that engulfs the entire tissue, leaving only the aleurone layer viable at maturity (Bartels et al., *Planta* 175:485-492 (1988); Kowles and Phillips, *Int. Rev. Cytol.* 112:97-136 (1988); Lopes and Larkins, *Plant Cell* 5:1383-1399 (1993); Young et al., *Plant Physiol.* 119:737-751 (1997); Young and Gallie, *Plant Mol. Biol.* 39:915-926 (1999)).

Ethylene is known to be a regulator of PCD during plant development (Campbell and Drew, *Planta* 157:350-357 (1983); Drew et al., *Planta* 147:83-88 (1979); He et al., *Plant Physiol.* 112:1679-1685 (1996)) and plays a role in orchestrating programmed cell death in developing cereal endosperm: exogenous ethylene can accelerate the onset of the cell death program in developing endosperm whereas inhibitors of ethylene biosynthesis or perception delay the program (Young et al., *Plant Physiol.* 119:737-751 (1997); Young and Gallie, *Plant Mol. Biol.* 39:915-926 (1999); Young and Gallie, *Plant Mol. Biol.* 42:397-414 (2000)). Ethylene controls many aspects of plant growth and development such as fruit development, root and leaf growth and seed germination. As shown in Figure 1, ethylene is generated from methionine by conversion of S-adenosyl-L-methionine to the cyclic amino acid 1-aminocyclopropane-1-carboxylic acid (ACC) which is facilitated by ACC synthase (Yang and Hoffman, *Annu. Rev. Plant Physiol.* 35:155-189 (1984)). Ethylene ($C_2H_4$) is then produced from the oxidation of ACC through the action of ACC oxidase. ACC synthase and ACC oxidase are encoded by multigene families in which individual members exhibit tissue-specific regulation and/or are induced in response to environmental and chemical stimuli. (reviewed in Fluhr and Mattoo, *Crit. Rev. Plant Sci.* 15: 479-523 (1996); Kende, *Annu. Rev. Plant Physiol* 44:283-307 (1993); Zarembinski and Theologis, *Plant Mol. Biol.* 26:1579-1597 (1994)).

Enzymes that degrade the compounds produced by the ethylene biosynthesis pathway are also known. Two enzymes in particular, ACC deaminase and ACC malonyl transferase, are commonly found in bacteria and can lower the concentration of ACC in the cell. ACC deaminase accomplishes this by converting ACC to α-ketobutyrate and ammonia. Nucleic acids encoding this enzyme have been used to control fruit ripening in plants (U.S. Pat. No. 5,702,933). Endogenous ACC concentration is also lowered by forming the metabolically inert compound, N-malonyl-ACC, in a reaction catalyzed by ACC N-malonyltransferase (MTase). (Liu et al., *Phytochemistry* 40:691-697 (1995)).

Ethylene perception involves membrane-localized receptors that, in *Arabidopsis*, include ETR1, ERS1, ETR2, ERS2 and EIN4 (Chang et al., *Science* 262:539-544 (1993); Hua et al, *Science* 269:1712-1714 (1995), Hua et al., *Plant Cell* 10:1321-1332 (1998), Sakai et al., *Proc. Natl. Acad. Sci. USA* 95:5812-5817 (1998)). ETR1, ETR2 and EIN4 are composed of three domains, an N-terminal ethylene binding domain (Schaller and Bleeker, *Science* 270:1809-1811 (1995)), a putative histidine protein kinase domain, and a C-terminal received domain whereas ERS1 and ERS2 lack the receiver domain. These genes have been grouped into two subfamilies based on homology, where ETR1 and ERS1 comprise one subfamily and ETR2, ERS2, and EIN4 comprise the other (Hua et al., *Plant Cell* 10:1321-1332 (1998)). These receptors exhibit sequence similarity to bacterial two-component regulators (Chang et al., *Science* 262:539-544 (1993)) which act as sensors and transducers of environmental signals (Parkinson and Kofoid, *Annu. Rev. Genet.* 26:71-112 (1992)) and as sensors in yeast and Dictyostelium that are involved in osmotic regulation (Maeda et al., *Nature* 369:242-245 (1994); Schuster et al., *EMBO J.* 15:3880-3889 (1996)).

In *Arabidopsis*, analysis of loss-of-function mutants has revealed that ethylene inhibits the signaling activity of these receptors and subsequently their ability to activate CTR1, a negative regulator of ethylene responses that is related to mammalian RAF-type serine/threonine kinases (Kieber et al, *Cell* 72:427-441 (1993)). Current understanding of the ethylene signal transduction pathway suggests that ethylene binding to the receptor inhibits its own kinase activity, resulting in decreased activity of CTR1, and consequently, an increase in EIN2 activity (which acts downstream of CTR1) that ultimately leads to an increase in ethylene responsiveness (Bleeker and Schaller, *Plant Physiol.* 111:653-660 (1996); Hua and Meyerowitz, *Cell* 72:427-441 (1998)). Differential expression of members of the ethylene receptor family has been observed, both developmentally and in response to ethylene (Hua et al., *Plant Cell* 10:1321-1332 (1998); Lashbrook et al., *The Plant J* 15:243-252 (1998)).

Because ethylene plays such a large role in plant growth and development, the identification of genes involved in the ethylene synthesis pathway is useful for creating plants with phenotypes associated with an altered ethylene-related process, such as plants having staygreen traits. The synthesis of ethylene, its perception by ethylene receptors, and its downstream signaling components have been identified in *Arabidopsis* and some other plant species. Prior to the advent of the present invention, however, no maize gene involved in ethylene bioysnthesis or signal transduction had been reported. Accordingly, a need exists for the identification of genes involved in the maize ethylene biosynthesis and signal transduction pathways. This invention meets this and other needs by providing, ACC oxidase, ACC deaminase, ERS1, ETR2, and EIN2 as well as methods of their use.

BRIEF SUMMARY OF THE INVENTION

The present invention provides compositions and methods which affect ethylene biosynthesis or the signal transduction pathway of ethylene in plants.

In a first aspect, the invention provides for an isolated nucleic acid which can encode a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41) wherein the isolated nucleic acid is at least 90% identical to the polynucleotide sequence.

In a second aspect, the invention provides a recombinant expression cassette comprising a promoter sequence operably linked to a nucleic acid sequence encoding a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41), wherein the isolated nucleic acid is at least 90% identical to the polynucleotide sequence or a fragment thereof.

In a third aspect, the invention provides a transgenic plant comprising a recombinant expression cassette comprising a promoter sequence operably linked to a nucleic acid sequence encoding a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41), wherein the isolated nucleic acid is at least 90% identical to the polynucleotide sequence or a fragment thereof.

In a fourth aspect, the invention provides a method of inhibiting ACC oxidase, or EIN2 activity in a plant, the method comprising introducing a construct comprising a promoter operably linked to a nucleic acid sequence encoding a polynucleotide sequence such as ACC oxidase (represented by SEQ ID NOs: 2, 7, 11, and 16), or EIN2 (represented by SEQ ID NO: 41) wherein the isolated nucleic acid is at least 90% identical to the polynucleotide sequence or a fragment thereof.

In a fifth aspect, the invention provides a method of increasing ACC deaminase, ERS, or ETR activity in a plant, the method comprising introducing a construct comprising a promoter operably linked to a nucleic acid sequence encoding a polynucleotide sequence such as ACC deaminase, ERS (represented by SEQ ID NOs: 21 and 26), or ETR (represented by SEQ ID NOs: 31 and 36) wherein the isolated nucleic acid is at least 90% identical to the polynucleotide sequence or a fragment thereof.

Other objects, advantages and embodiments of the invention will be apparent from review of the Detailed Description that follows.

BRIEF DESCRIPTION OF THE DRAWINGS

NOT APPLICABLE

DETAILED DESCRIPTION OF THE INVENTION

A. Introduction

The present invention provides new methods of delaying senescence in a maize plant by inhibiting ACC oxidase, or EIN2 activity in the plant. The delay in senescence can also be achieved through the production of ACC deaminase, mutated ETR1 and ERS2 proteins, as well as overexpression of wild-type ETR1 and ERS2 proteins. The present invention also provides methods for selecting for a maize plant with a delayed senescence pattern or characteristic. A delayed senescence pattern will result in a maize plant with an altered phenotype as compared to a wild type plant. An altered phenotype includes, but is not limited to, staygreen traits, e.g., leaves that remain green late in the growing season, improved drought tolerance, improved silage, increased grain yield, and increased tolerance to planting at higher densities, and kernels with multiple embryos. Accordingly, by inhibiting ACC oxidase, or EIN2 activity in a plant, or through the production of ACC deaminase, mutated ETR1 and ERS2 proteins, as well as overexpression of wild-type ETR1 and ERS2 proteins, a plant with increased biomass and/or yield can be identified.

B. Definitions

The phrase "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read through by a polymerase and do not alter the expression of a polypeptide encoded by that nucleic acid.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, bryophytes, and multicellular algae. It includes plants of a variety of ploidy levels, including aneuploid, polyploid, diploid, haploid and hemizygous.

The phrase "host cell" refers to a cell from any organism. Preferred host cells are derived from plants, bacteria, yeast, fungi, insects or other animals. Methods for introducing polynucleotide sequences into various types of host cells are well known in the art.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like.

An "ACC oxidase polynucleotide" is a nucleic acid sequence comprising a coding region of about 50 to about 6800 nucleotides, sometimes from about 100 to about 3000 nucleotides and sometimes from about 300 to about 1300 nucleotides, which hybridizes to SEQ ID NOs: 2, 7, 12, and 17 under stringent conditions (as defined below), which comprises at least 20, typically 50, contiguous nucleotides of these sequences, or which encodes an ACC oxidase polypeptide or fragment of at least 15 contiguous amino acids thereof. ACC oxidase polynucleotides are typically at least about 90% identical to the exemplified sequences.

An "ACC oxidase polypeptide" or "ACC oxidase protein" has a sequence of about 50 to about 400, sometimes 100 to 150, and preferably between 310 and 330 amino acid residues encoded by an ACC oxidase polynucleotide. ACC oxidase polypeptides are involved in ethylene biosynthesis and are exemplified by SEQ ID NOs: 3, 8, 12, and 17.

An "ERS1 polynucleotide" is a nucleic acid sequence comprising a coding region of about 50 to about 4000 nucleotides, sometimes from about 1000 to about 3000 nucleotides and sometimes from about 1600 to about 2000 nucleotides, which hybridizes to SEQ ID NOs: 21 or 26 under stringent conditions (as defined below), which comprises at least 20, typically 50, contiguous nucleotides of these sequences, or which encodes an ERS1 polypeptide or fragment of at least 15 contiguous amino acids thereof. ERS1 polynucleotides are typically at least about 90% identical to the exemplified sequences.

An "ERS1 polypeptide" or "ERS1 protein" has a sequence of about 75 to about 1000, sometimes 200 to 700, and preferably 634 amino acid residues encoded by an ERS1 polynucleotide. ERS1 polypeptides are involved in ethylene biosynthesis and are exemplified by SEQ ID NOs: 22 and 27.

An "ETR2 polynucleotide" is a nucleic acid sequence comprising a coding region of about 50 to about 6800 nucleotides, sometimes from about 1000 to about 3000 nucleotides and sometimes from about 2200 to about 2400 nucleotides, which hybridizes to SEQ ID NOs: 31 or 36 under stringent conditions (as defined below), which comprises at least 20, typically 50, contiguous nucleotides of these sequences, or which encodes an ETR2 polypeptide or fragment of at least 15 contiguous amino acids thereof. ETR2 polynucleotides are typically at least about 90% identical to the exemplified sequences.

An "ETR2 polypeptide" or "ETR2 protein" has a sequence of about 100 to about 900, sometimes 300 to 800, and preferably between 765 and 770 amino acid residues encoded by an ETR2 polynucleotide. ETR2 polypeptides are involved in ethylene biosynthesis and are exemplified by SEQ ID NOs: 32 and 37.

An "EIN2 polynucleotide" is a nucleic acid sequence comprising a coding region of about 1000 to about 9000 nucleotides, sometimes from about 5000 to about 8500 nucleotides and sometimes from about 8100 to about 8400 nucleotides, which hybridizes to SEQ ID NO: 42 under stringent conditions (as defined below), which comprises at least 20, typically 50, contiguous nucleotides of these sequences, or which encodes an EIN2 polypeptide or fragment of at least 15 contiguous amino acids thereof. EIN2 polynucleotides are typically at least about 90% identical to the exemplified sequences.

An "EIN2 polypeptide" or "EIN2 protein" has a sequence of about 50 to about 1500, sometimes 500 to 1400, and preferably 1255 amino acid residues encoded by an EIN2 polynucleotide. EIN2 polypeptides are involved in ethylene biosynthesis and are exemplified by SEQ ID NO: 42.

"Increased or enhanced expression or activity" of a particular polypeptide or nucleic acid of the invention refers to an augmented change in activity of the polypeptide. Examples of such increased activity or expression include the following: Activity of the polypeptide or expression of the gene encoding the polypeptide is increased above the level (or is present for a loner period of time) of that in wild-type, non-transgenic control plants. Activity of a polypeptide or expression of a gene is present in an organ, tissue or cell where it is not normally detected in wild-type, non-transgenic control plants (i.e. spatial distribution of a polypeptide or expression of the gene encoding the polypeptide is altered).

"Decreased expression or activity" of a polypeptide or nucleic acid of the invention refers to a decrease in activity of the polypeptide. Examples of such decreased activity or expression include the following: Activity of the polypeptide or expression of the gene is decreased below the level of that in a wild-type, non-transgenic control plant.

The term "reproductive structures" or "reproductive tissues" as used herein includes fruit, ovules, seeds, pollen, flowers, or flower parts such as pistils, stamens, anthers, sepals, petals, carpels, or any embryonic tissue.

The term "vegetative structures" or "vegetative tissues" as used herein includes leaves, stems, tubers, roots, vascular tissue, or root and shoot meristem.

An "expression cassette" refers to a nucleic acid construct, which when introduced into a host cell, results in transcription and/or translation of a RNA or polypeptide, respectively. Antisense or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy, a number of polynucleotide sequences will encode the same polypeptide. These variants are specifically covered by the term "polynucleotide sequence from a gene of the invention". In addition, the term specifically includes sequences (e.g., full length sequences) substantially identical (determined as described below) with a gene sequence encoding an peptide of the invention, and that encode proteins that retain the function of a peptide of the invention.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman, *Add. APL. Math.* 2:482 (1981), by the homology alignment algorithm of Needle man and Wunsch, *J. Mol. Biol.* 48:443 (1970), by the search for similarity method of Pearson and Lipman, *Proc. Natl. Acad. Sci. U.S.A.* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 85% sequence identity. Alternatively, percent identity can be any integer from 85% to 100%. More preferred embodiments include at least: 85%, 90%, 95%, or 99%. compared to a reference sequence using the programs described herein; preferably BLAST using standard parameters, as described below. Accordingly, sequences encoding a polypeptide used in the methods of the present invention include nucleic acid sequences that have substantial identity to the sequences disclosed here. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 90%. Preferred percent identity of polypeptides can be any integer from 90% to 100%. More preferred embodiments include at least 90%, 95%, or 99%. Polypeptides that are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (™) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. or 65° C.

For the purposes of this disclosure, stringent conditions for hybridizations are those which include at least one wash in 0.2×SSC at 63° C. for 20 minutes, or equivalent conditions. Moderately stringent conditions include at least one wash (usually 2) in 0.2×SSC at a temperature of at least about 50° C., usually about 55° C., for 20 minutes, or equivalent conditions.

The phrase "phenotype associated with an ethylene-related process" refers to a phenotype that is modulated by ethylene. Exemplary phenotypes include, but are not limited to, staygreen traits, such as improved drought tolerance, improved silage, leaves that stay green later in the season, and increased tolerance to planting at higher densities. Modulation of ethylene-related processes can result from, e.g., overproduction of ethylene, underproduction of ethylene, increased sensitivity to ethylene in a cell or decreased sensitivity to ethylene in a cell.

The term "staygreen" refers to the ability of a hybrid plant to maintain plant health later into the growing season as compared to a wild type plant. Staygreen traits have been associated with increased grain yield, improved drought tolerance, improved silage and an increase in tolerance to planting at higher densities.

C. Isolation of Nucleic Acids Used in the Present Invention

The invention provides for an isolated nucleic acid which can encode a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41) wherein the isolated nucleic acid is at least 90% identical to the polynucleotide sequence. In an exemplary embodiment, the polynucleotide sequence is selected from the group consisting of SEQ ID NOs: 2, 7, 11, 16, 21, 26, 31, 36 and 41.

The isolation of nucleic acids used in the present invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of embryo-specific cDNAs, mRNA is isolated from embryos and a cDNA library that contains the gene transcripts is prepared from the mRNA.

The cDNA or genomic library can then be screened using a probe based upon the sequence of a cloned embryo-specific gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology can be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying genes encoding polypeptides of the invention from plant tissues are generated from comparisons of the sequences provided herein. For a general overview of PCR see PCR Protocols: A Guide to Methods and Applications. (Innis, M., Gelfand, D., Sninsky, J. and White, T., eds.), Academic Press, San Diego (1990). For example, appropriate primers for amplification of the genomic region of ACC oxidase include the following primer pairs: SEQ ID NO: 4 and SEQ ID NO: 5. The other primers disclosed here also are conveniently used by one of skill to prepare of the nucleic acids of the invention. The amplification conditions are typically as follows. Reaction components: 10 mM Tris HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per mL Taq polymerase. Program: 96° C. for 3 min., 30 cycles of 96° C. for 45 sec., 50° C. for 60 sec., 72° C. for 60 sec., followed by 72° C. for 5 min.

Polynucleotides may also be synthesized by well-known techniques as described in the technical literature. See, e.g., Carruthers et al., *Cold Spring Harbor Symp. Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

The genus of sequences of the present invention include genes and gene products identified and characterized by analysis using the nucleic acid sequences, including SEQ ID NOs: 1-2, 6-7, 11, 15-16, 20-21, 25-26, 30-31, 35-36, and 40-41, and protein sequences, including SEQ ID NOs: 3, 8, 12, 17, 22, 27, 32, 37, and 42. Sequences encoding the polynucleotides used in the present invention include nucleic acid sequences having substantial identity to SEQ ID NOs: 1-2, 6-7, 11, 15-16, 20-21, 25-26, 30-31, 35-36, and 40-41. Sequences encoding the polypeptides used in the present invention include polypeptide sequences having substantial identity to SEQ ID NOs: 3, 8, 12, 17, 22, 27, 32, 37, and 42.

Once a nucleic acid is isolated using the method described above, standard methods can be used to determine if the nucleic acid encodes ACC oxidase, ERS, ETR, or EIN2 polypeptides. A nucleic acid that encodes a polypeptide of the invention can be used to create a transgenic plant having staygreen traits. A transgenic plant having enhanced or increased expression to, for example, ACC oxidase polypeptide identical or substantially identical to SEQ ID NOs: 3, 8, 12, or 17 will display a phenotype associated with an altered ethylene process within the plant, e.g., delayed senescence.

Using standard methods, the skilled practitioner can compare the sequence of a putative nucleic acid sequence thought to encode, for example, an ACC oxidase polypeptide to a nucleic acid sequence encoding an ACC oxidase polypeptide to determine if the putative nucleic acid encodes an actual ACC oxidase polypeptide. A nucleic acid that encodes an ACC oxidase polypeptide, e.g., nucleic acids comprising sequences identical or substantially identical to SEQ ID NOs: 1-2, 6-7, 11, 15-16 can be used in the methods of the present invention.

D. Enhancing Expression of the Peptides of the Invention

Using specified promoters, the skilled practitioner can direct the expression of an ACC oxidase, ACC deaminase, ERS, ETR, or EIN2 peptide and create a plant with desirable phenotypic characteristics, e.g., staygreen traits. The skilled practitioner can choose from a variety of known promoters, whether constitutive, inducible, tissue-specific, and the like to drive expression of the gene encoding an ACC oxidase, ACC deaminase, ERS, ETR, or EIN2 peptide.

Any phenotypic characteristic caused by alteration of an ethylene-related process in a plant can be selected for in the present invention. For example, after introducing a polynucleotide encoding an ACC oxidase polypeptide, operably linked to a desirable promoter, e.g., constitutive, tissue specific, or inducible, in a plant, and regenerating the plant by standard procedures, a skilled practitioner can use standard methods to determine if the transgenic plant is a transgenic plant of the present invention, e.g., by comparing the transgenic plant to a wild type plant and looking for a phenotype associated with an altered ethylene-related process.

Enhancing or increasing expression of endogenous genes encoding enzymes involved in the ethylene biosynthesis pathway such as ACC oxidase may modulate an ethylene-related process in a plant by a variety of pathways. Alternatively, heterologous genes, such as ACC deaminase can be used. The particular pathway used to modulate an ethylene-related process is not critical to the present invention. For example, overexpression of an ACC oxidase polypeptide in a plant may affect ethylene-related processes by increasing ethylene levels in a plant and increasing sensitivity to ethylene in a plant.

Enhancing or increasing expression of genes encoding enzymes involved in ethylene signal transduction such as ERS, ETR, or EIN2 may also modulate an ethylene-related process in a plant by a variety of pathways. For example, increased expression of wild-type ERS or ETR subunits can increase the population of active ERS and ETR receptors in the plant cell and therefore inhibit ethylene detection and prevent the onset of senescence. In another example, enhancing the expression of genes encoding dominant negative mutations in ERS and ETR subunits can inhibit ethylene detection and prevent the onset of senescence.

Any number of means well known in the art can be used to modulate activity of an ACC oxidase, ERS, ETR, or EIN2 peptide in a plant. For example, the sequences, as described herein, can be used to prepare expression cassettes that enhance or increase endogenous gene expression. Where overexpression of a gene is desired, the desired gene from a different species may be used to decrease potential sense suppression effects. For example, enhanced expression of polynucleotides encoding ERS or ETR peptides are useful, for example, in order to increase the population of ERS or ETR receptors on the cell surface which will correspondingly lead to an increase in staygreen traits.

Any organ can be targeted for overexpression of a peptide of the invention such as shoot vegetative organs/structures (e.g., leaves, stems, and tubers), roots, flowers, and floral or reproductive organs/structures (e.g., bracts, sepals, petals, stamens, carpels, anthers and ovules), seed (including embryo, endosperm, and seed coat) and fruit. Vascular or provascular tissues may be targeted. Alternatively, one or several genes described in the present invention may be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed.

E. Inhibiting Expression of the Peptides of the Invention

In some embodiments of the present invention, ethylene-related processes are modulated by inhibiting gene expression in a plant. As noted above, the invention provides a method of inhibiting ACC oxidase, or EIN2 activity in a plant, the method comprising introducing a construct comprising a promoter operably linked to a nucleic acid sequence encoding a polynucleotide sequence such as ACC oxidase (represented by SEQ ID NOs: 2, 7, 11, and 16), or EIN2 (represented by SEQ ID NO: 41) wherein the isolated nucleic acid is at least 90% identical to the polynucleotide sequence.

For example, expression cassettes of the invention can be used to suppress endogenous expression of genes encoding an ACC oxidase protein. For example, in some embodiments, the present invention provides methods of delaying senescence in a plant by decreasing expression of a gene encoding an ACC oxidase polypeptide in a plant. A plant with delayed senescence possesses phenotypic characteristics that are recognizable to the skilled practitioner, e.g., abnormal developmental patterns such as the presence of staygreen traits. The affected plant part can be a reproductive plant part or vegetative plant part. For example, the plant part may include leaves, but can also include fruit, ovules, seeds, pollen, embryonic tissue, flowers, flower parts such as pistils, stamens, sepals, petals, carpels, stems, tubers, roots, vascular tissue, provascular tissue or root or stem meristem. For example, in some embodiments of the present invention, a tissue specific promoter, such as a seed specific promoter, can be used to create a transgenic plant with altered seed characteristics as compared to a wild type plant. A plant with altered seed characteristics, for example, may have greater seed yield.

A number of methods can be used to inhibit gene expression in a plant. The ability to inhibit gene function in a variety of organisms using double stranded RNA (also referred to as RNAi) is well known (Ding, *Current Opinions in Biotechnology* 11:152-156 (2000)). Expression cassettes encoding RNAi typically comprise a polynucleotide sequence at least substantially identical to the target gene linked to a complementary polynucleotide sequence. The sequence and its complement are often connected through a linker sequence that allows the transcribed RNA molecule to fold over such that the two sequences hybridize to each other. RNAi has been shown to inhibit genetic function in plants (see Chuang et al *Proc. Natl. Acad. Sci. USA* 97:4985-4990 (2000)).

In addition, antisense technology can be conveniently used. To accomplish this, a nucleic acid segment at least substantially identical to the desired gene is cloned and operably linked to a promoter such that the antisense strand of RNA will be transcribed. The expression cassette is then transformed into a plant and the antisense strand of RNA is produced. In plant cells, it has been suggested that antisense RNA inhibits gene expression by preventing the accumulation of mRNA which encodes the protein of interest, see, e.g., Sheehy et al., *Proc. Natl. Acad. Sci. USA*, 85:8805 8809 (1988), and Hiatt et al., U.S. Pat. No. 4,801,340.

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990), and U.S. Pat. Nos. 5,034,323, 5,231,020, and 5,283,184.

For these techniques (RNAi, antisense or sense suppression), the introduced sequence in the expression cassette need not have absolute identity to the target gene. In addition, the sequence need not be full length, relative to either the primary transcription product or fully processed mRNA. One of skill in the art will also recognize that using these technologies families of genes can be suppressed with a transcript. For instance, if a transcript is designed to have a sequence that is conserved among a family of genes, then multiple members of a gene family can be suppressed. Conversely, if the goal is to only suppress one member of a homologous gene family, then the transcript should be targeted to sequences with the most variance between family members.

Gene expression can also be inactivated using recombinant DNA techniques by transforming plant cells with constructs comprising transposons or T-DNA sequences. Mutants prepared by these methods are identified according to standard techniques. For instance, mutants can be detected by PCR or by detecting the presence or absence of ACC oxidase mRNA, e.g., by northern blots or reverse transcriptase PCR(RT-PCR).

Catalytic RNA molecules or ribozymes can also be used to inhibit expression of embryo-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA cleaving activity upon them, thereby increasing the activity of the constructs. The design and use of target RNA-specific ribozymes is described in Haseloff et al. *Nature*, 334:585-591 (1988).

Oligonucleotide-based triple-helix formation can also be used to disrupt gene expression. Triplex DNA can inhibit DNA transcription and replication, generate site-specific mutations, cleave DNA, and induce homologous recombination (see, e.g., Havre and Glazer, *J. Virology* 67:7324-7331 (1993); Scanlon et al., *FASEB J.* 9:1288-1296 (1995); Giovannangeli et al., *Biochemistry* 35:10539-10548 (1996); Chan and Glazer, *J. Mol. Medicine.* (Berlin) 75:267-282 (1997)). Triple helix DNAs can be used to target the same sequences identified for antisense regulation.

Methods for introducing genetic mutations described can also be used to select for plants with decreased expression of the peptides of the invention, such as ACC oxidase, or EIN2.

Another strategy is to inhibit the ability of a peptide of the invention to interact with itself or with other proteins. This can be achieved, for instance, using antibodies specific to the peptide of the invention. For example, cell-specific expression of antibodies can be used to inactivate functional domains through antibody:antigen recognition (see, Hupp et al., *Cell* 83:237-245 (1995)).

Alternatively, dominant negative mutants of peptides of the invention can be prepared by expressing a transgene that encodes a truncated peptide. Use of dominant negative mutants to produce inactive target genes in transgenic plants is described in Mizukami et al., *Plant Cell* 8:831-845 (1996). In this approach, non-functional, mutant peptides of the invention which retain the ability to interact with wild-type subunits are introduced into a plant. This approach can be used to decrease ethylene sensitivity in plants by introducing dominant negative mutants of ethylene receptors into plants. For example, an altered *Arabidopsis* ERS gene can be used to confer dominant ethylene insensitivity (Hua et al, *Science* 269:1712-4 (1995)). An ETR1 mutant from *Arabidopsis* has also been used (Wilkinson et al, *Nat. Biotechnol.* 15:444-7 (1997) and Chang et al *Science.* 262:539-44 (1993)).

F. Inserting Non-Maize ACC-Modulating Enzymes

Another method of the invention involves modulating ethylene production in maize through the introduction of non-maize genes. In one embodiment of the invention, these genes encode products which increase ethylene production or increase transcription of senescence factors. In another embodiment, these genes encode products which decrease ethylene production or decrease transcription of senescence factors.

One method for inhibition involves the consumption of an intermediate in the ethylene pathway. ACC is an ethylene precursor that is metabolized by several enzymes, such as ACC deaminase or ACC malonyl transferase. The ACC deaminase enzyme metabolizes ACC by converting it to α-ketobutyrate and ammonia. Thus, an ACC deaminase enzyme which possesses sufficient kinetic capabilities can inhibit the synthesis of ethylene by removing ACC from the metabolic pool in the tissues where the ACC deaminase is located.

ACC deaminase is not known in the art to be produced or expressed naturally in maize. Therefore, in order to pursue a method of inhibiting ethylene synthesis in plants by degrading ACC, an ACC deaminase encoding gene must be identified and then be made capable of being expressed in maize. Methods describing the identification, isolation, and introduction of an ACC deaminase gene into a plant are discussed in U.S. Pat. No. 5,702,933.

G. Preparation of Recombinant Vectors

The invention provides a recombinant expression cassette comprising a promoter sequence operably linked to a nucleic acid sequence encoding a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41) wherein the isolated nucleic acid is at least 90% identical to the polynucleotide sequence.

To use isolated sequences in the above techniques, recombinant DNA vectors suitable for transformation of plant cells are prepared. Techniques for transforming a wide variety of higher plant species are well known and described in the technical and scientific literature, e.g., Weising et al., *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation.

Alternatively, the plant promoter may direct expression of the polynucleotide of the invention in a specific tissue (tissue-specific promoters, organ-specific promoters) or specific environmental condition (inducible promoters).

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfaron or Basta.

Nucleic acid sequences of the invention, e.g., nucleic acid sequences that encode ACC oxidase, ACC deaminase, ERS1, ETR2, or EIN2 proteins, are expressed recombinantly in plant cells to enhance and increase levels of endogenous plant transcription factors. For example, ACC oxidase nucleic acid sequences of the invention are expressed recombinantly in plant cells to enhance and increase levels of endogenous ACC oxidase polypeptides. A variety of different expression constructs, such as expression cassettes and vectors suitable for transformation of plant cells can be prepared. Techniques for transforming a wide variety of higher plant species are well known and described in the technical and scientific literature, e.g., Weising et al., *Ann. Rev. Genet.* 22:421-477 (1988). A DNA sequence coding for a polypeptide described in the present invention, e.g., a cDNA sequence encoding a full length ACC oxidase protein, can be combined with cis-acting (promoter and enhancer) transcriptional regulatory sequences to direct the timing, tissue type and levels of transcription in the intended tissues of the transformed plant. Translational control elements can also be used.

The invention provides a nucleic acid encoding an ACC oxidase, ACC deaminase, ERS1, ETR2, or EIN2 polypeptide operably linked to a promoter which, in some embodiments, is capable of driving the transcription of the coding sequence in plants. The promoter can be, e.g., derived from plant or viral sources. The promoter can be, e.g., constitutively active, inducible, or tissue specific. In construction of recombinant expression cassettes, vectors, transgenics, of the invention, different promoters can be chosen and employed to differentially direct gene expression, e.g., in some or all tissues of a plant or animal. Typically, as discussed above, desired promoters are identified by analyzing the 5' sequences of a genomic clone corresponding to the embryo-specific genes described here.

1. Constitutive Promoters

A promoter fragment can be employed which will direct expression of a nucleic acid encoding an ACC oxidase, ACC deaminase, ERS1, ETR2, or EIN2 protein in all transformed cells or tissues, e.g. as those of a regenerated plant. Such promoters are referred to herein as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless, *Arch. Virol.* 142:183-191 (1997)); the 1'- or 2'-promoter derived from T-DNA of *Agrobacterium tumefaciens* (see, e.g., Mengiste (1997) supra; O'Grady, *Plant Mol. Biol.* 29:99-108 (1995); the promoter of the tobacco mosaic virus; the promoter of Figwort mosaic virus (see, e.g., Maiti, *Transgenic Res.* 6:143-156 (1997)); actin promoters, such as the *Arabidopsis* actin gene promoter (see, e.g., Huang, *Plant Mol. Biol.* 33:125-139 (1997)); alcohol dehydrogenase (Adh) gene promoters (see, e.g., Millar, *Plant Mol. Biol.* 31:897-904 (1996)); ACT11 from *Arabidopsis* (Huang et al., *Plant Mol. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al., *Plant Physiol.* 104:1167-1176 (1994)), GPc1 from maize (GenBank No. X15596, Martinez et al., *J. Mol. Biol.* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf et al., *Plant Mol. Biol.* 29:637-646 (1995).

2. Inducible Promoters

Alternatively, a plant promoter may direct expression of the nucleic acids described in the present invention, e.g., nucleic acids encoding an ACC oxidase, ACC deaminase, ERS1, ETR2, or EIN2 protein, under the influence of changing environmental conditions or developmental conditions. Examples of environmental conditions that may effect transcription by inducible promoters include anaerobic conditions, elevated temperature, drought, or the presence of light. Example of developmental conditions that may effect transcription by inducible promoters include senescence. Such promoters are referred to herein as "inducible" promoters. For example, the invention incorporates the drought-inducible promoter of maize (Busk (1997) supra); the cold, drought, and high salt inducible promoter from potato (Kirch et al., *Plant Mol. Biol.* 33:897 909 (1997)). Examples of developmental conditions include cell aging, and embryogenesis. For example, the invention incorporates the senescence inducible promoter of *Arabidopsis*, SAG 12, (Gan and Amasino, *Science* 270:1986-1988 (1995)) and the embryogenesis related promoters of LEC1 (Lotan et al., *Cell,* 93:1195-1205 (1998)), LEC2 (Stone et al., *Proc. Natl. Acad. Sci. USA* 98:11806-11811 (2001)), FUS3 (Luerssen, *Plant J.* 15:755-764 (1998)), AtSERK1 (Hecht et al., *Plant Physiol* 127:803-816 (2001)), and AGL15 (Heck et al., *Plant Cell* 7:1271-1282 (1995)).

Alternatively, plant promoters which are inducible upon exposure to plant hormones, such as auxins or cytokinins, are used to express the nucleic acids of the invention. For example, the invention can use the auxin response elements E1 promoter fragment (AuxREs) in the soybean (*Glycine max* L.) (Liu, *Plant Physiol.* 115:397-407 (1997)); the auxin-responsive *Arabidopsis* GST6 promoter (also responsive to salicylic acid and hydrogen peroxide) (Chen, *Plant J.* 10: 955-966 (1996)); the auxin-inducible parC promoter from tobacco (Sakai, *Plant Cell Physiol.* 37:906-913 (1996)); a plant biotin response element (Streit, *Mol. Plant. Microbe Interact.* 10:933-937 (1997)); and, the promoter responsive to the stress hormone abscisic acid (Sheen, *Science* 274:1900-1902 (1996)). The invention can also use the cytokinin inducible promoters of ARR5 (Brandstatter and Kieber, *Plant Cell* 10:1009-1019 (1998)), ARR6 (Brandstatter and Kieber, *Plant Cell* 10:1009-1019 (1998)), ARR2 (Hwang and Sheen, *Nature* 413:383-389 (2001)), the ethylene responsive promoter of ERF1 (Solano et al., *Genes Dev.* 12:3703-3714 (1998)), and the β-estradiol inducible promoter of XVE (Zuo et al., *Plant J* 24:265-273 (2000)).

Plant promoters which are inducible upon exposure to chemicals reagents which can be applied to the plant, such as herbicides or antibiotics, are also used to express the nucleic acids of the invention. For example, the maize In2 2 promoter, activated by benzenesulfonamide herbicide safeners, can be used (De Veylder, *Plant Cell Physiol.* 38:568-577 (1997)) as well as the promoter of the glucocorticoid receptor protein fusion inducible by dexamethasone application (Aoyama, *Plant J.* 11:605-612 (1997)); application of different herbicide safeners induces distinct gene expression patterns, including expression in the root, hydathodes, and the shoot apical meristem. The coding sequence of the described nucleic acids can also be under the control of, e.g., a tetracycline inducible promoter, e.g., as described with transgenic tobacco plants containing the *Avena sativa* L. (oat) arginine decarboxylase gene (Masgrau, *Plant J.* 11:465-473 (1997)); or, a salicylic acid responsive element (Stange, *Plant J.* 11:1315-1324 (1997)).

3. Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, anthers, or any embryonic tissue. Reproductive tissue-specific promoters may be, e.g., ovule-specific, embryo-specific, endosperm-specific, integument-specific, seed and seed coat-specific, pollen-specific, petal-specific, sepal-specific, anther-specific or some combination thereof.

Suitable seed-specific promoters are derived from the following genes: MAC1 from maize (Sheridan, *Genetics* 142: 1009-1020 (1996)); Cat3 from maize (GenBank No. L05934, Abler *Plant Mol. Biol.* 22:10131-10138 (1993)); vivparous-1 from *Arabidopsis* (Genbank No. U93215); atmyc1 from *Arabidopsis* (Urao, *Plant Mol. Biol.* 32:571-576 (1996); Conceicao *Plant* 5:493-505 (1994)); napA and BnCysP1 from *Brassica napus* (GenBank No. J02798, Josefsson, *JBL* 26:12196-12201 (1987), Wan et al., *Plant J* 30:1-10 (2002)); and the napin gene family from *Brassica napus* (Sjodahl, *Planta* 197: 264-271 (1995)). Fruit specific promoters include the promoter from the CYP78A9 gene (Ito and Meyerowitz, *Plant Cell* 12:1541-1550 (2000)).

The ovule-specific BEL1 gene described in Reiser, *Cell* 83:735-742 (1995), GenBank No. U39944, can also be used. See also Ray, *Proc. Natl. Acad. Sci. USA* 91:5761-5765 (1994). The egg and central cell specific FIE1 promoter is also a useful reproductive tissue-specific promoter.

Sepal and petal specific promoters are also used to express nucleic acids of the invention in a reproductive tissue-specific manner. For example, the *Arabidopsis* floral homeotic gene APETALA1 (ΔP1) encodes a putative transcription factor that is expressed in young flower primordia, and later becomes localized to sepals and petals (see, e.g., Gustafson Brown, *Cell* 76:131-143 (1994); Mandel, *Nature* 360:273-277 (1992)). A related promoter, for AP2, a floral homeotic gene that is necessary for the normal development of sepals and petals in floral whorls, is also useful (see, e.g., Drews, *Cell* 65:991-1002 (1991); Bowman, *Plant Cell* 3:749-758 (1991)). Another useful promoter is that controlling the expression of the unusual floral organs (ufo) gene of *Arabidopsis*, whose expression is restricted to the junction between sepal and petal primordia (Bossinger, *Development* 122: 1093-1102 (1996)).

A maize pollen specific promoter has been identified in maize (Guerrero, *Mol. Gen. Genet.* 224:161-168 (1990)). Other genes specifically expressed in pollen are described, e.g., by Wakeley, *Plant Mol. Biol.* 37:187-192 (1998); Ficker, *Mol. Gen. Genet.* 257:132-142 (1998); Kulikauskas, *Plant Mol. Biol.* 34:809-814 (1997); Treacy, *Plant Mol. Biol.* 34:603-611 (1997).

Promoters specific for pistil and silique valves, inflorescence meristems, cauline leaves, and the vasculature of stem and floral pedicels include promoters from the FUL gene Mandel and Yanofsky, *Plant Cell*, 7:1763-1771 (1995). Promoters specific for developing carpels, placenta, septum, and ovules are also used to express LEC2 nucleic acids in a tissue-specific manner. They include promoters from the SHP1 and SHP2 genes (Flanagan et al. *Plant J* 10:343-353 (1996), Savidge et al., *Plant Cell* 7(6):721-733 (1995)). Promoters specific for the anther tapetum may be derived from the TA29 gene (Goldberg et al., *Philos Trans. R. Soc. Lond. B. Biol. Sci.* 350:5-17 (1995)).

Other suitable promoters include those from genes encoding embryonic storage proteins. For example, the gene encoding the 2 S storage protein from *Brassica napus*, Dasgupta, *Gene* 133:301-302 (1993); the 2 s seed storage protein gene family from *Arabidopsis*; the gene encoding oleosin 20 kD from *Brassica napus*, GenBank No. M63985; the genes encoding oleosin A, Genbank No. U09118, and, oleosin B, Genbank No. U09119, from soybean; the gene encoding oleosin from *Arabidopsis*, Genbank No. Z17657; the gene encoding oleosin 18 kD from maize, GenBank No. J05212, Lee, *Plant Mol. Biol.* 26:1981-1987 (1994); and, the gene encoding low molecular weight sulphur rich protein from soybean, Choi, *Mol Gen, Genet.* 246:266-268 (1995), can be used. The tissue specific E8 promoter from tomato is particularly useful for directing gene expression so that a desired gene product is located in fruits. Suitable promoters may also include those from genes expressed in vascular tissue, such as the ATHB-8, AtPIN1, AtP5K1 or TED3 genes (Baima et al., *Plant Physiol.* 126:643-655 (2001), Galaweiler et al, *Science* 282:2226-2230 (1998), Elge et al., *Plant J.* 26:561-571 (2001), Igarashi et al., *Plant Mol. Biol.* 36:917-927 (1998)).

A tomato promoter active during fruit ripening, senescence and abscission of leaves and, to a lesser extent, of flowers can be used (Blume, *Plant J.* 12:731-746 (1997)). Other exemplary promoters include the pistil specific promoter in the potato (*Solanum tuberosum* L.) SK2 gene, encoding a pistil specific basic endochitinase (Ficker, *Plant Mol. Biol.* 35:425-431 (1997)); the Blec4 gene from pea (*Pisum sativum* cv. Alaska), active in epidermal tissue of vegetative and floral shoot apices of transgenic alfalfa. This makes it a useful tool to target the expression of foreign genes to the epidermal layer of actively growing shoots.

A variety of promoters specifically active in vegetative tissues, such as leaves, stems, roots and tubers, can also be used to express the nucleic acids used in the methods of the invention. For example, promoters controlling patatin, the major storage protein of the potato tuber, can be used, e.g., Kim, *Plant Mol. Biol.* 26:603-615 (1994); Martin, *Plant J.* 11:53-62 (1997). The ORF13 promoter from *Agrobacterium rhizogenes* which exhibits high activity in roots can also be used (Hansen, *Mol. Gen. Genet.* 254:337-343 (1997)). Other useful vegetative tissue-specific promoters include: the tarin promoter of the gene encoding a globulin from a major taro (*Colocasia esculenta* L. Schott) corm protein family, tarin (Bezerra, *Plant Mol. Biol.* 28:137-144 (1995)); the curculin promoter active during taro corm development (de Castro, *Plant Cell* 4:1549-1559 (1992)) and the promoter for the tobacco root specific gene TobRB7, whose expression is localized to root meristem and immature central cylinder regions (Yamamoto, *Plant Cell* 3:371-382 (1991)).

Leaf-specific promoters, such as the ribulose biphosphate carboxylase (RBCS) promoters can be used. For example, the tomato RBCS1, RBCS2 and RBCS3A genes are expressed in leaves and light grown seedlings, only RBCS1 and RBCS2 are expressed in developing tomato fruits (Meier, *FEBS Lett.* 415:91-95 (1997)). A ribulose bisphosphate carboxylase promoters expressed almost exclusively in mesophyll cells in leaf blades and leaf sheaths at high levels, described by Matsuoka, *Plant J.* 6:311-319 (1994), can be used. Another leaf-specific promoter is the light harvesting chlorophyll a/b binding protein gene promoter, see, e.g., Shiina, *Plant Physiol.* 115:477-483 (1997); Casal, *Plant Physiol.* 116:1533-1538 (1998). The *Arabidopsis thaliana* myb-related gene promoter (Atmyb5) described by Li, *FEBS Lett.* 379:117-121 (1996), is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16-cell stage of embryo development and persists beyond the heart stage. A leaf promoter identified in maize by Busk, *Plant J.* 11:1285-1295 (1997), can also be used.

Another class of useful vegetative tissue-specific promoters are meristematic (root tip and shoot apex) promoters. For example, the "SHOOTMERISTEMLESS" and "SCARE-CROW" promoters, which are active in the developing shoot or root apical meristems, described by Di Laurenzio, *Cell* 86:423-433 (1996); and, Long, *Nature* 379:66-69 (1996); can be used. Another useful promoter is that which controls the expression of 3 hydroxy 3 methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto, *Plant Cell.* 7:517-527 (1995)). Also useful are kn1 related genes from maize and other species which show meristem specific expression, see, e.g., Granger, *Plant Mol. Biol.* 31:373-378 (1996); Kerstetter, *Plant Cell* 6:1877-1887 (1994); Hake, *Philos. Trans. R. Soc. Lond. B. Biol. Sci.* 350:45-51 (1995). For example, the *Arabidopsis thaliana* KNAT1 or KNAT2 promoters. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln, *Plant Cell* 6:1859-1876 (1994)).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, a nucleic acid described in the present invention is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai, *Proc. Natl. Acad. Sci. USA*

92:1679-1683 (1995)) the rice tungro bacilliform virus (RTBV), which replicates only in phloem cells in infected rice plants, with its promoter which drives strong phloem specific reporter gene expression; the cassava vein mosaic virus (CVMV) promoter, with highest activity in vascular elements, in leaf mesophyll cells, and in root tips (Verdaguer, *Plant Mol. Biol.* 31:1129-1139 (1996)).

H. Production of Transgenic Plants

In a further aspect, the invention provides a transgenic plant comprising a recombinant expression cassette comprising a promoter sequence operably linked to a nucleic acid sequence encoding a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41), wherein the isolated nucleic acid is at least 90% identical to the polynucleotide sequence.

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistics, e.g., DNA particle bombardment.

Microinjection techniques are known in the art and well described in the scientific and patent literature. The introduction of DNA constructs using polyethylene glycol precipitation is described in Paszkowski et al. *Embo J.* 3:2717-2722 (1984). Electroporation techniques are described in Fromm et al. *Proc. Natl. Acad. Sci. USA* 82:5824 (1985). Biolistic transformation techniques are described in Klein et al. *Nature* 327:70-73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as decreased farnesyltransferase activity. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al., *Ann. Rev, of Plant Phys.* 38:467-486 (1987).

The nucleic acids of the invention can be used to confer desired traits on essentially any plant, including maize. Thus, the invention has use over a broad range of plants, including species from the genera *Anacardium, Arachis, Asparagus, Atropa, Avena, Brassica, Chlamydomonas, Chlorella, Citrus, Citrullus, Capsicum, Carthamus, Cocos, Coffea, Cucumis, Cucurbita, Cyrtomium, Daucus, Elaeis, Fragaria, Glycine, Gossypium, Helianthus, Heterocallis, Hordeum, Hyoscyamus, Lactuca, Laminaria, Linum, Lolium, Lupinus, Lycopersicon, Macrocystis, Malus, Manihot, Majorana, Medicago, Nereocystis, Nicotiana, Olea, Oryza, Osmunda, Panieum, Pannesetum, Persea, Phaseolus, Pistachia, Pisum, Pyrus, Polypodium, Prunus, Pteridium, Raphanus, Ricinus, Secale, Senecio, Sinapis, Solanum, Sorghum, Theobromus, Trigonella, Triticum, Vicia, Vitis, Vigna*, and *Zea*.

I. Detection of the Transgenic Plants of the Present Invention

In another aspect, the invention provides a method of modulating ACC oxidase, ERS, ETR, or EIN2 activity in a plant. In an exemplary embodiment, the method further comprises selecting a plant with a phenotype of delayed senescence in its reproductive plant structure. In another exemplary embodiment, the reproductive structure is a seed. In yet another exemplary embodiment, the phenotype is multiple embryos in a single seed. In yet another exemplary embodiment, the construct is introduced by a sexual cross.

In some embodiments, screening further comprises detecting a plant having a desirable phenotype. For example, leaf color can be examined to determine if the photosynthetic life-span of the plant has been affected. Plants with extended photosynthetic life cycles are characterized by leaves that stay green for a longer duration of time as compared to wild type plants. In addition, chlorophyll levels can be measured using well known techniques. Plants that tolerate denser planting can be selected by testing the ability of the plant to grow at higher density. The size of plant vegetative and reproductive structures can be examined to determine if they are larger or smaller than those of a wild type plants. Transgenic plants of the present invention may possess larger fruit, ovules, seeds, pollen, embryonic tissue, flowers, flower parts such as pistils, stamens, sepals, petals, carpels, leaves, stems, tubers, roots, vascular tissue, provascular tissue or root or stem meristems. The resultant transgenic plants can be assayed for increased drought tolerance. Methods for assaying for increased drought tolerance are known and include measuring transpiration rate of transgenic plants, stomatal conductance, rate of water loss in a detached leaf assay or examining leaf turgor. Transgenic plants with decreased transpiration rates, for example, have increased drought tolerance.

Means for detecting and quantifying mRNA or proteins are well known in the art, e.g., Northern Blots, Western Blots or activity assays. For example, after introduction of the expression cassette into a plant, the plants are screened for the presence of the transgene and crossed to an inbred or hybrid line. Progeny plants are then screened for the presence of the transgene and self-pollinated. Progeny from the self-pollinated plants are grown. The resultant transgenic plants can be examined for any of the phenotypic characteristics associated with altered ethylene-related processes, e.g., characteristics associated with staygreen traits or delayed senescence. For example, using the methods of the present invention, inhibition of the nucleic acids or proteins described in the present invention may delay senescence in cells of a vegetative or reproductive plant structure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Standard methods were used to prepare the nucleic acid sequences disclosed here. The methods are described briefly below.

RT-PCR Analysis

Fifty μg total RNA was treated with RQ1 DNase (Promega) to ensure that no contaminating DNA was present. Two μg total RNA was used directly for cDNA synthesis using the Omniscript RT kit (Qiagen) with oligo-dT(20) (SEQ ID NO:49) as the primer.

Analysis of transcript abundance was accomplished using the QuantiTect SYBR Green PCR kit (Qiagen). Reactions contained 1× buffer, 0.5 μl of the reverse transcription reaction (equivalent to 50 ng total RNA) and 0.25 μM (final concentration) forward and reverse primers (see table below) in a total reaction volume of 25 μl.

| GENE | FORWARD PRIMER (5'-3') | SEQ ID NO: | REVERSE PRIMER (5'-3') | SEQ ID NO: |
|---|---|---|---|---|
| ZmACO15 | ctcgtcttcgatcaattcccaagt | 4 | tacattatcattatttctccggctgt | 5 |
| ZmACO31 | ctcgtcttcgatcaattcccaagt | 13 | atagcaaagagggcaactagctagt | 14 |
| ZmACO20 | ctcatcctgctgctccaggacgac | 9 | tccacgatacacgcataaccaccgt | 10 |
| ZmACO35 | ctcatcctgctgctccaggacgac | 18 | acacacataactgtgccactataagca | 19 |
| ZmERS14 | gagttagtcctcaggatctacctcatgt | 23 | caactcaatccgctggtaggacatact | 24 |
| ZmERS25 | gagttagtcctcaggatctacctcatgt | 28 | caattcaatccgctggtagcatatgt | 29 |
| ZmETR9 | gctatgtatgtgtgaaatttgagattagga | 33 | agctaacctggcagaaattagttaccga | 34 |
| ZmETR40 | gctatgtatgtgtgaaatttgagattagga | 38 | aagctacagcggtctattgagaattct | 39 |
| ZmEIN2-25 | tgggtggtactactacacagcttcct | 43 | aggcttggagaacgcagggtccaaga | 44 |
| ZmEIN3-2 | acccccgtacaagaagcctcatga | 45 | gtttatggctggccggacatacaagt | 46 |
| ZmEIN3-3 | acccccgtacaagaagcctcatga | 47 | acgaccaagaccctatagactcgacactc | 48 |

DNA and RNA Purification

For total nucleic acid isolation, leaves of B73 were collected at the indicated times, quick-frozen in liquid nitrogen and ground to a fine powder. Ten mL of extraction buffer [100 mM Tris (pH 8.0), 50 mM EDTA, 200 mM NaCl, 1% SDS, 10 μl/mL β-mercaptoethanol] was added and mixed thoroughly until thawed. Ten mL of Phenol/Chloroform (1:1, vol:vol) was added and mixed thoroughly. Samples were centrifuged 10 min at 8,000 rpm, the supernatant removed to a new tube and the nucleic acid precipitated at −20° C. following addition of 1/10 vol 3M sodium acetate and 1 vol isopropanol. Total nucleic acid was pelleted by centrifugation at 8,000 rpm and resuspended in 1 mL TE. One half of the prep was used for DNA purification and the remaining half was used for RNA purification.

For DNA purification, 500 μg DNase-free RNase was added to the tube and incubated at 37° C. for 1 hr. Following RNase digestion, an equal volume of Phenol/Chloroform (1:1, vol:vol) was added and mixed thoroughly. Samples were centrifuged 10 min at 10,000 rpm, the supernatant removed to a new tube and the DNA precipitated at −20° C. following addition of 1/10 vol 3M sodium acetate and 1 vol isopropanol. DNA was resuspended in sterile water and the concentration determined spectrophotometrically. To determine DNA integrity, 20 mg of DNA was separated on a 1.8% agarose gel and visualized following staining with ethidium bromide. RNA was purified by 2 rounds of LiCl$_2$ precipitation according to methods described by Sambrook et al., *Molecular Cloning—A Laboratory Manual*, Cold Spring Harbor Laboratory, Cold Spring Harbor, N.Y., (1989).

Reactions were carried out using an ABI PRISM 7700 sequence detection system under the following conditions: 95° C./15 min. (1 cycle); 95° C./30 sec, 62° C./30 sec, 72° C./2 min (50 cycles); 72° C./5 min (1 cycle). Each gene was analyzed a minimum of four times.

All the primer combinations were initially run and visualized on an agarose gel to confirm the presence single product of the correct size. All amplification products were subcloned into the pGEM-T Easy vector system (Promega) to use for generation of standard curves to facilitate conversion of expression data to a copy/μg RNA basis.

Cloning of the Nucleic Acids of the Invention From *Zea Mays*

ACC oxidase is provided as an example of the cloning of the nucleic acids of the invention. One of skill in the art will recognize that the other nucleic acids of the invention can be cloned by the methods described below and by using the appropriate primers (see the "RT-PCR Analysis" part of the Example section for a listing of appropriate primers).

To clone the maize ACC oxidase gene(s) from maize, primers ACOF1 (ctcatcctgctgctccaggacgac; SEQ ID NO:9) and ACOF1 (cctcgaaccgtggctccttggcctcgaactt; SEQ ID NO:50) were designed using currently available sequences information located in GenBank to amplify two ACC oxidase gene fragments from maize genomic DNA. Following verification of these ACC oxidase fragments by sequencing, a maize (W64) endosperm cDNA library (gift of Dr. B. Larkins) was screened (using the same conditions as outlined above for genomic library screening) to identify a full-length cDNA. This cDNA was then used to screen a maize (B73) genomic library (same conditions as above). Following identification of several genomic clones, a similar approach as outlined above was used for characterization of the various maize ACC oxidase genes.

Western Blot Analysis

For total protein isolation, leaves of B73 were collected at the indicated times, quick-frozen in liquid nitrogen and ground to a fine powder. One mL of extraction buffer [100 mM Tris (pH 7.5), 100 mM NaCl, 50 mM CaCl$_2$, 50 mM MgCl] was added to approximately 0.5 g frozen powder and mixed thoroughly. Samples were centrifuged 10 min at 10,000 rpm, the supernatant removed to a new tube and the concentration determined spectrophotometrically according to the methods of Bradford, *Anal. Biochem.* 72:248-254 (1976) using a set of BSA standards of known concentration.

Ten mg of protein was separated on 12.5% SDS-PAGE gels and transferred to nitrocellulose membranes. Blots were probed with antibodies to the isolated protein.

Chlorophyll Extraction

Leaves were frozen in liquid nitrogen and ground to a fine powder. Approximately 0.1 g was removed to a 1.5 mL tube and the chlorophyll extracted 3× with 1 mL of acetone. Individual extractions were combined and the chlorophyll content determined spectrophotometrically according to well known methods.

The above example is provided to illustrate the invention but not to limit its scope. Other variants of this invention will be readily apparent to one of ordinary skill in the art and are encompassed by the appended claims.

What is claimed is:

1. An isolated nucleic acid vector comprising a recombinant expression cassette having a polynucleotide sequence encoding an ERS1 polypeptide, wherein the ERS1 polypeptide comprises the sequence of SEQ ID NO: 22.

2. The isolated nucleic acid vector of claim 1, wherein the polynucleotide sequence is at least 90% identical to SEQ ID NO: 21.

3. A transgenic plant comprising a recombinant expression cassette having a polynucleotide sequence encoding an ERS1 polypeptide, wherein the ERS1 polypeptide comprises the sequence of SEQ ID NO:22.

4. The transgenic plant of claim 3, wherein the polynucleotide sequence is at least 90% identical to SEQ ID NO: 21.

5. The transgenic plant of claim 3, which is a maize plant.

* * * * *

UNITED STATES PATENT AND TRADEMARK OFFICE
CERTIFICATE OF CORRECTION

| | | |
|---|---|---|
| PATENT NO. | : 8,704,044 B2 | Page 1 of 1 |
| APPLICATION NO. | : 11/688162 | |
| DATED | : April 22, 2014 | |
| INVENTOR(S) | : Gallie et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 571 days.

Signed and Sealed this
Twenty-sixth Day of January, 2016

Michelle K. Lee
*Director of the United States Patent and Trademark Office*